US011439815B2

(12) United States Patent
Rousso et al.

(10) Patent No.: US 11,439,815 B2
(45) Date of Patent: Sep. 13, 2022

(54) PROTEIN ACTIVITY MODIFICATION

(71) Applicant: Impulse Dynamics NV, Willemstad (CW)

(72) Inventors: Benny Rousso, Rishon-LeZion (IL); Yuval Mika, Closter, NJ (US); Hani N. Sabbah, Waterford, MI (US); Shlomo Ben-Haim, Marlow (GB)

(73) Assignee: Impulse Dynamics NV, Willemstad (NL)

( * ) Notice: Subject to any disclaimer, the term of this patent is extended or adjusted under 35 U.S.C. 154(b) by 0 days.

(21) Appl. No.: 15/942,637

(22) Filed: Apr. 2, 2018

(65) Prior Publication Data
US 2018/0221655 A1    Aug. 9, 2018

Related U.S. Application Data

(63) Continuation of application No. 11/792,811, filed as application No. PCT/US2005/044557 on Dec. 9, 2005, now Pat. No. 9,931,503, which is a continuation-in-part of application No. PCT/IL2005/000316, filed on Mar. 18, 2005, which is a continuation-in-part of application No. PCT/IL2004/000797, filed on Sep. 5, 2004, and a continuation-in-part of application No.
(Continued)

(51) Int. Cl.
*A61N 1/32* (2006.01)
*C12N 13/00* (2006.01)
*A61N 1/20* (2006.01)

(52) U.S. Cl.
CPC .............. *A61N 1/32* (2013.01); *A61N 1/205* (2013.01); *A61N 1/326* (2013.01); *C12N 13/00* (2013.01)

(58) Field of Classification Search
CPC .......... A61N 1/205; A61N 1/32; A61N 1/362; A61N 1/3627
See application file for complete search history.

(56) References Cited

U.S. PATENT DOCUMENTS

| 1,918,386 A | 7/1933 | Esau |
| 3,211,154 A | 10/1965 | Becker et al. |

(Continued)

FOREIGN PATENT DOCUMENTS

| EP | 0148687 | 7/1985 |
| EP | 0156593 | 10/1985 |

(Continued)

OTHER PUBLICATIONS

Bers "Excitation-Contracting Coupling", Excitation-Contraction Coupling and Cardiac Contractile Force, 2nd Ed., Chap.8: 203-407, 2001. (Part I: pp. 208-282).
(Continued)

*Primary Examiner* — Michael J D'Abreu

(57) ABSTRACT

A method of modifying cardiac tissue behavior, comprising applying a therapeutically effective electric field having an effect of modifying protein activation levels of at least one protein, and repeatedly applying the field at time intervals timed to increase the activation levels of the at least one protein beyond an activation level achieved by natural and/or paced excitation of the muscle without the application, to an extent about at least as high as a decay of the activation between applications of the field.

24 Claims, 46 Drawing Sheets

Related U.S. Application Data

PCT/IL2004/000664, filed on Jul. 21, 2004, and a continuation-in-part of application No. PCT/IL2004/000551, filed on Jun. 20, 2004, and a continuation-in-part of application No. PCT/IL2004/000550, filed on Jun. 20, 2004, and a continuation-in-part of application No. 10/804,560, filed on Mar. 18, 2004, now abandoned, said application No. PCT/US2005/044557 is a continuation-in-part of application No. PCT/US2004/007589, filed on Mar. 10, 2004.

(60) Provisional application No. 60/719,517, filed on Sep. 22, 2005, provisional application No. 60/677,761, filed on May 4, 2005, provisional application No. 60/654,056, filed on Feb. 17, 2005, provisional application No. 60/634,625, filed on Dec. 9, 2004, provisional application No. 60/602,550, filed on Aug. 18, 2004, provisional application No. 60/503,075, filed on Sep. 15, 2003, provisional application No. 60/488,964, filed on Jul. 21, 2003, provisional application No. 60/480,208, filed on Jun. 20, 2003, provisional application No. 60/480,205, filed on Jun. 20, 2003, provisional application No. 60/453,349, filed on Mar. 10, 2003.

(56) References Cited

U.S. PATENT DOCUMENTS

| | | |
|---|---|---|
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,796,221 A | 3/1974 | Hagfors |
| 3,911,930 A | 10/1975 | Hagfors et al. |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,293,734 A | 10/1981 | Pepper, Jr. |
| 4,312,354 A | 1/1982 | Walters |
| 4,315,503 A | 2/1982 | Ryaby et al. |
| 4,316,472 A | 2/1982 | Mirowski et al. |
| 4,337,776 A | 7/1982 | Daly et al. |
| 4,369,791 A | 1/1983 | Friedman |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Atanabe |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,063,929 A | 11/1991 | Bartelt et al. |
| 5,067,940 A | 11/1991 | Liboff et al. |
| 5,083,564 A | 1/1992 | Scherlag |
| 5,144,554 A | 1/1992 | Zhang et al. |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,107,834 A | 4/1992 | Ideker et al. |
| 5,111,814 A | 5/1992 | Goldfarb |
| 5,111,815 A | 5/1992 | Mower |
| 5,101,814 A | 7/1992 | Palti |
| 5,129,394 A | 7/1992 | Mehra |
| 5,133,354 A | 7/1992 | Kallok |
| 5,137,021 A | 8/1992 | Wayne et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,041 A | 2/1993 | Palti |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,233,985 A | 8/1993 | Hudrlik |
| 5,236,413 A | 8/1993 | Feiring |
| 5,243,980 A | 9/1993 | Mehra et al. |

(56) References Cited

U.S. PATENT DOCUMENTS

| | | |
|---|---|---|
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,318,591 A | 6/1994 | Causey, III et al. |
| 5,320,543 A | 6/1994 | Barton et al. |
| 5,320,642 A | 6/1994 | Scherlag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,292,344 A | 8/1994 | Douglas |
| 5,346,506 A | 9/1994 | Mower et al. |
| 5,350,403 A | 9/1994 | Stroetmann et al. |
| 5,353,800 A | 10/1994 | Pohndorf et al. |
| 5,336,485 A | 11/1994 | Kroll et al. |
| 5,365,461 A | 11/1994 | Stein et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,405,365 A | 4/1995 | Hoegnelid et al. |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,447,526 A | 5/1995 | Karsdon |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-Haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bomzin et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,589 A | 8/1996 | Buchana et al. |
| 5,546,951 A | 8/1996 | Ben-Haim |
| 5,549,646 A | 8/1996 | Katz et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,825,352 A | 10/1998 | Bisset et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,871,506 A | 2/1999 | Mower |
| 5,906,607 A | 5/1999 | Taylor et al. |
| 5,962,246 A | 5/1999 | Ladner et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |

(56) References Cited

U.S. PATENT DOCUMENTS

| | | |
|---|---|---|
| 5,956,020 A | 9/1999 | D'Amico et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,026,326 A | 2/2000 | Bardy |
| 6,032,074 A | 2/2000 | Collins |
| 6,057,374 A | 2/2000 | Huntington et al. |
| 6,032,672 A | 3/2000 | Taylor |
| 6,037,882 A | 3/2000 | Levy |
| 6,041,252 A | 3/2000 | Walker et al. |
| 6,083,249 A | 4/2000 | Familoni |
| 6,066,163 A | 5/2000 | John |
| 6,067,470 A | 5/2000 | Mower |
| 6,071,305 A | 6/2000 | Brown et al. |
| 6,075,520 A | 6/2000 | Inoue et al. |
| 6,086,582 A | 7/2000 | Altman et al. |
| 6,093,167 A | 7/2000 | Houben et al. |
| 6,023,640 A | 8/2000 | Ross |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,296,693 B1 | 2/2001 | McCarthy |
| 6,298,254 B2 | 2/2001 | Tamada |
| 6,298,268 B1 | 2/2001 | Ben-Haim et al. |
| 6,285,906 B1 | 4/2001 | Ben-Haim et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 5/2001 | Mintchev et al. |
| 6,261,280 B1 | 7/2001 | Houben et al. |
| 6,278,443 B1 | 8/2001 | Amro et al. |
| 6,292,693 B1 | 9/2001 | Darvish et al. |
| 6,292,704 B1 | 9/2001 | Malonek et al. |
| 6,295,470 B1 | 9/2001 | Mower |
| 6,317,631 B1 | 11/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,417,846 B1 | 7/2002 | Lee |
| 6,424,864 B1 | 7/2002 | Matsuura |
| 6,433,069 B1 | 8/2002 | Oeltjen et al. |
| 6,463,324 B1 | 8/2002 | Ben-Haim et al. |
| 6,449,511 B1 | 9/2002 | Mintchev et al. |
| 6,452,514 B1 | 9/2002 | Philipp |
| 6,463,323 B1 | 10/2002 | Conrad-Vlasak |
| 6,473,069 B1 | 10/2002 | Gerpheide |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,587,721 B1 | 1/2003 | Prutchi et al. |
| 6,612,983 B1 | 2/2003 | Marchal |
| 6,658,297 B2 | 2/2003 | Loeb |
| 6,572,542 B1 | 3/2003 | Houben et al. |
| RE38,119 E | 5/2003 | Mower |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,583,676 B2 | 7/2003 | Krah et al. |
| 6,587,093 B1 | 7/2003 | Shaw et al. |
| 6,600,953 B2 | 7/2003 | Flesler et al. |
| 6,630,123 B1 | 7/2003 | Woltering et al. |
| 6,611,258 B1 | 8/2003 | Tanaka et al. |
| 6,633,280 B1 | 10/2003 | Matsumoto et al. |
| 6,634,895 B2 | 10/2003 | Agro |
| 6,640,135 B1 | 10/2003 | Salo et al. |
| 6,652,444 B1 | 11/2003 | Ross |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,762,752 B2 | 7/2004 | Perski et al. |
| 6,781,577 B2 | 8/2004 | Shigetaka |
| 6,810,286 B2 * | 10/2004 | Donovan .............. A61N 1/326 607/11 |
| 6,853,862 B1 | 2/2005 | Marchal et al. |
| 6,919,205 B2 | 7/2005 | Brighton |
| 6,949,081 B1 | 9/2005 | Chance |
| 7,006,871 B1 | 2/2006 | Darvish et al. |
| 7,027,863 B1 | 4/2006 | Prutchi et al. |
| 7,062,318 B2 | 6/2006 | Ben-Haim et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,412,289 B2 | 8/2008 | Malonek et al. |
| 7,460,907 B1 | 12/2008 | Darvish et al. |
| 7,840,262 B2 | 11/2010 | Mika et al. |
| 7,840,263 B2 | 11/2010 | Girouard et al. |
| 8,326,416 B2 | 12/2012 | Mika et al. |
| 8,958,872 B2 | 2/2015 | Ben-Haim et al. |
| 2002/0010492 A1 | 1/2002 | Donovan et al. |
| 2002/0026141 A1 | 2/2002 | Houben et al. |
| 2002/0052632 A1 | 5/2002 | Ben-Haim et al. |
| 2002/0065455 A1 | 5/2002 | Ben-Haim et al. |
| 2002/0183682 A1 | 5/2002 | Darvish et al. |
| 2002/0183686 A1 | 5/2002 | Darvish et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0055464 A1 | 3/2003 | Darvish et al. |
| 2003/0100889 A1 | 5/2003 | Duverger et al. |
| 2003/0208242 A1 | 6/2003 | Harel et al. |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0211475 A1 | 11/2003 | Roberts |
| 2004/0059393 A1 | 3/2004 | Policker et al. |
| 2004/0106954 A1 | 3/2004 | Whitehurst et al. |
| 2004/0095333 A1 | 5/2004 | Morag et al. |
| 2004/0105040 A1 | 6/2004 | Oh et al. |
| 2004/0138710 A1 | 7/2004 | Shemer et al. |
| 2004/0155871 A1 | 8/2004 | Perski et al. |
| 2004/0158289 A1 | 8/2004 | Girouard et al. |
| 2004/0172079 A1 | 9/2004 | Chinchoy |
| 2004/0193231 A1 | 9/2004 | David et al. |
| 2004/0230273 A1 | 11/2004 | Cates et al. |
| 2004/0243190 A1 | 12/2004 | Ben-Haim et al. |
| 2004/0249421 A1 | 12/2004 | Harel et al. |
| 2005/0192542 A1 | 1/2005 | Dev et al. |
| 2005/0033396 A1 | 2/2005 | Ospyka |
| 2005/0095227 A1 * | 5/2005 | Rosenzweig .......... C07K 14/47 424/93.2 |
| 2005/0267542 A1 | 12/2005 | David et al. |
| 2005/0277993 A1 | 12/2005 | Mower |
| 2006/0036126 A1 | 2/2006 | Ross et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0027487 A1 | 2/2007 | Mika et al. |
| 2007/0027490 A1 | 2/2007 | Ben-Haim et al. |
| 2007/0088393 A1 | 4/2007 | Ben-Haim et al. |
| 2007/0156177 A1 | 7/2007 | Harel et al. |
| 2007/0162079 A1 | 7/2007 | Shemer et al. |
| 2007/0171211 A1 | 7/2007 | Perski et al. |
| 2007/0293901 A1 | 12/2007 | Rousso et al. |

(56) References Cited

U.S. PATENT DOCUMENTS

| | | | |
|---|---|---|---|
| 2008/0058879 A1 | 3/2008 | Ben-Haim et al. | |
| 2008/0065159 A1 | 3/2008 | Ben-Haim et al. | |
| 2008/0065163 A1 | 3/2008 | Ben-Haim et al. | |
| 2008/0065164 A1 | 3/2008 | Ben-Haim et al. | |
| 2008/0140142 A1 | 6/2008 | Darvish et al. | |
| 2009/0062893 A1 | 3/2009 | Spehr et al. | |
| 2009/0280103 A1* | 11/2009 | Flueck | A61K 38/39 424/94.5 |
| 2009/0292324 A1 | 11/2009 | Rousso et al. | |
| 2010/0016923 A1 | 1/2010 | Rousso et al. | |
| 2010/0035963 A1 | 2/2010 | Chajut et al. | |
| 2010/0269180 A1* | 10/2010 | Ranscht | C07K 14/5759 800/3 |
| 2013/0096639 A1 | 4/2013 | Ben-Haim et al. | |
| 2013/0338425 A1 | 12/2013 | Rousso et al. | |
| 2014/0236250 A1 | 8/2014 | Ben-Haim et al. | |
| 2015/0157857 A1 | 6/2015 | Ben-Haim et al. | |
| 2015/0174404 A1 | 6/2015 | Rousso et al. | |
| 2016/0136418 A1 | 5/2016 | Ben-Haim et al. | |
| 2016/0370384 A1 | 12/2016 | Rousso et al. | |
| 2019/0137513 A1 | 5/2019 | Rousso et al. | |
| 2022/0062631 A1 | 3/2022 | Rousso et al. | |

FOREIGN PATENT DOCUMENTS

| | | | |
|---|---|---|---|
| EP | 0250931 | 1/1988 | |
| EP | 0314078 | 5/1989 | |
| EP | 0481684 | 4/1992 | |
| EP | 0503839 | 9/1992 | |
| EP | 0528751 | 2/1993 | |
| EP | 0220916 | 4/1994 | |
| EP | 0727241 | 8/1996 | |
| EP | 1263498 | 12/2002 | |
| EP | 0910429 | 3/2005 | |
| GB | 1394171 | 5/1975 | |
| GB | 2280377 | 2/1995 | |
| JP | 62-112530 | 5/1987 | |
| JP | 62-275471 | 11/1987 | |
| JP | 04-117967 | 4/1992 | |
| JP | 04-282168 | 10/1992 | |
| JP | 04-365493 | 12/1992 | |
| JP | 06-169998 | 6/1994 | |
| JP | 06-506619 | 7/1994 | |
| JP | 07-126600 | 5/1995 | |
| JP | 07-144024 | 6/1995 | |
| JP | 08-243176 | 9/1996 | |
| JP | 2003512884 A * | 4/2003 | A61B 17/3203 |
| RU | 386634 | 6/1973 | |
| RU | 553977 | 5/1977 | |
| RU | 831131 | 5/1981 | |
| RU | 2014844 | 6/1994 | |
| RU | 2055606 | 3/1996 | |
| RU | 2075980 | 3/1997 | |
| RU | 2077273 | 4/1997 | |
| RU | 2078547 | 5/1997 | |
| WO | WO 91/19534 | 12/1991 | |
| WO | WO 92/00716 | 1/1992 | |
| WO | WO 92/13592 | 8/1992 | |
| WO | WO 93/02743 | 2/1993 | |
| WO | WO 93/02745 | 2/1993 | |
| WO | WO 93/08874 | 5/1993 | |
| WO | WO 93/18820 | 9/1993 | |
| WO | WO 94/17855 | 8/1994 | |
| WO | WO 95/08316 | 3/1995 | |
| WO | WO 96/05768 | 2/1996 | |
| WO | WO 96/10358 | 4/1996 | |
| WO | WO 96/16696 | 6/1996 | |
| WO | WO 97/15227 | 1/1997 | |
| WO | WO 97/06849 | 2/1997 | |
| WO | WO 97/24983 | 7/1997 | |
| WO | WO 97/25098 | 7/1997 | |
| WO | WO 97/25101 | 7/1997 | |
| WO | WO 97/26042 | 7/1997 | |
| WO | WO 97/27900 | 7/1997 | |
| WO | WO 97/29682 | 8/1997 | |
| WO | WO 97/29684 | 8/1997 | |
| WO | WO 97/29700 | 8/1997 | |
| WO | WO 97/29701 | 8/1997 | |
| WO | WO 97/29709 | 8/1997 | |
| WO | WO 98/10828 | 3/1998 | |
| WO | WO 98/10829 | 3/1998 | |
| WO | WO 98/10830 | 3/1998 | |
| WO | WO 98/10831 | 3/1998 | |
| WO | WO 98/10832 | 3/1998 | |
| WO | WO 98/11840 | 3/1998 | |
| WO | WO 98/15317 | 4/1998 | |
| WO | WO 98/19719 | 5/1998 | |
| WO | WO 98/56378 | 12/1998 | |
| WO | WO 98/57701 | 12/1998 | |
| WO | WO 99/06105 | 2/1999 | |
| WO | WO 99/09971 | 3/1999 | |
| WO | WO 99/55360 | 4/1999 | |
| WO | WO 99/24110 | 5/1999 | |
| WO | WO 99/29307 | 6/1999 | |
| WO | WO 99/59548 | 11/1999 | |
| WO | WO 00/01443 | 1/2000 | |
| WO | WO 00/04947 | 2/2000 | |
| WO | WO 00/16741 | 3/2000 | |
| WO | WO 00/27475 | 5/2000 | |
| WO | WO 00/27476 | 5/2000 | |
| WO | WO 00/42914 | 7/2000 | |
| WO | WO 00/12525 | 9/2000 | |
| WO | WO 00/53257 | 9/2000 | |
| WO | WO 00/74773 | 12/2000 | |
| WO | WO 01/24871 | 4/2001 | |
| WO | WO 01/30139 | 5/2001 | |
| WO | WO 01/30445 | 5/2001 | |
| WO | WO 01/49367 | 7/2001 | |
| WO | WO 01/52931 | 7/2001 | |
| WO | WO 01/66183 | 9/2001 | |
| WO | WO 01/82771 | 11/2001 | |
| WO | WO 01/91854 | 12/2001 | |
| WO | WO 01/93950 | 12/2001 | |
| WO | WO 01/93951 | 12/2001 | |
| WO | WO 02/10791 | 2/2002 | |
| WO | WO 02/053093 | 7/2002 | |
| WO | WO 02/082968 | 10/2002 | |
| WO | WO 03/045493 | 5/2003 | |
| WO | WO 2004/059393 | 7/2004 | |
| WO | WO 2004/070396 | 8/2004 | |
| WO | WO 2004/080533 | 9/2004 | |
| WO | WO 2005/023081 | 3/2005 | |
| WO | WO 2005/087310 | 9/2005 | |
| WO | WO 2005/114369 | 12/2005 | |
| WO | WO 2006/073671 | 7/2006 | |
| WO | WO 2006/087717 | 8/2006 | |
| WO | WO 2006/097934 | 9/2006 | |
| WO | WO 2006/097935 | 9/2006 | |
| WO | WO 2006/119467 | 9/2006 | |

OTHER PUBLICATIONS

Bers "Excitation-Contracting Coupling", Excitation-Contraction Coupling and Cardiac Contractile Force, 2nd Ed., Chap.8: 203-407, 2001. (Part II: pp. 283-355).

Bers "Excitation-Contracting Coupling", Excitation-Contraction Coupling and Cardiac Contractile Force, 2nd Ed., Chap.8: 203-407, 2001. (Part III: 356-407).

U.S. Appl. No. 90/008,688, filed Jun. 15, 2007, Ben Haim.

U.S. Appl. No. 90/008,707, filed Jun. 7, 2007, Ben Haim.

Advisory Action Before the Filing of An Appeal Brief dated May 9, 2013 From the U.S. Patent and Trademark Office Re. U.S. Appl. No. 11/673,812.

Advisory Action Before the Filing of An Appeal Brief dated Mar. 22, 2012 From the U.S. Patent and Trademark Office Re. U.S. Appl. No. 11/886,154.

Amended Request for Ex Parte Reexamination of U.S. Pat. No. 6,317,631 dated Aug. 20, 2007 From the U.S. Patent and Trademark Office Re. U.S. Appl. No. 90/008,689.

Applicant-Initiated Interview Summary dated Apr. 11, 2013 From the U.S. Patent and Trademark Office Re. U.S. Appl. No. 11/673,812.

(56) References Cited

OTHER PUBLICATIONS

Applicant-Initiated Interview Summary dated Dec. 11, 2013 From the U.S. Patent and Trademark Office Re. U.S. Appl. No. 13/970,647.
Applicant-Initiated Interview Summary dated Dec. 13, 2013 From the U.S. Patent and Trademark Office Re. U.S. Appl. No. 10/116,201.
Applicant-Initiated Interview Summary dated Jul. 14, 2017 From the U.S. Patent and Trademark Office Re. U.S. Appl. No. 11/792,811. (3 Pages).
Applicant-Initiated Interview Summary dated Sep. 15, 2017 From the U.S. Patent and Trademark Office Re. U.S. Appl. No. 15/249,506. (3 pages).
Applicant-Initiated Interview Summary dated Apr. 23, 2015 From the U.S. Patent and Trademark Office Re. U.S. Appl. No. 11/673,812.
Applicant-Initiated Interview Summary dated Nov. 28, 2012 From the U.S. Patent and Trademark Office Re. U.S. Appl. No. 11/919,491.
Brief Communication: Oral Proceedings on Jan. 12, 2016 dated Dec. 17, 2015 From the European Search Report Re. Application No. 06759102.4.
Communication Pursuant to Article 94(3) EPC dated Mar. 2, 2009 From the European Patent Office Re. Application No. 05853465.2.
Communication Pursuant to Article 94(3) EPC dated Jun. 5, 2014 From the European Patent Office Re. Application No. 04719312.3.
Communication Pursuant to Article 94(3) EPC dated Nov. 10, 2015 From the European Patent Office Re. Application No. 01928181.5.
Communication Pursuant to Article 94(3) EPC dated Aug. 11, 2010 From the European Patent Office Re. Application No. 99931435.4.
Communication Pursuant to Article 94(3) EPC dated Nov. 11, 2015 From the European Patent Office Re. Application No. 04106247.2.
Communication Pursuant to Article 94(3) EPC dated Sep. 12, 2014 From the European Patent Office Re. Application No. 05853465.2.
Communication Pursuant to Article 94(3) EPC dated Jun. 17, 2008 From the European Patent Office Re. Application No. 01928181.5.
Communication Pursuant to Article 94(3) EPC dated Aug. 26, 2011 From the European Patent Office Re. Application No. 05853465.2.
Communication Pursuant to Article 94(3) EPC dated Aug. 26, 2011 From the European Patent Office Re. Application No. 06759102.4.
Communication Pursuant to Article 94(3) EPC dated Jan. 29, 2009 From the European Patent Office Re. Application No. 04106247.2.
Communication Pursuant to Article 96(2) EPC dated Mar. 2, 2007 From the European Patent Office Re. Application No. 97929478.2.
Communication to Pursuant to Article 94(3) EPC dated Mar. 4, 2009 From the European Search Report Re. Application No. 06759102.4.
Communication to Pursuant to Article 94(3) EPC dated Sep. 12, 2014 From the European Search Report Re. Application No. 06759102.4.
Examination Report dted Jan. 9, 2014 From the Government of India, Patent Office, Intellectual Property Building Re. Application No. 5571/CHENP/2007.
Examination Report dated Sep. 17, 2013 From the Government of India, Patent Office, Intellectual Property Building Re. Application No. 5571/CHENP/2007.
Examination Report dated Feb. 20, 2013 From the Government of India, Patent Office, Intellectual Property Building Re. Application No. 5571/CHENP/2007.
Examination Report dated Feb. 27, 2013 From the Government of India, Patent Office, Intellectual Property Building Re. Application No. 2014/CHENP/2008.
Examination Report dated Dec. 30, 2013 From the Government of India, Patent Office, Intellectual Property Building Re. Application No. 5571/CHENP/2007.
Hearing Notice dated Aug. 3, 2017 From the Government of India, Patent Office, Intellectual Property Building Re. Application No. 2014/CHENP/2008. (2 Pages).
Hearing Notice in Reference of Application 5571/CHENP/2007 dated Nov. 25, 2014 From the Government of India, Patent Office, Intellectual Property Building Re. Application No. 5571/CHENP/2007.
Hearing Notice in Reference of Application No. 5571/CHF.NP/2007 dated Mar. 6, 2014 From the Government of India, Patent Office, Intellectual Property Building Re. Application No. 5571/CHENP/2007.
Inter Partes Reexamination Communication of Patent U.S. Pat. No. 6,330,476 dated Sep. 4, 2007 From the US Patent and Trademark Office Re.: U.S. Appl. No. 95/000,032.
International Preliminary Report on Patentability dated Nov. 15, 2007 From the International Bureau of WIPO Re. Application No. PCT/US2006/017281.
International Preliminary Report on Patentability dated Jun. 21, 2007 From the International Bureau of WIPO Re. Application No. PCT/US2005/044557.
International Preliminary Report on Patentability dated Sep. 27, 2007 From the International Bureau of WIPO Re. Application No. PCT/IL2006/000345.
International Search Report and the Written Opinion dated May 12, 2006 From the International Searching Authority Re. Application No. PCT/US05/44557.
International Search Report and the Written Opinion dated Oct. 16, 2006 From the International Searching Authority Re. Application No. PCT/US06/17281.
Invitation Pursuant to Rule 62a(1) EPC and Rule 63(1) EPC dated May 5, 2010 From the European Patent Office Re. Application No. 04719312.3.
Notice of Non-Compliant Amendment dated Jun. 1, 2011 From the U.S. Patent and Trademark Office Re. U.S. Appl. No. 11/886,154.
Notice of Non-Compliant Amendment dated Dec. 12, 2011 From the U.S. Patent and Trademark Office Re. U.S. Appl. No. 11/792,811.
Notice of Non-Compliant Amendment dated Jul. 15, 2011 From the U.S. Patent and Trademark Office Re. U.S. Appl. No. 11/886,154.
Notice of Non-Compliant Amendment dated Jun. 17, 2013 From the U.S. Patent and Trademark Office Re. U.S. Appl. No. 10/039,845.
Notice of Non-Compliant Amendment dated Mar. 23, 2017 From the U.S. Patent and Trademark Office Re. Application No. 11/792,811. (3 pages).
Notification of Non-Compliant Appeal Brief (37 CFR 41.37) dated Sep. 23, 2014 From the U.S. Patent and Trademark Office Re. U.S. Appl. No. 10/039,845.
Notification of Reexamination dated Apr. 4, 2014 From the State Intellectual Property Office of the People's Republic of China Re. Application No. 200480012687.5 and Its Translation Into English.
Office Action dated Jan. 8, 2010 From the State Intellectual Property Office (SIPO) of the People's Republic of China Re.: Application No. 200480012687.5 and Its Translation Into English.
Office Action dated Oct. 12, 2004 From the Israeli Patent Office Re. Application No. 128955.
Office Action dated Jul. 13, 2009 From the State Intellectual Property Office of the People s Republic of China Re. Application No. 200480027283.3 and Its Translation Into English.
Office Action dated Dec. 15, 2008 From the State Intellectual Property Office (SIPO) of the People's Republic of China Re. Application No. 200480012687.5 and Its Translation Into English.
Office Action dated Jan. 18, 2012 From the State Intellectual Property Office (SIPO) of the People's Republic of China Re. Application No. 200480012687.5 and Its Translation Into English.
Office Action dated Oct. 21, 2014 From the State Intellectual Property Office (SIPO) of the People's Republic of China Re. Application No. 200480012687.5 and Its Translation Into English.
Office Action dated Nov. 25, 2010 From the State Intellectual Property Office (SIPO) of the People's Republic of China Re. Application No. 200480012687.5 and Its Translation Into English.
Office Action dated Apr. 30, 2015 From the State Intellectual Property Office (SIPO) of the People's Republic of China Re. Application No. 200480012687.5 and Its Translation Into English.
Official Action dated Aug. 1, 2007 From the U.S. Patent and Trademark Office Re. U.S. Appl. No. 90/008,312.
Official Action dated Jul. 1, 2014 From the U.S. Patent and Trademark Office Re. U.S. Appl. No. 10/116,201.
Official Action dated Jun. 1, 2009 From the U.S. Patent and Trademark Office Re. U.S. Appl. No. 10/039,845.
Official Action dated Dec. 2, 2009 From the U.S. Patent and Trademark Office Re. U.S. Appl. No. 11/932,149.

(56) References Cited

OTHER PUBLICATIONS

Official Action dated Jun. 2, 2016 From the U.S. Patent and Trademark Office Re. U.S. Appl. No. 11/673,812.
Official Action dated Jan. 3, 2011 From the U.S. Patent and Trademark Office Re. U.S. Appl. No. 11/932,149.
Official Action dated Jul. 3, 2012 From the U.S. Patent and Trademark Office Re. U.S. Appl. No. 12/910,943.
Official Action dated Nov. 3, 2009 From the U.S. Patent and Trademark Office Re. U.S. Appl. No. 11/931,724.
Official Action dated Feb. 4, 2010 From the U.S. Patent and Trademark Office Re. U.S. Appl. No. 10/039,845.
Official Action dated Jan. 4, 2012 From the U.S. Patent and Trademark Office Re. U.S. Appl. No. 11/673,812.
Official Action dated Dec. 5, 2008 From the U.S. Patent and Trademark Office Re. U.S. Appl. No. 11/550,560.
Official Action dated Jan. 5, 2010 From the U.S. Patent and Trademark Office Re. U.S. Appl. No. 11/802,685.
Official Action dated Nov. 5, 2009 From the U.S. Patent and Trademark Office Re. U.S. Appl. No. 10/549,216.
Official Action dated Oct. 5, 2010 From the U.S. Patent and Trademark Office Re. U.S. Appl. No. 10/039,845.
Official Action dated Jan. 6, 2010 From the U.S. Patent and Trademark Office Re. U.S. Appl. No. 11/933,168.
Official Action dated Jan. 6, 2011 From the U.S. Patent and Trademark Office Re. U.S. Appl. No. 11/931,724.
Official Action dated Jan. 6, 2012 From the U.S. Patent and Trademark Office Re. U.S. Appl. No. 11/933,168.
Official Action dated Mar. 6, 2009 From the U.S. Patent and Trademark Office Re. U.S. Appl. No. 11/931,889.
Official Action dated Mar. 6, 2009 From the U.S. Patent and Trademark Office Re. U.S. Appl. No. 11/932,064.
Official Action dated Oct. 6, 2009 From the U.S. Patent and Trademark Office Re. U.S. Appl. No. 11/550,560.
Official Action dated Jun. 8, 2017 From the U.S. Patent and Trademark Office Re. U.S. Appl. No. 11/792,811. (15 pages).
Official Action dated Nov. 8, 2011 From the U.S. Patent and Trademark Office Re. U.S. Appl. No. 11/931,889.
Official Action dated Oct. 8, 2009 From the U.S. Patent and Trademark Office Re. U.S. Appl. No. 10/116,201.
Official Action dated Aug. 9, 2011 From the U.S. Patent and Trademark Office Re. U.S. Appl. No. 11/932,149.
Official Action dated Oct. 10, 2008 From the U.S. Patent and Trademark Office Re. U.S. Appl. No. 09/980,748.
Official Action dated Sep. 10, 2013 From the U.S. Patent and Trademark Office Re. U.S. Appl. No. 10/039,845.
Official Action dated Jun. 11, 2010 From the U.S. Patent and Trademark Office Re. U.S. Appl. No. 11/550,560.
Official Action dated Jun. 11, 2010 From the U.S. Patent and Trademark Office Re. U.S. Appl. No. 11/932,064.
Official Action dated Oct. 11, 2011 From the U.S. Patent and Trademark Office Re. U.S. Appl. No. 11/919,491.
Official Action dated Sep. 11, 2009 From the U.S. Patent and Trademark Office Re. U.S. Appl. No. 09/980,748.
Official Action dated May 12, 2011 From the U.S. Patent and Trademark Office Re. U.S. Appl. No. 10/039,845.
Official Action dated Sep. 12, 2008 From the U.S. Patent and Trademark Office Re. U.S. Appl. No. 10/039,845.
Official Action dated Jan. 13, 2011 From the U.S. Patent and Trademark Office Re. U.S. Appl. No. 11/931,889.
Official Action dated May 13, 2011 From the U.S. Patent and Trademark Office Re. U.S. Appl. No. 11/933,168.
Official Action dated Oct. 13, 2010 From the U.S. Patent and Trademark Office Re. U.S. Appl. No. 11/919,491.
Official Action dated Apr. 14, 2011 From the U.S. Patent and Trademark Office Re. U.S. Appl. No. 11/932,149.
Official Action dated Jan. 14, 2014 From the U.S. Patent and Trademark Office Re. U.S. Appl. No. 10/039,845.
Official Action dated Jul. 14, 2017 From the U.S. Patent and Trademark Office Re. U.S. Appl. No. 15/249,506. (330 Pages).
Official Action dated Sep. 14, 2009 From the U.S. Patent and Trademark Office Re. U.S. Appl. No. 11/931,889.
Official Action dated Sep. 14, 2011 From the U.S. Patent and Trademark Office Re. U.S. Appl. No. 11/886,154.
Official Action dated Apr. 15, 2014 From the U.S. Patent and Trademark Office Re. U.S. Appl. No. 13/970,647.
Official Action dated Dec. 15, 2011 From the U.S. Patent and Trademark Office Re. U.S. Appl. No. 12/910,943.
Official Action dated Feb. 15, 2012 From the U.S. Patent and Trademark Office Re. U.S. Appl. No. 11/802,685.
Official Action dated Jan. 15, 2015 From the U.S. Patent and Trademark Office Re. U.S. Appl. No. 11/673,812.
Official Action dated Jul. 15, 2008 From the U.S. Patent and Trademark Office Re. U.S. Appl. No. 10/116,201.
Official Action dated Sep. 15, 2016 From the U.S. Patent and Trademark Office Re. U.S. Appl. No. 14/941,790.
Official Action dated Oct. 16, 2013 From the U.S. Patent and Trademark Office Re. U.S. Appl. No. 13/970,647.
Official Action dated Feb. 17, 2012 From the U.S. Patent and Trademark Office Re. U.S. Appl. No. 11/932,149.
Official Action dated Jun. 17, 2010 From the U.S. Patent and Trademark Office Re. U.S. Appl. No. 10/549,216.
Official Action dated Jan. 18, 2012 From the U.S. Patent and Trademark Office Re. U.S. Appl. No. 11/886,154.
Official Action dated Jul. 18, 2007 From the U.S. Patent and Trademark Office Re. U.S. Appl. No. 10/039,845.
Official Action dated Sep. 19, 2016 From the U.S. Patent and Trademark Office Re. U.S. Appl. No. 11/792,811.
Official Action dated Dec. 20, 2011 From the U.S. Patent and Trademark Office Re. U.S. Appl. No. 10/039,845.
Official Action dated Dec. 21, 2012 From the U.S. Patent and Trademark Office Re. U.S. Appl. No. 11/673,812.
Official Action dated Feb. 21, 2012 From the U.S. Patent and Trademark Office Re. U.S. Appl. No. 10/116,201.
Official Action dated Jul. 21, 2010 From the U.S. Patent and Trademark Office Re. U.S. Appl. No. 11/802,685.
Official Action dated May 21, 2007 From the U.S. Patent and Trademark Office Re. U.S. Appl. No. 09/980,748.
Official Action dated May 21, 2010 From the U.S. Patent and Trademark Office Re. U.S. Appl. No. 10/116,201.
Official Action dated Mar. 22, 2011 From the U.S. Patent and Trademark Office Re. U.S. Appl. No. 11/886,154.
Official Action dated Dec. 23, 2010 From the U.S. Patent and Trademark Office Re. U.S. Appl. No. 09/980,748.
Official Action dated Jun. 23, 2009 From the U.S. Patent and Trademark Office Re. U.S. Appl. No. 10/549,216.
Official Action dated Jan. 24, 2011 From the U.S. Patent and Trademark Office Re. U.S. Appl. No. 11/919,491.
Official Action dated Jun. 26, 2008 From the U.S. Patent and Trademark Office Re. U.S. Appl. No. 11/536,794.
Official Action dated Oct. 26, 2017 From the U.S. Patent and Trademark Office Re. U.S. Appl. No. 15/249,506. (12 pages).
Official Action dated Aug. 27, 2012 From the U.S. Patent and Trademark Office Re. U.S. Appl. No. 11/919,491.
Official Action dated Aug. 27, 2015 From the U.S. Patent and Trademark Office Re. U.S. Appl. No. 11/673,812.
Official Action dated Apr. 28, 2011 From the U.S. Patent and Trademark Office Re. U.S. Appl. No. 11/931,889.
Official Action dated Apr. 28, 2015 From the U.S. Patent and Trademark Office Re. U.S. Appl. No. 14/621,988.
Official Action dated Aug. 28, 2009 From the U.S. Patent and Trademark Office Re. U.S. Appl. No. 11/802,685.
Official Action dated Aug. 28, 2009 From the U.S. Patent and Trademark Office Re. U.S. Appl. No. 11/932,064.
Official Action dated Feb. 28, 2008 From the U.S. Patent and Trademark Office Re. U.S. Appl. No. 09/980,748.
Official Action dated Jun. 28, 2010 From the U.S. Patent and Trademark Office Re. U.S. Appl. No. 11/931,889.
Official Action dated Apr. 29, 2009 From the U.S. Patent and Trademark Office Re. U.S. Appl. No. 09/980,748.
Official Action dated Jul. 29, 2013 From the U.S. Patent and Trademark Office Re. U.S. Appl. No. 10/116,201.

(56) References Cited

OTHER PUBLICATIONS

Official Action dated May 29, 2013 From the U.S. Patent and Trademark Office Re. U.S. Appl. No. 13/662,775.
Official Action dated Sep. 29, 2010 From the U.S. Patent and Trademark Office Re. U.S. Appl. No. 11/933,168.
Official Action dated Apr. 30, 2010 From the U.S. Patent and Trademark Office Re. U.S. Appl. No. 11/931,724.
Official Action dated Apr. 30, 2010 From the U.S. Patent and Trademark Office Re. U.S. Appl. No. 11/932,149.
Official Action dated Aug. 30, 2006 From the U.S. Patent and Trademark Office Re. U.S. Appl. No. 09/980,748.
Official Action dated Aug. 31, 2007 From the U.S. Patent and Trademark Office Re. U.S. Appl. No. 11/536,794.
Official Action dated Aug. 31, 2010 From the U.S. Patent and Trademark Office Re. U.S. Appl. No. 11/550,560.
Official Action dated Mar. 31, 2011 From the U.S. Patent and Trademark Office Re. U.S. Appl. No. 11/673,812.
Pre-Appeal Brief Request for Review dated Aug. 9, 2011 From the U.S. Patent and Trademark Office Re. U.S. Appl. No. 11/933,168.
Provision of A Copy of the Minutes in Accordance With Rule 124(4) EPC dated May 23, 2017 From the European Patent Office Re. Application No. 01928181.5. (7 Pages).
Request for Ex Parte Reexamination of U.S. Pat. No. 6,363,279—IDS Submitted Dec. 31, 2007 From the U.S. Patent and Trademark Office Re.: U.S. Appl. No. 90/008,688.
Request for Ex Parte Reexamination of U.S. Pat. No. 6,363,279—Notice of Intent to Issue Reexamination Certificate dated Mar. 18, 2009 From the U.S. Patent and Trademark Office Re.: U.S. Appl. No. 90/008,688.
Request for Ex Parte Reexamination of U.S. Pat. No. 6,363,279—Official Action dated Jun. 20, 2008 From the U.S. Patent and Trademark Office Re.: U.S. Appl. No. 90/008,688.
Request for Ex Parte Reexamination of U.S. Pat. No. 6,363,279—Order Granting Request dated Nov. 5, 2007 From the U.S. Patent and Trademark Office Re.: U.S. Appl. No. 90/008,688.
Request for Ex Parte Reexamination of U.S. Pat. No. 6,363,279 dated Jun. 8, 2007 From the U.S. Patent and Trademark Office Re.: U.S. Appl. No. 90/008,688.
Request for Ex Parte Reexamination of U.S. Pat. No. 6,363,279, Response to Official Action dated Jun. 20, 2008 Submitted Aug. 20, 2008 From the U.S. Patent and Trademark Office Re.: U.S. Appl. No. 90/008,688.
Request for Ex Parte Reexamination of U.S. Pat. No. 6,236,887—IDS Submitted Oct. 17, 2007 From the U.S. Patent and Trademark Office Re.: U.S. Appl. No. 90/008,707.
Request for Ex Parte Reexamination of U.S. Pat. No. 6,236,887—IDS Submitted Sep. 29, 2008 From the U.S. Patent and Trademark Office Re.: U.S. Appl. No. 90/008,707.
Request for Ex Parte Reexamination of U.S. Pat. No. 6,236,887—Notice of Intent to Issue Ex Parte Examination Certificate dated Mar. 19, 2009 From the U.S. Patent and Trademark Office Re.: U.S. Appl. No. 90/008,707.
Request for Ex Parte Reexamination of U.S. Pat. No. 6,236,887—Official Action and IDS Considered dated Jun. 20, 2008 From the U.S. Patent and Trademark Office Re.: U.S. Appl. No. 90/008,707.
Request for Ex Parte Reexamination of U.S. Pat. No. 6,236,887—Official Action Granting Request for Ex Parte Examination dated Aug. 17, 2007 From the U.S. Patent and Trademark Office Re.: U.S. Appl. No. 90/008,707.
Request for Ex Parte Reexamination of U.S. Pat. No. 6,236,887 dated Jun. 13, 2007 From the U.S. Patent and Trademark Office Re.: U.S. Appl. No. 90/008,707.
Request for Ex Parte Reexamination of U.S. Pat. No. 6,298,268—Certificate of Reexamination dated Mar. 7, 2006, U.S. Appl. No. 90/006,788.
Request for Ex Parte Reexamination of U.S. Pat. No. 6,298,268—IDS Considered dated Feb. 22, 2005, U.S. Appl. No. 90/006,788.
Request for Ex Parte Reexamination of U.S. Pat. No. 6,298,268—Notice of Intent to Issue Certificate of Reexamination dated Mar. 29, 2005, U.S. Appl. No. 90/006,788.
Request for Ex Parte Reexamination of U.S. Pat. No. 6,298,268 dated Oct. 10, 2003, U.S. Appl. No. 90/006,788.
Request for Ex Parte Reexamination of U.S. Pat. No. 6,298,268 Order Granting Request for Ex Parte Reexamination Dated Dec. 19, 2003, U.S. Appl. No. 90/006,788.
Request for Ex Parte Reexamination of U.S. Pat. No. 6,317,631—Amendment in Response to Official Action dated Jun. 20, 2008, Filed Aug. 20, 2008 From the U.S. Patent and Trademark Office Re.: U.S. Appl. No. 90/008,689.
Request for Ex Parte Reexamination of U.S. Pat. No. 6,317,631—IDS Dated Sep. 26, 2008 From the U.S. Patent and Trademark Office Re.: U.S. Appl. No. 90/008,689.
Request for Ex Parte Reexamination of U.S. Pat. No. 6,317,631—IDS Dated Dec. 31, 2007 From the U.S. Patent and Trademark Office Re.: U.S. Appl. No. 90/008,689.
Request for Ex Parte Reexamination of U.S. Pat. No. 6,317,631—Notice of Intent to Issue Certificate of Reexamination dated Mar. 18, 2009 From the U.S. Patent and Trademark Office Re.: U.S. Appl. No. 90/008,689.
Request for Ex Parte Reexamination of U.S. Pat. No. 6,317,631—Official Action dated Jun. 20, 2008, U.S. Appl. No. 90/008,689.
Request for Ex Parte Reexamination of U.S. Pat. No. 6,317,631—Order Granting Reexamination dated Nov. 5, 2007, U.S. Appl. No. 90/008,689.
Request for Ex Parte Reexamination of U.S. Pat. No. 6,317,631—IDS dated Jun. 8, 2007, U.S. Appl. No. 90/008,689.
Request for Ex Parte Reexamination of U.S. Pat. No. 6,330,476—IDS dated May 31, 2006.
Request for Ex Parte Reexamination of U.S. Pat. No. 6,330,476—Comments by 3rd Party Requestor, Response Thereto and Official Action dated Jul. 16, 2008, U.S. Appl. No. 95/000,032.
Request for Ex Parte Reexamination of U.S. Pat. No. 6,330,476—Communication of Right to Appeal dated Jul. 16, 2008, Re. U.S. Appl. No. 95/000,032.
Request for Ex Parte Reexamination of U.S. Pat. No. 6,330,476—IDS Filed May 4, 2007 Re. U.S. Appl. No. 95/000,032.
Request for Ex Parte Reexamination of U.S. Pat. No. 6,330,476—Official Action by USPTO dated Mar. 23, 2004, U.S. Appl. No. 95/000,032.
Request for Ex Parte Reexamination of U.S. Pat. No. 6,330,476—Order Granting Request for Reexamination dated Mar. 23, 2004 From the U.S. Patent and Trademark Office Re.: U.S. Appl. No. 95/000,032.
Request for Ex Parte Reexamination of U.S. Pat. No. 6,330,476 dated Dec. 31, 2003 From the U.S. Patent and Trademark Office Re.: U.S. Appl. No. 95/000,032.
Request for Ex Parte Reexamination of U.S. Pat. No. 6,463,324—Amendment in Response to Official Action dated Aug. 1, 2007 Filed Oct. 1, 2007 From the U.S. Patent and Trademark Office Re.: U.S. Appl. No. 90/008,312.
Request for Ex Parte Reexamination of U.S. Pat. No. 6,463,324—Certificate of Reexamination dated Apr. 29, 2008 From the U.S. Patent and Trademark Office Re.: U.S. Appl. No. 90/008,312.
Request for Ex Parte Reexamination of U.S. Pat. No. 6,463,324—Official Action—Notice of Intent to Reexamine dated Jan. 24, 2008 From the U.S. Patent and Trademark Office Re.: U.S. Appl. No. 90/008,312.
Request for Ex Parte Reexamination of U.S. Pat. No. 6,463,324—Official Action dated Aug. 1, 2007 From the U.S. Patent and Trademark Office Re.: U.S. Appl. No. 90/008,312.
Request for Ex Parte Reexamination of U.S. Pat. No. 6,463,324—Official Action, Interview Summary and References Considered dated Nov. 6, 2007 From the U.S. Patent and Trademark Office Re.: U.S. Appl. No. 90/008,312.
Request for Ex Parte Reexamination of U.S. Pat. No. 6,463,324 Dated Nov. 1, 2006 From the U.S. Patent and Trademark Office Re.: U.S. Appl. No. 90/008,312.
Restriction Official Action dated Mar. 17, 2016 From the U.S. Patent and Trademark Office Re. U.S. Appl. No. 11/792,811.
Summons to Attend Oral Proceedings Pursuant to Rule 115(1) EPC dated May 8, 2015 From the European Search Report Re. Application No. 06759102.4.

(56) References Cited

OTHER PUBLICATIONS

Summons to Attend Oral Proceedings Pursuant to Rule 115(1) EPC dated Dec. 22, 2008 From the European Patent Office Re.: Application No. 97929480.8.
Summons to Attend Oral Proceedings Pursuant to Rule 115(1) EPC Dated Jun. 22, 2015 From the European Patent Office Re. Application No. 05853465.2.
Summons to Attend Oral Proceedings Pursuant to Rule 115(1) EPC Dated Dec. 23, 2016 From the European Patent Office Re. Application No. 01928181.5. (2 Pages).
Summons to Attend Oral Proceedings Pursuant to Rule 115(1) EPC Dated Sep. 26, 2016 From the European Patent Office Re. Application No. 01928181.5.
Supplementary European Search Report and the European Search Opinion dated Nov. 28, 2008 From the European Patent Office Re. Application No. 05853465.2.
Supplementary European Search Report and the European Search Opinion dated Nov. 28, 2008 From the European Patent Office Re.: Application No. 006759102.4.
Supplementary Partial European Search Report dated Nov. 4, 2010 From the European Patent Office Re. Application No. 04719312.3.
Supplementary Partial European Search Report dated Sep. 6, 2006 From the European Patent Office Re. Application No. 01928181.5.
Translation of Notice of Reasons for Rejection dated Jul. 18, 2006 From the Japanese Patent Office Re. Application No. 09-529637.
Translation of Notice of Reasons for Rejection dated Apr. 27, 2010 From the Japanese Patent Office Re. Application No. 2007-206282.
Translation of Office Action dated Aug. 3, 2011 From the State Intellectual Property Office (SIPO) of the People's Republic of China Re.: Application No. 200480012687.5.
Translation of Office Action dated Apr. 20, 2011 From the State Intellectual Property Office (SIPO) of the People's Republic of China Re.: Application No. 200480012687.5.
USPTO Public Print Out of Interference File Content of Interference dated Apr. 4, 2011 From the U.S. Patent and Trademark Office Re. Interference No. 105,765.
USPTO Public Print Out of Interference File Content of Interference dated Apr. 4, 2011 From the U.S. Patent and Trademark Office Re. Interference No. 105,768.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Antman et al. "Treatment of 150 Cases of Life-Threatening Digitalis Intoxication With Digoxin-Specific Fab Antibody Fragments", Circulation, 81(6): 1744-1752, Jun. 1990.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Augello et al. "Cardiac Contractility Modulation by Non-Excitatory Electrical Currents. The New Frontier for Electrical Therapy of Heart Failure", Italian Heart Journal, 5(Suppl.6): 68S-75S, 2004.
Babsky et al. Translation of Physiology of Man, Moscow Medicine, p. 115, 348-351, 376, Extracts, 1972.
Bach "Tach Arrhythmia Detection", Implantable Cardioverter Defibrilator Therapy: The Engineering—Clinical Interface, Kluwer Academic Publishers, Chap. 15: 303-323, 1997.
Bakker et al. "Beneficial Effects of Biventricular Pacing of Congestive Heart Failure", Pace, 17(Part11): 318, 1994.
Bakker et al. "Biventricular Pacing in End-Stage Heart Failure Improves Functional Capacity and Left Ventricular Function", Journal of Interventional Cardiac Electrophysiology 4: 395-404, 2000.
Bargheer et al. "Prolongation of Monophasic Action Potential Duration and the Refractory Period in the Human Heart by Tedisamil. A New Potassium-Blocking Agent", Journal European Heart, 15(10): 1409-1414, 1994.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.

Blank et al. "Initial Interactions in Electromagnetic Field-Induced Biosynthesis", Journal of Cellular Physiology, 199: 359-363, 2004.
Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356-1364, 1996.
Bronzino "Biomedical Engineering Handbook", IEEE Press/CRC Press, Chap. 82.5: 1288, 1995.
Brumwell et al. "The Amplifier Sensing the Depolarization", Implantable Cardioverter Defibrillator Therapy: The Engineering-Clinical Interface, Kluwer Academic Publishers, Chap. 14: 275-302, 1997.
Burfeind et al. "The Effects of Mechanical Cardiac Stabilization on Left Ventricular Performance", European Journal of Cardio-Thoracic Surgery. 14: 285-289, 1998.
Burkhoff et al. "Nonexcitatory Electrical Signals for Enhancing Ventricular Contractility: Rationale and Initial Investigations of An Experimental Treatment for Heart Failure", American Journal of Physiology—Heart and Circulatory Physiology, 288(6): H2550-H2556, Jun. 2005.
Butter et al. "Enhanced Inotropic State of the Failing Left Ventricle by Cardiac Contractility Modulation Electrical Signals is Not Associated With Increased Myocardial Oxvgen Consumption", Journal of Cardiac Failure, 13(2): 137-142, 2007.
Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.
Devedeux et al. "Uterine Electromyography: A Critical Review", American Journal of Obstetric Gynecology, 169(6): 1636-1653, 1993.
Dillon "Optial Recordings in the Rabbit Heart Show That Defibrillation Strength Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878,1992.
Erol-Yilmaz et al. "Reversed Remodelling of Dilated Left Sided Cardiomyopathy After Upgrading from VVIR to VVIR Biventricular Pacing", Europace, 4: 445-449, 2002.
Fain et al. "Improved Internal Defibrillation Efficacy With A Biphasic Waveform", American Heart Journal, 117(2): 358-364, 1989. Abstract.
Fleg et al. "Impact of Age on the Cardiovasvular Response to Dynamic Upright Exercise in Healthy Men and Women", Journal of Applied Physiology, 78: 890-900, 1995. Abstract.
Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.
Foster et al. "Acute Hemodvnamic Effects of Atrio—Biventricular Padng in Humans", The Society of Thoracic Surgeons, 59: 294-300, 1995.
Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.
Franz "Method and Theory of Monophasic Action Potential Recording", Progress in Cardiovascular Diseases, 33(6): 347-368, 1991. Abstract.
Franz "Monophasic Action Potential Symposium, I. Introduction", Progress in Cardiovascular Diseases, 33(6): 345-346, 1991.

(56) References Cited

OTHER PUBLICATIONS

Fromer et al. "Ultrarapid Subthreshold Stimulation for Termination of Atriventricular Node Reentrant Tachycardia", Journal of the American College Cardiology, 20: 879-883, 1992.
Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991. Abstract.
Gardner "Natriuretic Peptides: Markers or Modulators of Cardiac Hypertrophy?", Trends in Endocrinology and Metabolism, 14(9): 411-416, Nov. 2003.
Gill et al. "Refractory Period Extension During Ventricular Pacing at Fibrillatory Pacing Rates", Pacing and Clinical Elctrophysiology, 20(3): 647-653, 1997. Abstract.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Gold et al. "Evidence That Glucose 'Marks' Beta Cells Resulting in Preferential Release of Newly Synthesized Insulin", Science. 218(4567): 56-58, Oct. 1, 1982. Abstract.
Gomis et al. "Oscillatory Patterns of Electrical Activity in Mouse PancreaticIslets of Langerhans Recorded in Vivo", Pfl?gers Archiv European Journal of Physiology, 432(3): 510-515, 1996.
Guidant Guidant Product Catalogue, 2 P., 2001.—No Copy Attached.
Gussoni et al. "Dystrophin Expression in the MDX Mouse Restored by Stem Cell Transplantation", Nature, 401(6751): 390-394, 1999.
Ham et al. "Classification of Cardiac Arrhythmias Using Fuzzy Artmap", IEEE Transactions on Biomedical Engineering, 43(4): 425-429, 1996, Abstract.
Hammond et al. "Motor Innervation of the Cricopharyngeus Muscle by the Recurrent Lanryngeal Nerve", Journal of Applied Physiology, JAP, 83: 89-94, 1997.
Hardage et al. "Anti-Tachycaidla Pacing and Cardioversion", Developments in Cardiovascular Medicine, Kluwer Academic Publishers, 188: 325-342, 1997.
Highfill et al. "Large-Scale Production of Murine Bone Marrow Cells in An Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Hoffman et al. "Effects of Postextrasystolic Potentiation on Normal and Failing Hearts", Bulletin of the New York Academy of Medicine, 41(5): 498-534, 1965.
Holst et al. "Nervous Control of Pancreatic Endocrine Secretion in Pigs. 1. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450, 1998.
Josephson "Clinical Cardiac Electrophysiology: Techniques and Interpertations", Lea & Febiger, 2nd Ed., 2 P., 1991.
Kanno et al. "Establishment of A Simple and Practical Procedure Applicable to Therapeutic Angiogenesis", Circulation, 99: 2682-2687, 1999.

King et al. "The Inotropic Action of Paired Pulse Stimulation in the Normal and Failing Heart: An Experimental Study", Cardiovascular Research, 2: 122-129, 1968.
Knisley et al. "Effect of Field Stimulation on Cellular Repolarization in Rabbit Myocardium. Implications for Reentry Induction", Circulation Research, 70(4): 707-715, Apr. 1992.
Knisley et al. "Prolongation and Shortening of Action Potentials by Electrical Shocks in Frog Ventricular Muscle", American Journal of Physiology, 266(6): H2348-H2358, 1994.
Koller et al. "Relation Between Repolarization and Refractoriness During Programmed Electrical Stimulation in the Human Right Ventricle", Circulation, 91(9): 2378-2384, 1995.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.
Langberg et al. "Identification of Ventricular Tachycardia With Use of the Morphology of the Endocardial Electrogram", Circulation, 77(6): 1363-1369, 1988.
Lawo et al. "Electrical Signals Applied During the Absolute Refractory Period. An Investigational Treatment for Advanced Heart Failure in Patients With Normal QRS Duration", Journal of the American College of Cardiology, 46(12): 2229-2236, 2005.
Lindstroem et al. "Intracellular Calcium Oscillations in A T-Cell Line After Exposure to Extremely-Low-Frequency Magnetic Fields With Variable Frequencies and Flux Densities", Bioelectromagnetics, 16(1): 41-47, 1995. Abstract.
Loginov "[Accumulation of Calcium Ions in Myocardial Sarcoplasmic Reticulum of Restrained Rats Exposed to the Pulsed Electromagnetic Field]", Aviakosmicheskaia i Ekologicheskaia Meditsina (Aerospace and Environmental Medicine), 26(2): 49-51, Mar.-Apr. 1992. Abstract.
Loginov et al. "Effects of an Impulse Electromagnetic Field on Calcium Ion Accumulation in the Sarcoplasmic . . .", Kosm. Biol. Aviakosm. Med., 15: 51-53, 1991. Abstract.
Lubart et al. "Effect of Light on Calcium Transport in Bull Sperm Cells", Journal of Photochemistry and Photobiology B, Biology, 15(4): 337-341, Sep. 15, 1992. Abstract.
Luiken et al. "Contraction-Induced Fatty Acid Translocase/CD36 Translocation in Rat Cardiac Myocytes is Mediated Through AMP-Activated Protein Kinase Signaling", Diabetes, 52: 1627-1634, 2003.
Magnus et al. "Model of Beta-Cell Mitochondrial Calcium Handling and Electrical Activity. II. Mitochondrial Variables", American Journal of Physiology, Cell Physiology, 274(43): C1174-C1184, 1998.
Matheny et al. "Vagus Nerve Stimulation as A Method to Temporarily Slow or Arrest the Heart", Annals of Thoracic Surgery, 63(6 Suppl.): S28-29, 1997. Abstract.
Mcveigh et al. "Noninvasive Measurement of Transmural Gradients in Myocardial Strain With MR Imaging", Radiology, 180(3): 677-684, 1991.
Mercando et al. "Automated Detection of Tachycardias by Antitachycardia Devices", Cardiac Electrophysiology: From Cell to Bedside, Chap. 100: 943-948, 2004.
Merck "The Merck Manual", 16th Ed, Section 3, 1992.—No Copy Attached.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Miledi et al. "Effects of Membrane Polarization on Sarcoplasmic Calcium Release in Skeletal Muscle", Proceedings of the Royal Society of London, Series B, Containing Papers of A Biological Character, 213(1190): 1-13, Sep. 17, 1981. Abstract.
Misler et al. "Electrophysiology of Stimulus-Secretion Coupling in Human Beta-Cells", Diabetes, 41(10): 1221-1228, Oct. 1992. Abstract.
Moran et al. "Digoxin-Specific Fab Fragments Impair Renal Function in the Rat", Journal of Pharmacy and Pharmacology, 46(10): 854-856, 1994, Abstract.

(56) References Cited

OTHER PUBLICATIONS

Morse et al. "A Guide to Cardiac Pacemakers, Defibrillators and Related Products", Droege Computing Services, Inc., vol. I, Nov. 19, 1996.
Nadal et al. "Homologous and Heterologous Asynchronicity Between Identified Alpha-, Beta- and Delta-Cells Within Intact Islets of Langerhans in the Mouse", Journal of Physicology, 517(Pt.1): 85-93, 1999.
Nannini et al. "Muscle Recruitment With Intrafascicular Electrodes", IEEE Transactions on Biomedical Engineering, 38: 769-776, 1991. Abstract.
Neelagaru et al. "Nonexcitatory, Cardiac Contractility Modulation Electrical Impulses: Feasibility Study for Advanced Heart Failure in Patients With Normal QRS Duration". Heart Rythm, 3(10): 1140-1147, 2006.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.
Pappone et al. "Cardiac Contractility Modulation by Electric Currents Applied During the Refractory Period in Patients With Heart Failure Secondary to Ischemic or Idiopathic Dilated Cardiomyopathy", The American Journal of Cardiology, 90(12): 1307-1313, Dec. 15, 2002.
Pappone et al. "Electrical Modulation of Cardiac Contractility: Clinical Aspects in Congestive Heart Failure", Heart Failure Reviews, 6(1): 55-60, Jan. 2001.
Pappone et al. "First Human Chronic Experience With Cardiac Contractility Modulation by Nonexcitatory Electrical Currents for Treating Systolic Heart Failure: Mid-Term Safety and Efficacy Results From A Multicenter Study", Journal of Cardiovadcular Electrophysiology, 15(4): 418-427, Apr. 2004.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Patterson et al. "Therapeutic Angiogenesis: The New Electrophysiology?", Circulation, 99(20): 2614-2616, 1999.
Paul et al. "Automatic Recognition of Ventricular Arrhythmias Using Temporal Electrogram Analysis", PACE, 14: 1265-1273, 1991.
Pediatric Electrophysiology "The Latest Tetralogy of Fallot Discussion With Graphical Support Including Video of Echocardiography and Catherization", Pediatric Electrophysiologypicu Book.—No Copy Attached.
Pokrovsky et al. "Physiology of Man", 1: 82-83, 94, 2: 42, 54.
Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Pumir et al. "Control of Rotating Waves in Cardiac Muscle: Analysis of the Effect of Electric Fields", Proceedings of the Royal Society B: Biological Sciences, 257(1349): 129-134, 1994. Abstract.
Ranjan et al. "Electrical Stimulation of Cardiac Myocytes", Annals of Biomedical Engineering, 23(6): 812-821, 1995, Abstract.
Rivera et al. "Regulation of Protein Secretion Through Controlled Aggregation in the Endoplasmic Reticulum", Science, 287(5454): 826-830, Feb. 4, 2000. Abstract.
Sabbah et al. "Treating Heart Failure With Cardiac Contractility Modulation Electrical Signals", Current Heart Failure Reports, 3(21): 21-24, 2006.
Saksena et al. "Prevention of Recurrent Atrial Fibrillation With Chronic Dual-Site Right Atrial Pacing", Journal of the American College of Cardiology, 28(3): 687-694, 1996, Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998.

San Mauro et al. "Nerves of the Heart: A Comprehensive Review With A Clinical Point of View", Neuroanatomy, 8: 28-31, 2009.
Schirra et al. "Exendin(9-39) Amide is An Antagonist of Glucagon-Like Peptide-1(7-36) Amide in Humans", Journal of Clinical Investigation, 101(7): 1421-1430, Apr. 1998.
Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan. 1998. Abstract.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Serre et al. "Exendin-(9-39) is An Inverse Agonist of the Murine Glucagon-Like Peptide-1 Receptor: Implications for Basal Intracellular Cyclic Adenosine 3',5'-Monophosphate Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt.1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Shumaik et al. "Oleander Poisoning: Treatment With Digoxin-Specific Fab Antibody Fragments", Annals of Emergency Medicine, 17(7): 732-735, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Skale et al. "Inhibition of Premature Ventricular Extrastimuli by Subthreshold Conditioning Stimuli", Journal of the American College of Cardiology, 6: 133-140, 1985. Abstract.
Solomonow et al. "Control of Muscle Contractile Force Through Indirect High-Frequency Stimulation", American Journal of Physical Medicine, 62(2): 71-82, Apr. 1983. Abstract.
Soria et al. "Cytosolic Calcium Oscillations and Insulin Release in Pancreatic Islets of Langerhans", Diabetes & Metabolism, 24: 37-40, 1998.
Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.
Stix et al. "FT Chronic Electrical Stimulation During the Absolute Refractory Period of the Myocardium Improves Severe Heart Failure", European Heart Journal, 3: 1-6, Feb. 2004.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Supino "The System", Implantable Cardioverter Defibrillator Therapy: The Engineering-Clinical Interface, Kluwer Academic Publishers, Chap.8: 163-172, 1997.
Sutton et al. "The Foundation of Cardiac Pacing, Part I: An Illustrated Practical Guide to Basic Pacing", The Bakken Research Center Series, Chap.4: 50-59, 1991.
Sutton et al. "What is A Pacemaker?", The Foundations of Cardiac Pacing, Part I: An Illustrated Practical Guide to Basic Pacing, Chap.4.5: 73-74, 1991.
Sweeny et al. "Countershock Strength-Duration Relationship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Talit et al. "The Effect of External Cardiac Pacing on Stroke Volume", PACE, 13(5): 598-602, May 1990. Abstract.
Taniguchi et al. "Inhomogeneity of Cellular Activation Time and Vmax in Normal Myocardial Tissue Under Electrical Field Stimu-

(56) References Cited

OTHER PUBLICATIONS lation", American Journal of Physiology—Heart and Circulatory Physiology, 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997. Abstract.
Todd et al. "Subcutaneous Glucagon-Like Peptide I Improves Postprandial Glycaemic Control Over A 3-Week Period in Patients With Early Type 2 Diabetes", Clinical Science, 95: 325-329, 1998.
Tseng "Electroporation of Cell Membranes", Biophysical Journal, 60: 297-306, 1991.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of A Rabbit Middle Cerebral Artery. Evidence of A Cholinergic Endothelium-Dependent Component", Circulation Research, 70(6): 1104-1112, Jun. 1992.
Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.
Wang et al. "Islet Amyloid Polypeptide Tonally Inhibits Beta-, Alpha-, and Delta- Cell Secretion in Isolated Rat Pancreatic Islets", American Journal of Physiology, AJP—Endocrinology and Metabolism, 276(1 Pt.1): E19-E24, 1999.
Webster "Design of Cardiac Pacemakers", IEEE Press, p. xi-xiii, 1995.
Webster "Electrodes, Leads, and Biocompatibility", Design of Cardiac Pacemakers, IEEE Press, p. 141-144, 1995.
Wessale et al. "Stroke Volume and the Three Phase Cardiac Output Rate Relationship With Ventricular Pacing", PACE, 13: 673-680, 1990.
Windle et al. "Subthreshold Conditioning Stimuli Prolong Human Ventricular Refractoriness", American Journal of Cardiology, 57(6): 381-386, 1986. Abstract.
Wirtzfeld et al. "Physiological Pacing: Present Stams and Future Developments", PACE, 10(Part I): 41-57, Jan. 1987. Abstract.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Xue et al. "Neural-Network-Based Adaptive Matched Filtering for QRS Detection", IEEE Transactions on Biomedical Engineering, 39(4): 317-329, 1992. Abstract.
Yokoyama "The Phase of Supernormal Excitation in Relation to the Strength of Subthreshold Stimuli", Japanese Heart Journal, 17(3): 315-325, May 1976.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404. Apr. 1984. Abstract.
Zhou et al. "Prevention of Action Potentials During Extracellular Electrical Stimulation of Long Duration", Journal of Cardiovascular & Electrophysiology, 8(7): 779-789, 1997. Abstract.
Zipes et al. "Cardiac Electrophysiology—From Cell to Bedside", Saunders Co., 4th Ed., 2004. Book Description.
Official Action dated Aug. 13, 2020 from the U.S. Patent and Trademark Office Re. U.S. Appl. No. 16/232,088. (66 pages).
Official Action dated Feb. 8, 2021 From the U.S. Patent and Trademark Office Re. U.S. Appl. No. 16/232,088. (28 Pages).
Interview Summary dated Aug. 13, 2021 from the U.S. Patent and Trademark Office Re. U.S. Appl. No. 16/232,088. (3 pages).
Final Official Action dated Jun. 11, 2021 From the U.S. Patent and Trademark Office Re. U.S. Appl. No. 16/232,088. (20 Pages).

* cited by examiner

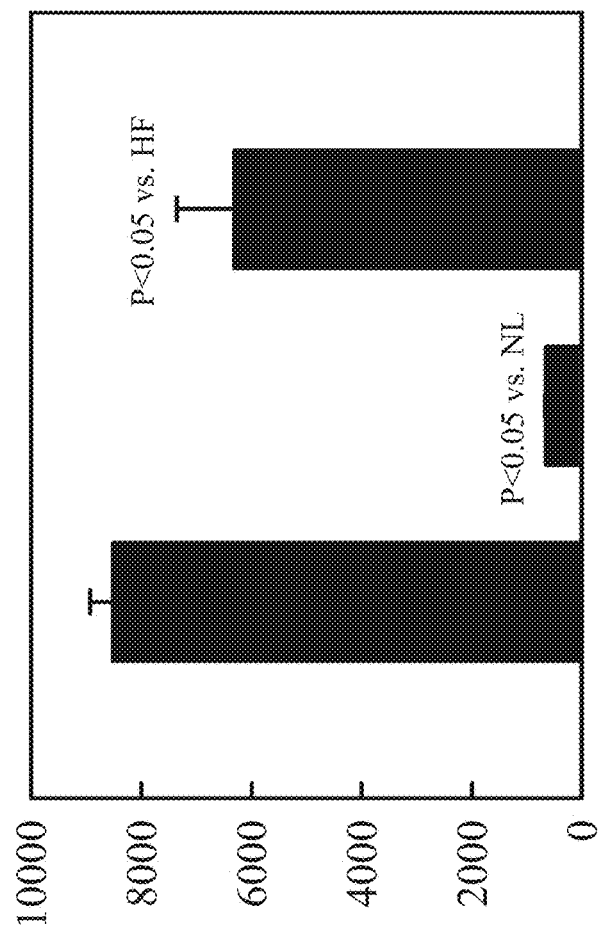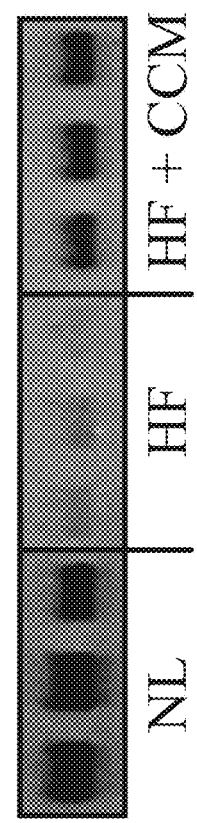
Fig. 2G

Fetal Program Genes
mRNA Expression of β1-Adrenergic Receptor
β1-AR
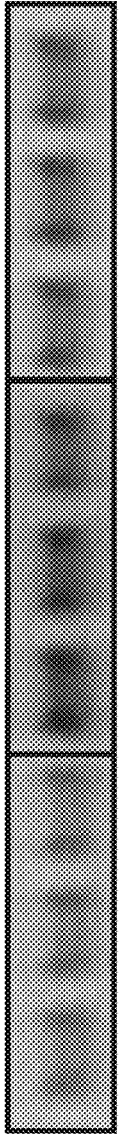
mRNA Expression for ANP
ANP
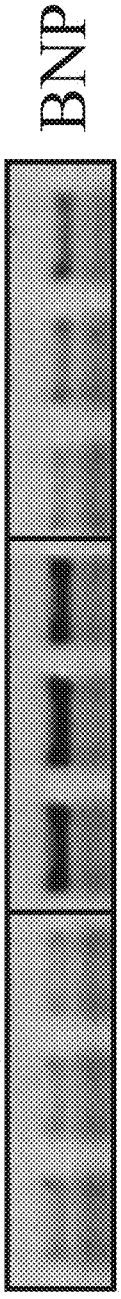
mRNA Expression for BNP
BNP
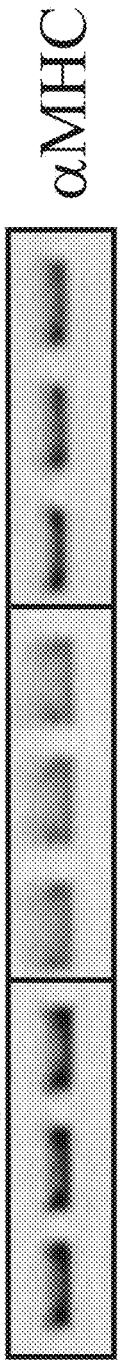
mRNA Expression for αMHC
αMHC
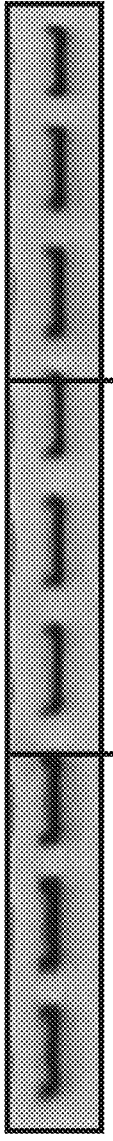
mRNA Expression of SERCA-2a
Serca-2a
NL | HF-Sham | HF + CCM
FIG 2N

Phosphorylation of Phospholamban, GATA-4 and Ryanodine Receptors In Isolated Failing Cardiomyocytes after Application of a Pacing Signal (3V, 0.75 msec) for 10, 20, 30, 40 and 60 Seconds

| 0 | 10 | 20 | 30 | 60 | seconds |
|---|---|---|---|---|---|

P-PLB @ Serine -16

| 46 | 38 | 42 | 43 | 38 | densitometric units |

P-PLB @ Threonine-17 (monomeric)

| 22 | 23 | 22 | 27 | 23 | densitometric units |

P-PLB @ Threonine-17 (pentameric)

| 29 | 28 | 26 | 25 | 23 | densitometric units |

Phosphorylation of GATA-4

| 22 | 24 | 24 | 24 | 23 | densitometric units |

Phosphorylation Ryanodine Receptor

| 86 | 92 | 90 | 85 | 86 | densitometric units |

P-PLB = Phosphorylation of phospholamban

Fig. 3E

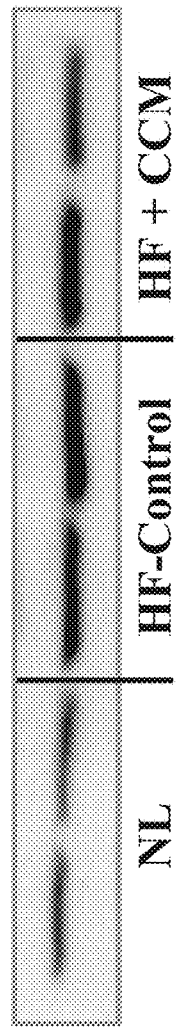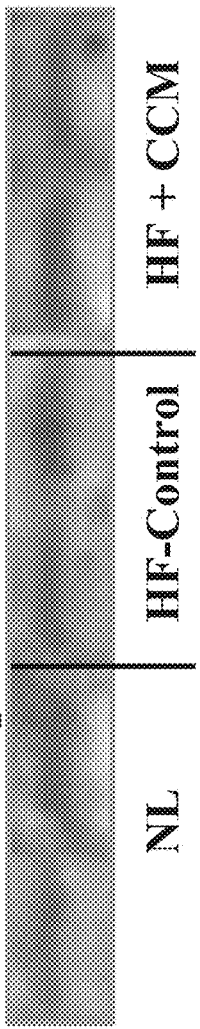
Fig. 5H

LV Tissue Protein Levels of the Matrix Metalloproteinases (MMP-1 and MMP-9) in Dogs with Heart Failure Treated Long-Term (3 months) with CCM Therapy
Protein Expression of MMP-1
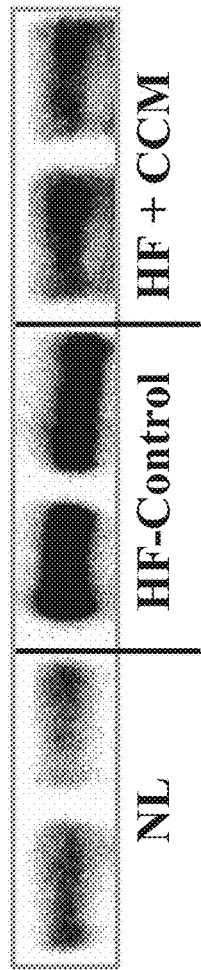
NL | HF-Control | HF + CCM
Protein Expression of MMP-9
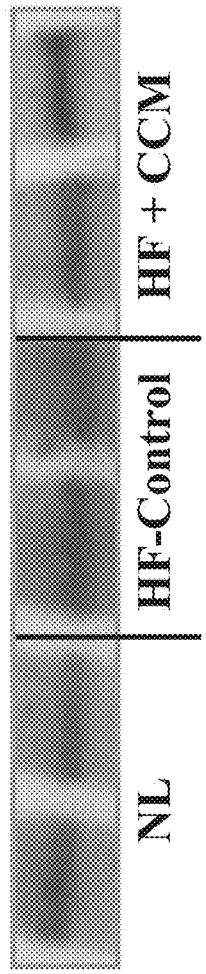
NL | HF-Control | HF + CCM
Fig. 51

LV Tissue Levels of the Cytoskeletal Proteins Tubulin-Alpha and Beta and Titin in Dogs with Heart Failure Treated Long-Term (3 months) with CCM Therapy
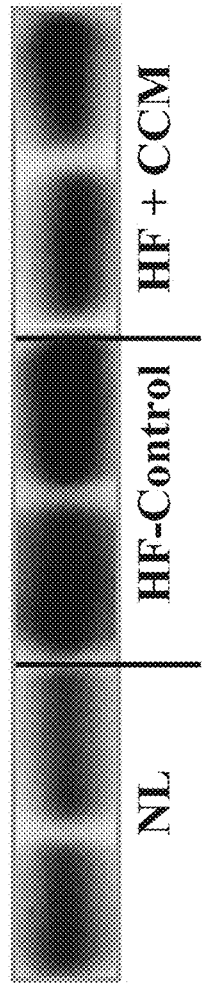
Protein Expression of Tubulin-Alpha
NL    HF-Control    HF + CCM
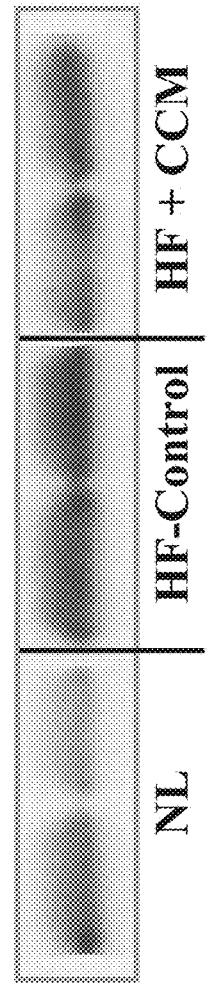
Protein Expression of Tubulin-Beta
NL    HF-Control    HF + CCM
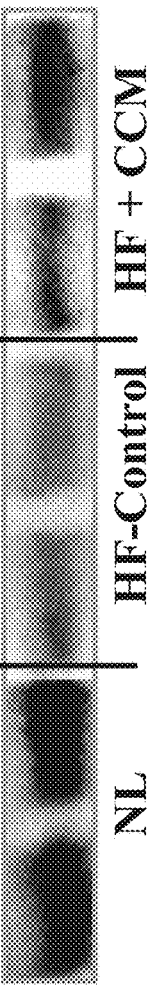
Protein Expression of Titin
NL    HF-Control    HF + CCM
Fig. 5J LV Tissue Protein Levels of the pro-Inflammatory Cytokine Interleukin-6 (IL-6) and Tissue Necrosis Factor-alpha (TNFα) in Dogs with Heart Failure Treated Long-Term (3 months) with CCM Therapy
Protein Expression of IL-6
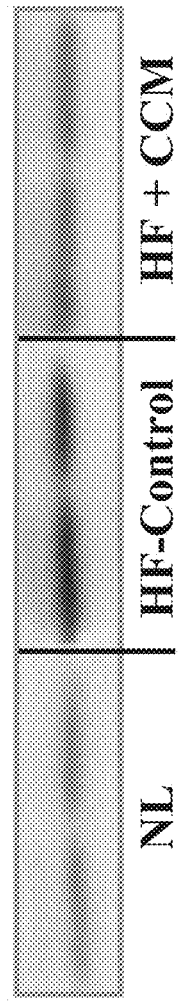
NL | HF-Control | HF + CCM
Protein Expression of TNF-α
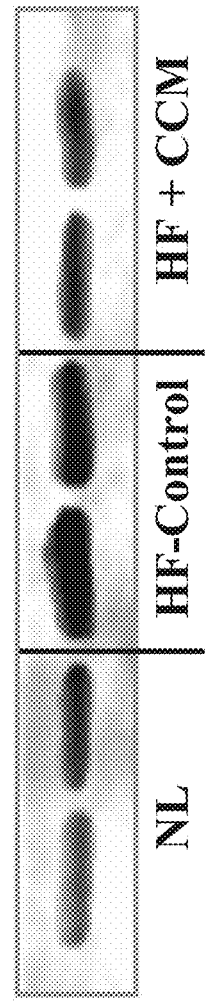
NL | HF-Control | HF + CCM
Fig. 5M

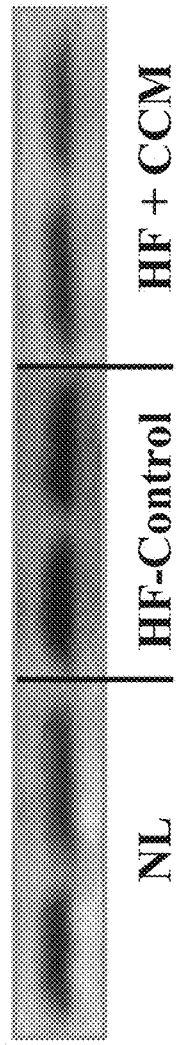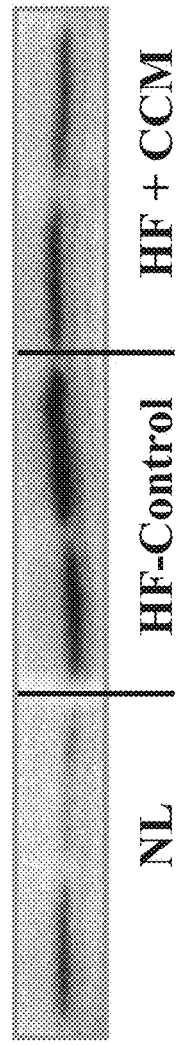
Fig. 5R

LV Tissue Protein Levels of Phosphorylated Phospholamban in Dogs with Heart Failure Treated Long-Term (3 months) with CCM Therapy
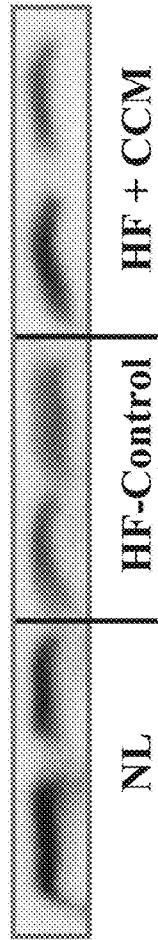
Phosphorylated Phospholamban at Serine-16
NL | HF-Control | HF + CCM
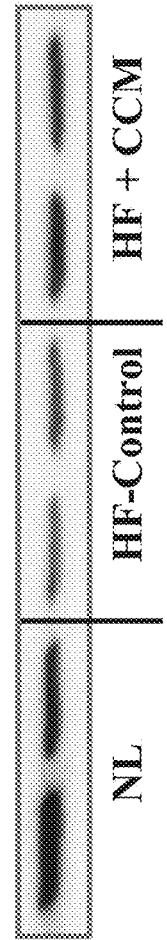
Phosphorylated Phospholamban at Threonine-17
NL | HF-Control | HF + CCM
Fig. 8

PROTEIN ACTIVITY MODIFICATION

RELATED PATENT APPLICATIONS

This Application is a continuation of U.S. patent application Ser. No. 11/792,811 filed on Jul. 31, 2009, which is a National Phase of PCT Patent Application No. PCT/US2005/044557 having International Filing Date of Dec. 9, 2005, which claims the benefit of U.S. Provisional Patent Application Nos. 60/634,625 filed on Dec. 9, 2004; 60/677,761 filed on May 4, 2005 and 60/719,517 filed on Sep. 22, 2005.

PCT Patent Application No. PCT/US2005/044557 is also a continuation-in-part of PCT Patent Application No. PCT/US2004/007589 filed on Mar. 10, 2004, which matured into U.S. National Phase patent application Ser. No. 10/549,216 filed on Oct. 12, 2006, now U.S. Pat. No. 7,840,262, and claims the benefit of U.S. Provisional Patent Application Nos. 60/453,349 filed on Mar. 10, 2003 and 60/503,075 filed on Sep. 15, 2003.

PCT Patent Application No. PCT/US2005/044557 is also a continuation-in-part of PCT Patent Application No. PCT/IL2005/000316 filed on Mar. 18, 2005, which claims the benefit of U.S. Provisional Patent Application Nos. 60/654,056 filed on Feb. 17, 2005 and 60/602,550 filed on Aug. 18, 2004.

PCT Patent Application No. PCT/IL2005/000316 is also a continuation-in-part of U.S. patent application Ser. No. 10/804,560 filed on Mar. 18, 2004, which claims the benefit of U.S. Provisional Patent Application No. 60/488,964 filed on Jul. 21, 2003.

PCT Patent Application No. PCT/IL2005/000316 is also a continuation-in-part of PCT Patent Application No. PCT/IL2004/000797 filed on Sep. 5, 2004 and PCT Patent Application No. PCT/IL2004/000551 filed on Jun. 20, 2004, which claims the benefit of U.S. Provisional Patent Application Nos. 60/480,208 filed on Jun. 20, 2003 and 60/488,964 filed on Jul. 21, 2003.

PCT Patent Application No. PCT/IL2005/000316 is also a continuation-in-part of PCT Patent Application No. PCT/IL2004/000664 filed on Jul. 21, 2004, which claims the benefit of U.S. Provisional Patent Application No. 60/488,964 filed on Jul. 21, 2003.

PCT Patent Application No. PCT/IL2005/000316 is also a continuation-in-part of PCT Application No. PCT/IL2004/000550 filed Jun. 20, 2004, which claims the benefit of U.S. Provisional Patent Application Nos. 60/480,205 filed on Jun. 20, 2003 and 60/480,208 filed on Jun. 20, 2003.

The contents of the above applications are all incorporated by reference as if fully set forth herein in their entirety.

FIELD AND BACKGROUND OF THE INVENTION

The present invention relates to modification of tissue behavior, for example using electric fields and for example using biochemical markers as feedback.

While some proteins have a mainly structural role in cellular life, many proteins are biologically active. Living cells include many mechanisms by which the biological activity of a protein is modulated, including: modification of concentration of the protein or its substrates, modification of the concentration of materials that catalyzes protein activity, indirect modification of protein structure, such as by changing of pH or concentrations of materials that modify protein structure, and direct modification of protein spatial structure and/or charge distribution by attachment of cofactors such as a phosphate moiety (phosphorylation), glucose, ions, metal ions, heme groups or iron-sulfur complexes and coenzymes for example.

The symptoms of many diseases include changes in protein activity, as indicated, for example, by phosphorylation (hyper- or hypo-). One example is cardiac heart failure, where, as the disease progresses the phosphorylation of some proteins goes down and others go up. Levels of various proteins also change.

As described, for example in N Engl J Med 346:1357, 2002, the disclosure of which is incorporated herein by reference, patients with CHF who respond to therapy with beta blockers manifest reversal that is normalization of the maladaptive fetal gene program.

In a paper entitled "Voltage-dependent potentiation of the activity of cardiac L-type calcium channel al subunits due to phosphorylation by cAMP-dependent protein kinase", by Adrian SCULPTOREANU, Eric ROTMAN, Masami TAKAHASHI, Todd SCHEUER, AND William A. CATTERALL, in Proc. Natl. Acad. Sci. USA Vol. 90, pp. 10135-10139, November 1993 (Physiology), the disclosure of which is incorporated herein by reference, fast phosphorylation of trans-membrane calcium channels and a possible mechanism therefor, are described.

U.S. Pat. No. 6,919,205, the disclosure of which is incorporated herein by reference, describes regulation of type II cartilage genes and proteins using electromagnetic and electric fields.

SUMMARY OF THE INVENTION

A broad aspect of some embodiments of the invention relates to modifying the activity of proteins or other biochemicals optionally in situ and/or in vivo, for example, by modifying protein phosphorylation, using electro-magnetic or electrostatic fields. In an exemplary embodiment of the invention, the activity of the protein that is modified is one or more of signaling, catalysis, material transport and/or charge transport. While the term phosphorylation is used in the specific sense, the embodiments described herein are intended to cover other attachment/detachment of protein cofactors.

Some embodiments of the invention are based on the surprising discovery by the inventors that an electric field can have an immediate effect on phosphorylation or proteins.

In some embodiments of the invention, modification of protein expression and/or mRNA expression are practiced, in addition to or instead of phosphorylation changes. In an exemplary embodiment of the invention, protein levels of at least two proteins are normalized by application of an electric field.

In an exemplary embodiment of the invention, the modification method is used as a therapy and/or in diagnosis, for example for a diseased heart and/or for other organs in the body.

In an exemplary embodiment of the invention, the modification of the protein activity is a relatively direct result of the method, rather than a side effect. This directness can be noticed, for example in the time scale of some embodiments of the invention, where a change in phosphorylation is noticeable within a few seconds or minutes. Alternatively or additionally, the directness can be noticed in a lack of intermediates, for example as indicated by the change in phosphorylation taking place even in cell homogenate.

In an exemplary embodiment of the invention, the modification is evident without requiring the synthesis of new protein. For example, phosphorylation of existing proteins may be provided.

In an exemplary embodiment of the invention, modification of protein activity and/or phosphorylation comprises modifying a steady state average level of such phosphorylation. Optionally, this modification comprises periodically increasing the percentage of phosphorylated proteins. Alternatively or additionally, the modification is achieved by shifting a balance between phosphorylation and dephosphorylation. In some embodiments, the modification relates to a single heart beat.

In an exemplary embodiment of the invention, the modification is on the time scale of a single or small number of heart beats, or faster (e.g., 1 second or faster). Optionally, an effect of the modification is noticeable on a same time scale.

In an exemplary embodiment of the invention, the affected proteins are proteins that act on a non-protein substrate, for example calcium channel proteins. Alternatively or additionally, the proteins are signaling proteins and/or act on other proteins and/or are acted on by other proteins. For example, the affected protein enhances the activity of various enzymes, which, in turn, regulate essential ion channels and pumps.

An aspect of some embodiments of the invention relates to using phosphorylation as a target for therapy, especially a therapy where the therapy method can be controlled at a relatively fast rate. For example, phosphorylation of phospholamban leads to increased activity of calcium ATPase and/or increase of the affinity of calcium ATPase pump for calcium. This, in turn, leads to increased or enhanced uptake of calcium from the cell cytosol to the sarcoplasmic reticulum (SR).

In an exemplary embodiment of the invention, changing phosphorylation will stabilize the cell biochemistry and prevent or undo decline in cell functionality. This may allow a general improvement in the patient to occur, for example, as natural feedback and healing processes can kick into action.

In an exemplary embodiment of the invention, an indication of protein activity other than phosphorylation is used for example, either as feedback or to determine efficacy, for example, microbiological parameters such as SR calcium level or macro parameters such as cardiac output as a function of $MVO_2$.

In an exemplary embodiment of the invention, the target of therapy is achieving a relative phosphorylation level. Alternatively or additionally, the target is achieving an absolute phosphorylation level. Such a target may be a window, with the values of the window optionally being variable. In one example, the values are dependent on 1) the state of phosphorylation of the protein, 2) the availability of the protein itself, 3) the condition and viability of the organ, 4) stressful conditions imposed upon the organ as a result of daily activity and 5) resulting from variation in circadian rhythm.

In an exemplary embodiment of the invention, the target of therapy is achieving an effect of change in phosphorylation, for example, a change of cellular function, caused for example, by rebalancing a previously upset balance between the activity of various proteins or setting a new set point of a new, less hazardous balance (e.g., for therapy of a condition where the balance is hazardous).

In an exemplary embodiment of the invention, the target is achieving a certain value or profile of protein activity, for example, a certain calcium pumping rate or pumping profile (as dependent on concentration and/or cell stress), which value or profile is determined by the phosphorylated protein, alone or in conjunction with other associated proteins or cellular mechanisms.

In an exemplary embodiment of the invention, when the phosphorylation is used as a target, the therapy is increased, decreased and/or otherwise modified based on its actual or expected effect on phosphorylation. In an exemplary embodiment of the invention, feedback is provided for the method by measuring phosphorylation directly or indirectly.

In an exemplary embodiment of the invention, phosphorylation is used as a negative or minimum target. For example, when it is not possible to achieve a desired effect on an entire heart, for example, due to power limits or side effect limits, a minimum phosphorylation target is set for various parts of the heart and the therapy is configured so that this minimum achievable target is achieved. In another example, it may be desirable to minimize the amount of phosphorylation, for example in the event that hyperphosphorylation leads to progressive worsening of disease. In this case, the pulse sequences applied may be optimized to minimize the global and/or regional expected or measured phosphorylation of a particular protein. In an exemplary embodiment of the invention, phosphorylation modification in ischemic and non-ischemic regions is different or otherwise dependent on the condition of underlying tissue. For example, ischemic regions being controlled to improve phosphorylation and non-ischemic regions are controlled to also increase contractility.

In an exemplary embodiment of the invention, phosphorylation is used as a single or as one of several parameters in optimization or selection of a pulse sequence.

In an exemplary embodiment of the invention, phosphorylation is used as a guide for electrification sequence parameters settings. In some cases it may not be practical to use phosphorylation as an indicator for feedback, however, general experiments (such as those described herein) may show that certain sequences have a certain effect on phosphorylation. In an exemplary embodiment of the invention, sequences that are defined for another effect, for example, contractility modulation, are modified to take into account the results of these experiments. In another example, a sequence that is shown to have a certain phosphorylation effect is used in an open or semi-open loop, rather than a closed loop. The phrase "semi-open loop" is used to mean that feedback and modification of the sequence is at a much slower rate than the application of the sequence, for example, once a week or once a month for a sequence applied once an hour or more often.

An aspect of some embodiments of the invention relates to kits and methods of use thereof. In an exemplary embodiment of the invention, a kit includes a means to analyze a tissue sample to determine some indication of its phosphorylation levels, protein expression levels, mRNA levels and/or other biochemical markers. Optionally, the kit includes 1, 4, 10, 20, 25 or more or intermediate numbers of biochemical marker detectors for markers as described herein and/or additional markers.

In an exemplary embodiment of the invention, the type and/or severity of the disease is classified using the expression results and/or response to treatment results for a plurality of genes/proteins, for example, 3, 5, 10, 20 or more. In an exemplary embodiment of the invention, a database is built up by storing typical results for different patients and detecting relationships between levels/responses that are associated with certain outcomes and/or pathologies. It is expected that with increase in the number of biochemical markers and/or treatments that such classifications can be detected.

In an exemplary embodiment of the invention, the kit includes instructions for use, optionally including thresholds of expected values and/or changes in values expected over time. Optionally, the kit is useful for one or more of diagnosis, detecting treatment progress and/or classifying patients according to expected responsiveness.

In an exemplary embodiment of the invention, the kit is included with suitable software which tracks values and/or provides results.

In an exemplary embodiment of the invention, the kit is used while device implanting, to assess a suitable implantation area of electrodes in the heart for example, according to the response to acute stimulation indicated by the kit.

Optionally, the kit is used by taking a tissue biopsy, for example, using a needle or a catheter and testing the levels of bio-chemicals in a biopsy sample.

In an exemplary embodiment of the invention, the kit is used for active testing of a tissue sample. A tissue sample is extracted and optionally homogenized (e.g., using a separate device) and then an electric field or other treatment is applied to the sample. Depending on the response of the sample, a diagnosis, progress and/or classification is determined. Optionally, the kit is provided with a set of electrodes which can be selectively attached to an implantable device, to assess its effect on homogenate. Alternatively or additionally, a stand-alone electrification system is used. Optionally, this stand-alone system includes a controller adapted to apply multiple electrification schemes and optionally store the effect of each scheme. Optionally, the stand-alone device includes a sampling chamber for selecting a part of the tested sample and applying a test thereto, for example, determining instantaneous or near instantaneous phosphorylation.

In another example, the kit is used to test pre-treatment levels of biochemicals, including, for example, phosphorylation level.

In an exemplary embodiment of the invention, the kit is packaged as a separate entity, while in some cases, multiple kits may be used, which may be packaged as a set. Optionally, different kits for different sets of biochemical markers are provided. Alternatively or additionally, the kits are provided, for example, as single or multiple one-time kits, with a cardiac controller, to be used as part of the implantation and/or electrode location searching process.

Optionally, the kit is used during implantation, before implantation is finalized, to help decide if the device should be left in the body or not, depending on its acute efficacy, for example, on phosphorylation.

Optionally, a kit is used to test treatment other than electrical treatments, for example, drug treatments or exercise treatments. Optionally, the kit is used by sampling a sample before and after the treatment or by applying a proposed treatment to the sample itself and seeing if the sample exhibits a positive effect.

An aspect of some embodiments of the invention relates to controlling tissue, for example soft tissue and/or non-cartilagous tissue and/or non-supporting tissue such as the heart, by directly affecting a balance point of phosphorylation or other biochemical activities therein.

In an exemplary embodiment of the invention, an electric field is applied which skews a balance between phosphorylation and dephosphorylation of a protein. This skewing optionally includes a long term increase in phosphorylation, for example if the time constants of dephosphorylation are higher than those of dephosphorylation. In an exemplary embodiment of the invention, the protein affected is phospholamban or an ion channel, for example a trans-membrane calcium channel.

In an exemplary embodiment of the invention, the effect is a short term effect, for example, by applying the field in a manner which allows long term phosphorylation levels to recover and thus prevent a long term change in cellular behavior, while providing an acute effect. In a particular example, the field is applied for a short time and then stopped until (e.g., according to measurement or estimation) the phosphorylation levels received. Optionally, the field is applied for a short enough time that the total acute change is small, for example a few percent (e.g., <10 percent). Optionally, a mix or intermediate situation between short and long term effect is provided. Optionally, both large acute changes and gradual long term changes are provided, for example with long term changes being on the range of hours and acute changes seconds or minutes.

Optionally, the field is applied often enough to cause a long term effect. Optionally, the frequency of application causes only a slow change in acute values, optionally causing no acute effects to be seen.

In an exemplary embodiment of the invention, the applied field is modified to take into account the change in cellular behavior and/or change in phosphorylation.

It is noted that a test field applied for testing tissue response may not be the same as the treatment field. In one example, the test field is stronger. In another example, the treatment field is modified based on the results of the test field.

In an exemplary embodiment of the invention, the balance between phosphorylation and dephosphorylation is tipped to restore a correct balance. Alternatively or additionally, the balance is skewed to be abnormal, for example to drive a cellular homeostasis mechanism in a direction to correct a defect in cellular behavior and/or compensate for such behavior.

Optionally, the applied electric field is a dual function field, for example, being used for pacing or preventing arrhythmia. Optionally, the applied field does not acutely (e.g., within 10 heart beats or fewer) increase contractility by more than 3%, or less.

An aspect of some embodiments of the invention relate to new therapeutic non-excitatory sequences for the heart. Optionally, these sequences have as an aim to improve phosphorylation, rather than only contractility and in some cases, without immediate improvement in contractility. Optionally, a phosphorylation improving sequence, while generally capable of contractility enhancement, is applied at too low a repetition rate and/or power to achieve a meaningful change in contractility.

In an exemplary embodiment of the invention, the sequences are optimized to one or more of acute or longer term effects of one or more of phosphorylation, protein and/or mRNA levels.

Acute effects have some potential benefits for use as feedback, including one or more of faster feedback so faster optimization and/or per patient optimization can more easily be achieved, relative steadiness of physiological condition during optimization and/or ability to control an ongoing process, such as titrating of therapeutic drugs particularly in i.v. type drugs or delivery of any drug and dose.

In an exemplary embodiment of the invention, the optimization (including a semi-optimization) is on a per patient, per tissue (e.g., location in heart), per diagnosis and/or per patient classification group.

In an exemplary embodiment of the invention, as compared to contractility modifying signals, the sequences have a lower duty cycle and/or more quiet periods between sequences, designed such that a desired phosphorylation effect is achieved, even if a sufficient charge is not delivered each beat (or any beat) to cause significant increase in contractility. In an exemplary embodiment of the invention, the sequence is based on a delivery of minimum signals that increase phosphorylation, at time intervals timed so that decay of phosphorylation between applications is smaller than or the same as the increase achieved by an application. Optionally, the delay between signals and/or signal length and/or other parameters vary over time to track a possibly varying effect of the signal on phosphorylation as phosphorylation changes.

In some cases, a field which would otherwise reduce contractility (e.g., a hyperpolarizing field) is used.

In an exemplary embodiment of the invention, a power saving sequence is defined, which, for example, is designed to maintain phosphorylation levels, even if a desired contractility enhancement is not directly achieved, by reducing pulse amplitude, frequency of application and/or other power-related parameters. In some cases, contractility is not a consequence of the phosphorylation normalization.

In an exemplary embodiment of the invention, a minimum dosage sequence is defined, which achieves a desired phosphorylation effect, without necessarily achieving other immediate beneficial effects such as contractility enhancement effects. Long-term, the improvement in phosphorylation may also improve contractility. In an exemplary embodiment of the invention, a therapeutically effective sequence comprises applying a field to the heart less often than once in 5 minutes, once in 10 minutes, once in 30 minutes, once an hour, once a day and/or once a week. For some uses, a set of signals, for example, 10, 20 or 30 signals (each signal corresponding to one heart beat), may be applied at such intervals, with an optional inter-signal spacing.

In an exemplary embodiment of the invention, a phosphorylation-effecting signal comprises applying signals at different times in the cardiac cycle, such as absolute or relative refractory periods and excitatory period. The signal may be synchronized to the heart as a whole or to local activity, for example. Optionally, the signal is excitatory in some times of application. Optionally, the signal, at some embodiments thereof, may be applied at any point in the cycle, or at least during 60%, 80% or more of the cycle.

In an exemplary embodiment of the invention, the optimizing of the pulse sequence is based on selecting a pulse or pulse parameters which will have a desired effect on the patient, for example, phosphorylation, e.g., above 10% increase, 50%, 100%, 200%, 500%, 1000% or intermediate or larger percentage increases. In some cases, a decrease is desired, for example, a decrease of 20%, 40%, 70%, 90% or intermediate or greater percentage reductions.

In an exemplary embodiment of the invention, a method of manufacturing is provided in which a pacemaker or another electrical field applying device is programmed to have a pulse known to have a desired biochemical effect, such as phosphorylation, optionally even if such pulse has a reduction in other effect.

An aspect of some embodiments of the invention relates to controlling a heart taking into account differences between local and remote effects of a treatment such as electrical field application.

In an exemplary embodiment of the invention, a local area is an area which is directly affected by the treatment, for example a tissue area lying between two electrodes that are electrified or an areas to which a pharmaceutical is provided, for example using a path or using local injection or using other methods known in the art. In an exemplary embodiment of the invention, the tissue in this area is used to detect immediate effects of the field, for example, change in phosphorylation and changes in contractility. Optionally, a sensor is provided at the local area for example, a sensor that measures local muscle function and/or biochemical behavior, which sensor generates an indication of the effect of the sequence. Optionally, a one time use sensor is used, for example an anti-body covered optical fiber. Optionally, several such sensors are provided.

Alternatively or additionally to acute measurements within minutes or seconds, measurements on a scale of hours are made.

In an exemplary embodiment of the invention, the remote area is in the same heart chamber or in a different heart chamber and serves to indicate general progress in the cardiac condition. Optionally, such general progress is detected by measuring changes in biochemical markers in such remote tissue.

Optionally, a treatment aims to improve one or both of local and remote effects.

In an exemplary embodiment of the invention, areas to treat are selected based on a desired local and/or remote effect. In one example, local (e.g., electrode application) areas are selected such that a general improvement in cardiac function and a subsequent remote effect may be expected. In another example, multiple local areas are selected so as to positively control the cellular behavior in those areas, for example simultaneously or in series.

In an exemplary embodiment of the invention, progress is measured by detecting a wave-like propagation of tissue improvement, starting at the sites of electrode application. Such sites may be selected to provide a desired such propagation of improvement over the heart. Alternatively or additionally, progress is detected by measuring gradual improvement in multiple locations simultaneously. Optionally, if improvement is measured using biopsies, different locations are sampled each time.

In an exemplary embodiment of the invention, electrode location are selected so as to best utilize exciting tissue resources, for example, enhance weak tissue rather than strong tissue or optimize use of blood flow resources. Optionally, the treatment areas are selected to increase blood demand and drive angiogenesis. Optionally, treatment is applied at areas where blood flow is reduced, as some treatments do not increase oxygen demand.

In an exemplary embodiment of the invention, electrode placement is selected to provide a desired stretching behavior to nearby tissue. Alternatively or additionally, electrode placement is selected to minimize diffusion or travel distances for biochemicals between treated areas and other areas.

In an exemplary embodiment of the invention, a local area is 10 $cm^2$, 5 $cm^2$, 3 $cm^2$, 2 $cm^2$, 1 $cm^2$ or smaller or intermediate sizes.

An aspect of some embodiments of the invention relates to applying a phosphorylation effecting signal on generally non-contracting tissue, such as plugs, transplants and/or scar tissue (especially at boundaries thereof). In an exemplary embodiment of the invention, this application is used to stabilize and/or improve phosphorylation levels in such tissue. In an exemplary embodiment of the invention, tissue plugs are removed and treated and then reinserted back into the heart (autograft). Optionally, the grafts are inserted into scar tissue.

In an exemplary embodiment of the invention, apparatus is provided for holding a plurality of tissue plugs (e.g., 3, 5, 10, 20 or more) while an electric field is applied thereto, for example, the apparatus including a chamber with physiological fluid, the chamber optionally including supports for the plugs. Optionally, one or more plugs are sampled or tested to see an effect of eth field. Optionally, one or more electrodes are provide din or adjacent the walls of said chamber.

In an exemplary embodiment of the invention, stimulation of scar tissue can cause it to regain mechanical activity, for example by stimulation and/or healing of dormant tissue therein.

In an exemplary embodiment of the invention, stimulation of a transplant is used to enhance its activity and/or prevent degradation due to removal and implant. Optionally, the stimulation used does not cause significant mechanical activity, for example, being applied at long time intervals. Optionally, the signal is applied to cooled, non-contracting tissue. Possibly, phosphorylation of a particular protein can lead to activity that stimulates the release, for example of specific neurohormones and activation of essential proteins. Optionally, the application of the signal to a cooled or cardioplegic heart is used during cardiac and/or brain surgery to facilitate restarting of the heart after such surgery.

An aspect of some embodiments of the invention relates to detecting of changes in biochemical behavior in the heart.

In an exemplary embodiment of the invention, changes in ECG morphology which indicate changes in protein levels and/or phosphorylation, are detected. Optionally, the morphology is a single cell clamp measurement.

In an exemplary embodiment of the invention, a catheter biopsy is used to extract tissue.

In an exemplary embodiment of the invention, a tissue sample is extracted and tested by stimulation/treatment thereof outside the body. Optionally, the tissue is homogenized and/or separated into individual cells.

In an exemplary embodiment of the invention, biochemical state is determined by measuring reactivity to other biochemicals. For example, the responsiveness to beta blockers may be detected to change when certain proteins are phosphorylated.

Optionally, antibody based tracers are used, for example, in conjunction with florescent dyes and/or radioactive materials.

An aspect of some embodiments of the invention relates to targeted therapy delivery and/or modulation of therapy. In an exemplary embodiment of the invention, a signal that modulates phosphorylation is applied, while the availability of a substrate relevant for phosphorylation is modified. In one example, a pharmaceutical which reduces or increases the phosphorylated protein is provided. In another example, the electric field is used to activate proteins generated using gene therapy, such as DNA plasmid injection coding for SERCA-2a, whereby phosphorylation of phospholamban would enhance the activity of the SERCA-2a. In an exemplary embodiment of the invention, targeting is achieved by therapy requiring the temporal and spatial intersection of the substrate/precursor and the signal which has the phosphorylation effect. Optionally, an area is drained of or filled with substrate, for example, by previous application of suitable signals, exercises and/or pharmaceuticals. For example, a cardiac region may be stressed to increase or reduce its susceptibility to the phosphorylation modifying signal.

In an exemplary embodiment of the invention, it is noted that the need of a substrate to be available for a protein to be phosphorylated allows selective achievement of the contractility modulation effect and the phosphorylation effect, for example by selectively applying the signal when there is no substrate and/or by selectively applying the signals often enough to achieve phosphorylation but not often enough for significant contractility enhancement.

In an exemplary embodiment of the invention, particular proteins are selectively affected by timing the lengths of signals applied so that they differentially affect one protein or another. Optionally, the signals are repeated in order to have a sufficient effect on a desired protein. Optionally, the signals are delayed from one another in order to allow changes in activity levels of a protein to decay. Optionally, selective mRNA expression is provided by selectively affecting proteins which cause mRNA changes.

An aspect of some embodiments of the invention relates to selective control of different proteins, for example selective phosphorylation rates thereof. In an exemplary embodiment of the invention, an electric field is used to differentially affect more one of phospholamban and calcium channels. Such differentiability is to be expected due to the difference in location in the cell of the two proteins (transmembrane and intracellular) and due to the different mechanism for dephosphorylation, each of which generally has a different time rate. Thus, applying pulses of electricity at a certain amplitude and/or a certain rate may be expected to affect one protein more than the other. Phosphorylation and dephosphorylation rates are optionally controlled by controlling availability of substrates and/or catalytic enzyme, for example, using suitable bio-chemicals applied to the cell or patient.

It should be noted that multiple mechanisms for improving contractility generally exist in a cell. Each of the calcium channels and the phospholamban, affect contractility in a different manner and this may allow selecting what manner of affect is desired.

In an exemplary embodiment of the invention, contractility increase of a cell is blocked using one biochemical, while using phosphorylation control to improve cellular homeostasis. Optionally, such blocking is applied locally, for example to small parts of the heart where the overall cardiac output will not be too damaged. Optionally, anti-arrhythmic treatment (e.g., electrical or drug) is applied at a same time.

In an exemplary embodiment of the invention, a local effect is applied to enhance local function of the heart, for example in viable regions of a ventricle after massive myocardial infarction. Alternatively or additionally, a local effect is applied to suppress the over contraction of a region of the heart as in patients with hyperdynamic septum as in asymmetrical septal hypertrophy.

In an exemplary embodiment of the invention, tissue viability (e.g., after infarct, donor organ) is tested using methods as described herein for examining activity.

There is therefore provided in accordance with an exemplary embodiment of the invention, a method of modifying tissue behavior, comprising:

determining a desired modification of tissue behavior for at least one of treatment of a disease, short or long term modification of tissue behavior, assessing tissue state and assessing tissue response to stimulation;

selecting an electric field having a known effect of modifying protein activation levels of at least one protein as an immediate response of a tissue to the field, said known effect correlated with said desired modification; and applying said field to said tissue.

In an exemplary embodiment of the invention, said tissue comprises cardiac tissue.

In an exemplary embodiment of the invention, at least one of said at least one protein is an SR protein.

In an exemplary embodiment of the invention, at least one of said at least one protein is not sensitive to physiologically occurring inter-cellular electric fields.

In an exemplary embodiment of the invention, at least one of said at least one protein is not an ion transport protein.

In an exemplary embodiment of the invention, at least one of said at least one protein controls another protein.

In an exemplary embodiment of the invention, said at least one protein comprises phospholamban.

In an exemplary embodiment of the invention, said at least one protein comprises a trans-membrane calcium channel.

In an exemplary embodiment of the invention, said at least one protein comprises a plurality of proteins. Optionally, said plurality of proteins belong to at least 2 separate biochemical control pathways. Alternatively or additionally, said plurality of proteins belong to at least 3 separate biochemical control pathways. Alternatively or additionally, said plurality of proteins belong to at least 4 separate biochemical control pathways. Alternatively or additionally, said separate pathways are protein interaction pathways. Alternatively or additionally, said separate pathways include genomic control.

In an exemplary embodiment of the invention, modifying protein activation levels comprises attaching or detaching a cofactor to at least on of said at least one protein.

In an exemplary embodiment of the invention, modifying comprises phosphorylation.

In an exemplary embodiment of the invention, modifying comprises dephosphorylation.

In an exemplary embodiment of the invention, modifying protein activation levels comprises modifying the activities of existing proteins, without synthesizing new proteins.

In an exemplary embodiment of the invention, said immediate response comprises a response within less than 10 minutes. Alternatively or additionally, said immediate response comprises a response within less than 2 minutes. Alternatively or additionally, said immediate response comprises a response within less than 20 seconds. Alternatively or additionally, said immediate response comprises a response within less than 2 seconds. Alternatively or additionally, said immediate response comprises a response within less than 0.5 seconds.

In an exemplary embodiment of the invention, said modifying is a transient modification temporally correlated with said applying.

In an exemplary embodiment of the invention, said modifying is a persistent modification lasting at least 10 times the length of said applying. Optionally, said modifying is a persistent modification lasting at least 100 times the length of said applying.

In an exemplary embodiment of the invention, said modifying comprises modifying a ratio between protein configurations of different activation levels of at least one of said at least one protein by a factor of at least 1.2. Optionally, said factor is at least 2. Alternatively or additionally, said factor is at least 5.

In an exemplary embodiment of the invention, determining a desired modification comprises determining a desired modification of tissue behavior. Optionally, said modification is a short term modification significant within 3 hours. Alternatively or additionally, said modification is a long term modification significant within 3 weeks. Alternatively or additionally, said modification is a long term modification which comprises changes in protein expression levels. Alternatively or additionally, said change is a change in at least 5 proteins associated with said behavior. Alternatively or additionally, said change does not include a change in expression of at least two housekeeping genes.

In an exemplary embodiment of the invention, determining a desired modification of tissue behavior comprises determining said modification for treating a disease. Optionally, treating comprises increasing contractility. Alternatively or additionally, treating comprises reversing a heart failure state in said tissue. Alternatively or additionally, said reversing comprises reversing on a cellular level. Alternatively or additionally, treating comprises normalizing protein expression levels. Alternatively or additionally, treating comprises normalizing protein activity levels. Alternatively or additionally, treating comprises skewing protein activity levels to compensate for said disease. Alternatively or additionally, treating comprises changing cellular homeostasis to a different set point. Alternatively or additionally, treating comprises modifying said treatment using a modification of protein activation levels as a target of said treating.

In an exemplary embodiment of the invention, modifying comprises changing a balance between activation and deactivation of a protein in said tissue.

In an exemplary embodiment of the invention, determining a desired modification of tissue behavior comprises determining said modification for assessing of tissue state. Optionally, said assessing comprises assessing based on said tissue response to said applying. Alternatively or additionally, said assessing comprises assessing based on a response of said tissue to said applying. Alternatively or additionally, said assessing comprises assessing based on tissue biochemical markers. Alternatively or additionally, assessing comprises classifying at least one of a disease state and disease severity. Alternatively or additionally, assessing comprises selecting a treatment according to said tissue response. Alternatively or additionally, assessing comprises assessing during an implantation procedure for a therapeutic device. Alternatively or additionally, assessing comprises assessing during a set-up stage for a therapeutic device. Alternatively or additionally, assessing comprises assessing as part of an on-going therapy using a therapeutic device. Alternatively or additionally, assessing comprises sampling said tissue for analysis thereof. Alternatively or additionally, assessing comprises selecting a placement for at least one electrode based on said assessing.

In an exemplary embodiment of the invention, said tissue comprises a tissue sample.

In an exemplary embodiment of the invention, said tissue comprises in-vivo tissue.

In an exemplary embodiment of the invention, said tissue comprises separated cells.

In an exemplary embodiment of the invention, said tissue comprises broken down tissue in which cells are broken down.

In an exemplary embodiment of the invention, said tissue comprises tissue homogenate.

In an exemplary embodiment of the invention, said determining a desired modification of tissue behavior comprises determining a modification for assessing a tissue response to stimulation.

In an exemplary embodiment of the invention, the method comprises modifying a selected field according to a response of said tissue to said applying. Optionally, said modifying a selected field comprises improving said field with respect to a desired effect of said field on said tissue.

In an exemplary embodiment of the invention, the method comprises programming a therapeutic device with said improved field.

In an exemplary embodiment of the invention, the method comprises measuring an immediate response of said tissue to said field.

In an exemplary embodiment of the invention, the method comprises measuring a non-immediate response of said tissue to said field.

In an exemplary embodiment of the invention, the method comprises measuring a non-local effect on remote tissue physiologically associated with said tissue in response to said field.

In an exemplary embodiment of the invention, said field is non-excitatory for said tissue.

In an exemplary embodiment of the invention, said tissue is contractile tissue and wherein said field reduces contraction of said tissue.

In an exemplary embodiment of the invention, applying comprises applying said field in conjunction with a pharmaceutical, which has an interaction with an effect of said field on said tissue.

There is also provided in accordance with an exemplary embodiment of the invention, apparatus for treating tissue, comprising:

at least one electrode adapted to apply a field to in-vivo tissue;

a controller including a memory having stored therein at least one electric field sequence which modifies protein activity levels in said tissue, said controller being configured to determine that a modification of said protein activity is desired and apply said sequence in response said determination. Optionally, said controller memory has stored therein a plurality of sequences or sequence parameters and wherein said controller is configured to select between the sequences or parameters. Alternatively or additionally, the apparatus comprises an input and wherein said controller makes said determination according to a signal received on said input.

There is also provided in accordance with an exemplary embodiment of the invention, a method of manufacturing a therapeutic device comprising:

selecting a pulse sequence according to its effect on protein activity modification; and programming a controller of said therapeutic device to apply said sequence.

There is also provided in accordance with an exemplary embodiment of the invention, a therapeutic device manufactured by the methods described herein.

There is also provided in accordance with an exemplary embodiment of the invention, a method of tissue treatment, comprising:

providing a plurality of tissue plugs;

applying an electric field to said plugs to modify biochemical behavior thereof; and implanting said plugs. Optionally, said plugs are cardiac tissue plugs.

In an exemplary embodiment of the invention, the method comprises excising said plugs from a same heart into which the plugs are later implanted.

In an exemplary embodiment of the invention, the method comprises genetically modifying said plugs prior to said implantation.

There is also provided in accordance with an exemplary embodiment of the invention, a method of therapy, comprising:

selectively applying a therapy material to a tissue; and selectively modifying protein activation in said tissue utilizing a second therapy. Optionally, said therapy material is gene therapy material and wherein selectively modifying comprises selectively modifying protein activity of a protein generated as a result of said therapy.

In an exemplary embodiment of the invention, said therapy material is a substrate for a protein and wherein selectively modifying comprises selectively modifying protein activity of said protein.

In an exemplary embodiment of the invention, selectively applying comprises making said substrate inaccessible to said protein.

In an exemplary embodiment of the invention, said therapy material increases the availability of a protein and wherein selectively modifying comprises selectively modifying protein activity of said protein.

In an exemplary embodiment of the invention, said second therapy comprises applying an electric field.

There is also provided in accordance with an exemplary embodiment of the invention, a method of modifying tissue behavior, comprising:

determining a desired modification of tissue behavior for at least one of treatment of a disease, short or long term modification of tissue behavior, assessing tissue state and assessing tissue response to stimulation;

selecting a tissue modifying activity having a known effect of modifying protein activation levels of at least one protein as an immediate response of a tissue to the activity, said known effect correlated with said desired modification; and applying said activity to said tissue.

In an exemplary embodiment of the invention, said activity comprises a pharmaceutical.

There is also provided in accordance with an exemplary embodiment of the invention, a method of modifying tissue behavior, comprising:

selecting a desired balance between a pair of agonist and antagonist reactions in a cell; and applying an electric field to said cell such that said field modifies an existing balance towards said desired balance. Optionally, said balance is a balance between phosphorylation and dephosphorylation.

There is also provided in accordance with an exemplary embodiment of the invention, a biochemical assaying kit, comprising:

an indicator of protein phosphorylation; and instructions for using said phosphorylation as an indicator of tissue state. Optionally, said instructions comprise software.

In an exemplary embodiment of the invention, said kit includes at least one electrode adapted to apply an electric field to a sample being tested with said kit.

In an exemplary embodiment of the invention, the kit includes a chamber and including a sampler adapted to remove a sample for assaying.

In an exemplary embodiment of the invention, the kit is adapted for use with a controller adapted to affect tissue in the body using an electric field.

In an exemplary embodiment of the invention, the kit comprises a plurality of indicators for a plurality of protein or mRNA expression levels.

There is also provided in accordance with an exemplary embodiment of the invention, apparatus for treating cardiac dysfunction, comprising:

at least one electrode adapted to apply an electric field to a patient; and a controller configured to apply an electrical sequence in spurts with delays between the spurts, said field being configured to have an affirmative modifying effect which modifies a behavior of said tissue in a positive manner, such that a lasting effect from a spurt continues for a significant time after the spurt. Optionally, said lasting effect has a wash-out period.

In an exemplary embodiment of the invention, a total effect of said controller is to modify protein expression levels in a heart of said patient.

In an exemplary embodiment of the invention, said lasting effect comprises enhanced tissue function of tissue to which said field is applied.

In an exemplary embodiment of the invention, said lasting effect comprises enhanced tissue function of tissue to which said field is not applied.

In an exemplary embodiment of the invention, said field is a non-excitatory field.

In an exemplary embodiment of the invention, said delay is at least 1 minute.

In an exemplary embodiment of the invention, said delay is at least 5 minutes.

In an exemplary embodiment of the invention, said delay is at least 10 minutes.

In an exemplary embodiment of the invention, said spurt is applied for less than a single heartbeat.

In an exemplary embodiment of the invention, said spurt is applied for less than 3 seconds.

In an exemplary embodiment of the invention, said spurt is applied for less than 10 seconds.

In an exemplary embodiment of the invention, said spurt is applied for less than 100 seconds.

In an exemplary embodiment of the invention, said field increases contractility.

In an exemplary embodiment of the invention, said controller is adapted to measure washout response to a spurt for said patient.

In an exemplary embodiment of the invention, said delay is at least 3 times a length of said spurt.

In an exemplary embodiment of the invention, said delay is at least 10 times a length of said spurt.

In an exemplary embodiment of the invention, said delay is at least 50 times a length of said spurt.

There is also provided in accordance with an exemplary embodiment of the invention, a method of treating a patient with an electrical therapy, comprising:
applying an electrical field to an organ of the patient;
stopping said application for a length of time which is a function of a washout time of an effect of said field.

In an exemplary embodiment of the invention, said organ is a heart and wherein said electric field enhances cardiac function.

In an exemplary embodiment of the invention, said organ is a heart and wherein said electric field enhances cardiac output on a level of a single heartbeat.

In an exemplary embodiment of the invention, said effect is an immediate effect. Alternatively or additionally, said effect is a short-term effect. Alternatively or additionally, said effect is a long-term effect.

There is also provided in accordance with an exemplary embodiment of the invention, a method of therapy location placement for therapy of tissue, comprising:
applying a test therapy to the tissue; and
deciding on suitability of the placement based on an effect of protein activity levels of said test therapy. Optionally, said test therapy is applied outside the body.

In an exemplary embodiment of the invention, said therapy is electrical therapy for the heart.

There is also provided in accordance with an exemplary embodiment of the invention, a method of therapy location placement for therapy of tissue, comprising:
providing an organ to be treated; and
selecting at least one location of treatment, according to a desired propagation of effect of said treatment in said organ. Optionally, said propagation is a mechanical propagation. Alternatively or additionally, said propagation is a biochemical propagation.

In an exemplary embodiment of the invention, said at least one location comprises a plurality of locations.

There is also provided in accordance with an exemplary embodiment of the invention, a method of therapy location placement for therapy of tissue, comprising:
applying a test therapy to the tissue; and
deciding on suitability of the placement based on an effect of protein activity levels of said test therapy, even if an improvement in organ function is not detected.

There is also provided in accordance with an exemplary embodiment of the invention, a method of therapy, comprising:
applying a therapy at a first location;
determining if the therapy is having a first effect by measuring a short term response at said first location; and
determining if the therapy is having a second effect by measuring a long-term response at a second, untreated, location. Optionally, the method comprises tracking progression of said therapy based on improvement of said second location.

There is also provided in accordance with an exemplary embodiment of the invention, a method of treating cardiac tissue, comprising:
selecting a tissue with reduced oxygen transport thereto; and
applying an electric field to said tissue, which field does not reduce activity thereof. Optionally, said field increases contractility of said tissue. Alternatively or additionally, said field reduces oxygen consumption of said tissue.

There is also provided in accordance with an exemplary embodiment of the invention, a method of assaying tissue state comprising determining biochemical activity, concurrently in relation to biochemical markers associated with at least two genes.

In an exemplary embodiment of the invention, the method comprises assessing tissue state in response to a therapy applied thereto.

In an exemplary embodiment of the invention, said assessing is in response to at least 5 markers concurrently. Alternatively or additionally, said assessing is in response to at least 10 markers concurrently. Alternatively or additionally, said assessing is in response to at least 20 markers concurrently. Alternatively or additionally, said markers include mRNA expression levels. Alternatively or additionally, said markers include protein expression levels. Alternatively or additionally, said markers include protein activity levels.

In an exemplary embodiment of the invention, the method comprises improving a therapy using said biochemical markers as a target.

In an exemplary embodiment of the invention, said biochemical markers include GATA-4.

In an exemplary embodiment of the invention, said biochemical markers include phosphorylation of phospholamban.

In an exemplary embodiment of the invention, said determining comprises determining an immediate effect.

In an exemplary embodiment of the invention, said determining comprises determining a short term effect.

In an exemplary embodiment of the invention, said biochemical markers include markers from at least two pathways in the tissue.

There is also provided in accordance with an exemplary embodiment of the invention, a kit adapted to perform the determining as described herein.

There is also provided in accordance with an exemplary embodiment of the invention, a method of treating cardiac dysfunction, comprising:

determining a desired effect on protein activity; and applying a field to cardiac tissue to cause such desired change.

In an exemplary embodiment of the invention, said desired effect comprises a selective effect on fewer than 5 proteins.

In an exemplary embodiment of the invention, said desired effect comprises a selective effect on fewer than 10 proteins.

In an exemplary embodiment of the invention, said desired effect comprises a selective effect on fewer than 40 proteins.

There is also provided in accordance with an exemplary embodiment of the invention, a method of treating cardiac dysfunction, comprising applying an electric field to said heart which is sufficient to have a significant normalization effect on protein phosphorylation levels without significant effect on contractility.

There is also provided in accordance with an exemplary embodiment of the invention, apparatus for delivering an electric field to cardiac tissue, being programmed to use a minimum amount of power sufficient to affect positively the phosphorylation of HF-related proteins.

BRIEF DESCRIPTION OF THE SEVERAL VIEWS OF THE DRAWINGS

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which:

FIGS. 3A-3E show the immediate effect of CCM signals on proteins in accordance with exemplary embodiments of the invention;

FIG. 8 shows levels of phosphorylated phospholamban in dog septum with heart failure with chronic treatment, in accordance with an exemplary embodiment of the invention.

DESCRIPTION OF SPECIFIC EMBODIMENTS OF THE INVENTION

Overview

Figure 1:
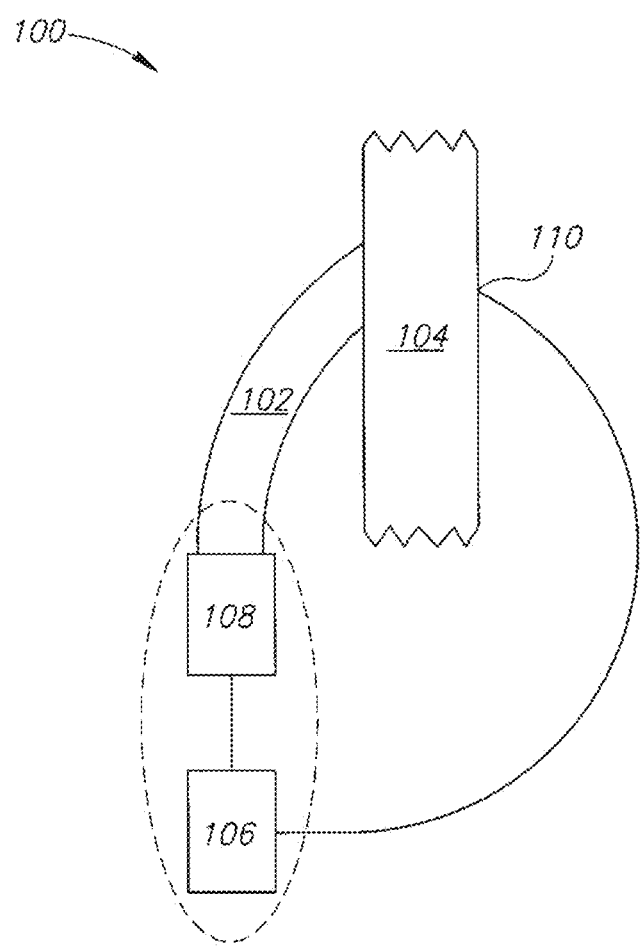
FIG. 1 is a schematic diagram of a tissue controller utilizing an electrical field to achieve a phosphorylation effect, in accordance with an exemplary embodiment of the invention.

Exemplary embodiments of the present invention are based on the discovery that certain electrical signals have an immediate effect on the phosphorylation of certain cardiac proteins, for example, at least one, at least 2, at least 3 or at least 5 proteins. Optionally, a set of proteins is affected, for example proteins that relate to calcium availability. In particular, an effect on proteins that control calcium pumping and others (all of which are known to change in heart failure), has been discovered. Selectively in which proteins were affected is also shown. Proteins not related to heart failure are apparently not affected. The effect has been found to work in a range of tissue organization levels starting from tissue homogenate, through isolated cells and even in in-vivo dog hearts. The effect remains (in dog hearts) for 15 minutes at least, and an initial effect is noticeable after as little as 1 minute or even a few seconds, such as 3-10 seconds, for tissue samples from a foci of signal application. Some proteins were phosphorylated and some were unphosphorylated by the signal. Generally, the results show a change in the phosphorylation values in a direction of "normal" levels, or their being maintained at normal values. Experiments using pacing signals have not shown this effect.

This phosphorylation effect is optionally in addition to or instead of effects on mRNA expression and protein expression levels, which, in some embodiments of the invention are normalized, changed to more normal values and/or changed in a manner which overcompensates for a deficit.

In accordance with exemplary embodiments of the invention, this discovery is used in the design of methods and apparatus for treating tissue, especially cardiac tissue.

For purposes of this specification and the accompanying claims, the terms "expression" and "regulation" should be construed in their broadest possible sense so that they include any factor which influences a biological activity. Thus expression and/or regulation include, but are not limited to factors such as control exercised at the genomic DNA level, the RNA level, the protein level and secretion level.

With regard to genomic DNA, control may be exercised, for example, by altering a phosphorylation and/or a methylation state at one or more sites in a relevant genomic sequence.

With regard to RNA, control may be exercised, for example, by regulating a rate of transcription of an mRNA transcript, and/or by altering a stability of an mRNA transcript, and/or by altering a relative amount of splice variants from a single mRNA transcript.

With regard to protein, control may be exercised, for example, by regulating one or more cleavage events and/or addition of one or more side chains and/or protein stability. In some cases cleavage of a protein may increase a biological activity of the protein and/or facilitate secretion from a cell. In other cases, cleavage of a protein may reduce or eliminate activity of the protein. The term side chains, as used herein, denotes any molecular moiety which can be attached to an amino acid of the protein. In some cases, side chains are attached after translation. In other cases a tRNA molecule may attach an amino acid bearing a side chain during translation.

With regard to secretion, control may be exercised, for example, by allowing or preventing of secretion of compounds, such as connective tissue dissolving enzymes and biochemical signaling molecules.

Schematic Device

FIG. 1 is a schematic diagram of a tissue controller 100 utilizing an electrical field to achieve a phosphorylation effect, in accordance with an exemplary embodiment of the invention. In an exemplary embodiment of the invention, controller 100 comprises at least one electrode 102 adapted to apply an electric field to a tissue 104, for example a heart. A control circuitry 106 optionally controls the output of a power drive 108 which electrifies the at least one electrode 102. One or more optional physiological sensors 110 optionally provide feedback to be used by circuitry 106 in controlling the electrification of the at least one electrode 102, for example, general feedback about the heart (e.g., ECG) and/or a micro-biological sensor, for example for mRNA expression profiles or protein activity level. Optionally, such sensors include fiber-optic anti-body based sensors, DNA or protein chips and/or lab-on-chip type sensors.

In an exemplary embodiment of the invention, controller 100 is in the form of a pacemaker or non-excitatory controller, for example as described in one or more of the following applications and publications.

Exemplary protocols for the actual delivery of signals to the heart and/or implantation of wires to deliver CCM signals is set forth in PCT publication No. WO 97/25098 and U.S. Pat. No. 6,317,631, both of which are incorporated herein by reference in their entirety. Following is a list of patents and publications which describe apparatus and methods which may be useful in conjunction with the present invention, the disclosures of all of which are incorporated herein by reference, as are the disclosures of all publications mentioned in this application:

Cardiac output enhanced pacemaker, U.S. Pat. No. 6,463,324, Apparatus And Method For Controlling The Contractility Of Muscles, U.S. Pat. No. 6,233,484, Controlling Heart Performance Using A Non-Excitatory Electric Field, U.S. Pat. No. 6,317,631, Muscle Contraction Assist Device, U.S. Pat. No. 6,285,906, Modulation Of Intracellular Calcium Concentration Using Non-Excitatory Electrical Signals Applied To The Tissue, PCT WO01/24871 and PCT WO00/12525, Electrical Muscle Controller, U.S. Pat. No. 6,363,279, Electrical Muscle Controller using a Non-Excitatory Field, U.S. Pat. No. 6,330,476, Cardiac Output Controller, U.S. Pat. No. 6,298,268, Cardiac Output Enhanced Pacemaker, U.S. Pat. No. 6,463,324, Sensor Based Regulation of Excitable Tissue Control of the Heart, WO00/27475, Regulation of Excitable Tissue Control of the Heart based on Physiological Input, WO00/27476, Trigger Based Regulation of Excitable Tissue Control of the Heart, U.S. Pat. No. 6,587,721, Pacing with Hemodynamic Enhancement, PCT IL99/00392, ETC Delivery via RV Septum, PCT WO0182771A3, Anti-Arrhythmia Device having Cardiac Contractility Modulation Capabilities, PCT WO01/30445, and Anti-Arrhythmic Device & a Method for Delivering Anti-Arrhythmic Cardiac Therapy, PCT WO01/30139.

In an exemplary embodiment of the invention, controller 100 includes a memory in which various measured and/or expected values and behaviors of tissue and bio-chemicals are stored. Controller 100 may be implanted, only the electrodes implanted or be wholly outside the body, optionally only with a sensor implanted, optionally with a sensor inserted as needed.

Controller 100 optionally provides one or more of the therapeutic effects listed following this paragraph. Optionally, when two or more effects are provided, the effects are provided simultaneously or alternately (e.g., alternating or otherwise intermixed electrification signals to have the multiple desired effects). In some cases, the behavior of the controller is modified to provide a tradeoff between multiple effects. Some of the effects may be enhanced and/or caused by modification of protein activity and/or mRNA expression. In some cases, the sequences used for "standard" effects are modified so that desired biochemical effects as described herein are achieved. Such modification may be by per patient optimization or by off-line general quasi-optimization independent of any particular target patient. Optionally, the controller is programmable, for example, using outside programming to perform one or more of the following therapies, as described elsewhere:

a) pacing;
b) contractility enhancement;
c) cardiac resynchronization;
d) conduction velocity modification;
e) remodeling;
f) arrhythmia treatment and/or prevention;
g) healing of diseased cardiac tissue; and
h) stabilizing cardiac condition.

Phosphorylation Modification

As noted above and as will be described below, it has been discovered that pulses originally designed for cardiac contractility modification (CCM) have an immediate and/or a long range effect on genomic expression (e.g., as evidenced by mRNA expression) and/or on protein activity. However, it is believed that other pulses also have such effects. In particular, CCM pulses often require a certain timing, which may not be required for some phosphorylation effects. In particular also, CCM pulses may need to be applied more often for significant CCM effects than for significant phosphorylation effects. In particular also, phosphorylation effects may be achieved even when CCM or at least contractility increase is reversed or null or fluctuates. In particular also, phosphorylation effects may also be achieved using excitatory signals or a combination of excitatory and non-excitatory signals and not only with pure non-excitatory signals.

In an exemplary embodiment of the invention, within seconds of applying the electric field to the tissue in-vivo or in-vitro, existing phospholamban protein is phosphorylated, without the need to synthesize more protein, but rather making use of what is already there in a "dephosphorylated state".

In an exemplary embodiment of the invention, one or both of between beat and within beat phosphorylation levels are controlled. For example, to reduce inter-beat effects, phosphorylation increase is kept at a level which cellular homeostasis mechanism can counteract by the next time a field is applied. In some cases, this requires one or both of control of field amplitude and frequency of application.

Optionally, different proteins are differently controlled, for example intra-cellular and trans-membrane proteins.

Figure 4:
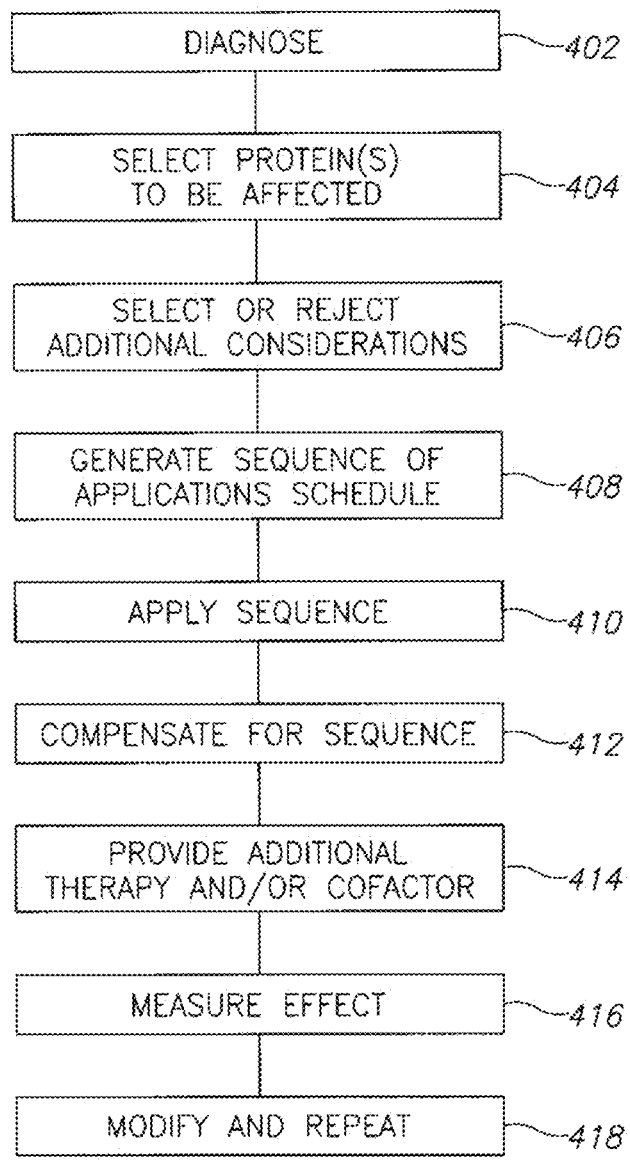
FIG. 4 is a flowchart of a method of therapy taking phosphorylation into account, in accordance with an exemplary embodiment of the invention.

FIG. 4 is a flowchart of a method of therapy taking phosphorylation (or other biochemical change) into account, in accordance with an exemplary embodiment of the invention.

At 402 a diagnosis of a patient is optionally made. Optionally, the patient is re-diagnosed as his therapy advances.

At 404, one or more proteins to be affected by the electrical signals are selected. Optionally, the proteins are selected based on the diagnosis. Optionally, a set of related proteins, for example, calcium availability proteins, are selected. Optionally, one or more locations in the heart to be affected are selected. Optionally, target protein, mRNA and/or phosphorylation levels and/or other tissue or organ effects are selected.

At 406, additional considerations are selected and/or rejected. In one example, the additional consideration is that the heart be paced and/or its LVEF (left ventricular ejection fraction) be increased. In a different example, considering that the pulses may be applied less often than pacing pulses, more painful treatments, such as external pulses, are used. Optionally, pro-arrhythmic pulses are used, for example, if the treatment is under a hospital setting or if the treatment is infrequent enough so that the total danger of arrhythmia over a time period is within acceptable parameters. Controller 100 optionally includes a defibrillation and/or fencing function applied through the same or other electrodes. In an exemplary embodiment of the invention, immediate reduction in cardiac efficiency is acceptable, as this is under controlled conditions and increased cardiac health will follow shortly (e.g., within minutes, hours, days or weeks).

In another example, a protein modifying signal is applied as an exciting signal. In another example, a protein modifying signal is applied in parts of the cardiac cycle where it reduces contractility (or dP/dt) and/or prevents normal signal propagation in the heart. Optionally, the part of the heart to which the signal is applied is decoupled or deactivated, for example, by cold, by fencing or by various cardioplegia drugs.

In an exemplary embodiment of the invention, it is assumed that the protein modification signal has an effect that is at least partly independent of the point in the cardiac cycle at which it is applied, at least for some proteins, such as proteins that are not electrically sensitive to the electrical cycle in the cell. For example, the effect depends on the availability of ATP for phosphorylation and not on the particular charge conditions in the cell. For some applied signals, the ion concentrations may have an effect on the efficacy of the signal and these may be dependent on the phase in cell depolarization/repolarization cycle. In an exemplary embodiment of the invention, the effect of a particular sequence and/or for a particular patient is taken into account when deciding on the strength and/or other parameter of a signal.

In an exemplary embodiment of the invention, it is assumed that a CMM-type signal has multiple effects on cardiac tissue which may be targeted separately, at least to some extent. Some effects are causative, but may be at least partially decoupled or require multiple inputs to generate a particular desired result. Some of the effects are:

a) Effect on tissue polarization. This may include, for example, hyper-polarization, pacing and depolarization.

b) Effect on repolarization/depolarization cycle. This may include, for example, extending a plateau duration.

c) Effect on tissue function (external), for example, increased contraction strength and inhibition of mechanical and/or electrical activity.

d) Effect on protein phosphorylation.

e) Effect on genomic expression.

f) Short vs. long term effects (e.g., remodeling).

At 408 a pulse sequence and/or application schedule (e.g., once a week) are optionally generated or selected, for example, using a look-up table or by searching for a solution. Many optimization and search methods are known in the art and may be used to help determine a treatment protocol; for example, linear programming, hill climbing and trial and error experimentation (e.g., manual or automatic experiments). The particular characteristics of the tissue and/or patient may also be determined, for example, by experimentation or by a table linking disease type to an expected (and/or desired) effect of a change in the protocol. The generation is optionally performed on controller 100. Optionally, the generation is at a treatment center, for example, if the patient comes in periodically for treatment or, if treatment is by remote means, by using a telephone link to control an implanted or external field source.

At 410, the sequence is applied to the tissue.

At 412, compensation for the effects of the sequence may be provided, if necessary, for example, anti-arrhythmia treatment or oxygen provision. Optionally, the compensation is provided before and/or during the sequence application, or intermingled therewith.

At 414 an additional therapy and/or cofactor are optionally provided, which optionally interact synergistically with the sequence, for example, on a cellular level or by one assisting the other to have an effect. In one example, the additional therapy is pharmaceutical. In another example, the additional therapy provides a cofactor or substrate which the proteins need to change their activity level. In another example, DNA therapy is made more specific by the proteins being generated and/or being activated by the field. In another example, exercise or rest is enforced so as to build-up a supply of substrate (e.g., protein or phosphor) on which the field can have an effect.

At 416, the effect of the field is optionally measured. Optionally, the measurement is in substantial real-time. In an exemplary embodiment of the invention, a gene or protein chip are used to detect protein, phosphorylation and/or mRNA levels. Alternatively or additionally, an optical sensor is used, for example an anti-body carrying optical detector. Optionally, the sensor is consumable and lasts, for example, for 5, 10, 20 or 100 uses (e.g., a multiple of single use sensors may be supplied). Optionally, spectroscopy methods are used, for example, Raman spectroscopy.

While phosphorylation may be measured directly, optionally, cellular and/or organ behavior characteristics are measured instead, for example, stroke volume and effect on ECG.

At 418, the sequence is optionally repeated, optionally being modified according to the obtained results.

Optionally, multiple feedback loops are maintained, for example, some parameters being measured on a second by second or minute by minute basis and others being measured on an hourly, daily, weekly and/or monthly schedule.

Optionally, the measurements are off-line, for example, by biopsy taking. Optionally, the sample is frozen, for example in liquid nitrogen, to prevent changes. The results are optionally transmitted to controller 100.

In an exemplary embodiment of the invention, the intended effect of the electrical therapy is to tip a balance between phosphorylation and dephosphorylation mechanisms in the cell. For example, the electric field can be applied so that a protein (such as calcium channel) is more easily phosphorylated, while dephosphorylation mechanisms stay the same (or vice-versa). This can cause both an immediate (intra-beat) effect on phosphorylation levels and depending on the ratio between the immediate effect and the dephosphorylation mechanism, can cause a longer term increase.

In some cases, the long term increase is carried past normal levels, for example, to force a certain operation state of the controlled tissue.

In an exemplary embodiment of the invention, the electrical modification of proteins is used to achieve an effect that does not directly translate into long term changes in protein levels.

In an exemplary embodiment of the invention, the electrical modification is used to trigger a change in cellular state. For example, once certain cellular balances are upset, cellular mechanism will then change the operational mode of the cell in a desired manner.

In an exemplary embodiment of the invention, the electrical modification is used to support a failing cellular mechanism so that the cell can recover.

In an exemplary embodiment of the invention, the electrical modification is used to damp or overcome an over-protective or run-away protection/control mechanism. One example, in cardiac cells, is a mechanism that when the cell feels over stressed, reduces contractility so that the cell can funnel its resources to viability. The electrical modification can be used to suppress this mechanism, so that contractility can resume, especially if the cell is actually capable of contraction and such contraction is suppressed or reduced by a run-away mechanism. Optionally, if there is a degradation in function, for example as detected by reduction in cardiac output or degraded ECG signals, the protein modification is stopped and is used as an indication that the cellular protection mechanism was not actually being over protective.

Exemplary Considerations for Pulse and/or Schedule Design

Further to the examples above, following are exemplary considerations to be taken into account during sequence and/or schedule design. In particular, pulse length, power, shape, intra-pulse delay, repetition rate and/or delay between sequences may be modified and/or optimized to have a desired effect (or mainly such a desired effect).

a) Pulse rate and length. Protein specificity is optionally achieved based on one or both of length of each pulse and delay between pulses. As noted, some proteins are significantly affected by short pulses. Such a protein can be selectively affected by using shorter pulses than needed for other purposes, and repeating the pulses at inter-pulse delays shorter than a relaxation time for the affected protein. Optionally, proteins are targeted based on their location in the cell and the type (e.g., amplitude, frequency and/or waveform) of pulse that is expected to penetrate sufficiently into the cell and/or affect the particular protein. Optionally, pulse rate and/or delays and/or length are modified as needed to achieve a target. This allows for targeting the effect to a limited number of proteins.

b) mRNA vs protein effects. In an exemplary embodiment of the invention, mRNA and/or protein effects are selected by applying pulses which have a short term effect on proteins but the effect is not long enough to trigger significant mRNA expression effects. For example, if a protein phosphorylation level is not elevated for long enough, it may be that mRNA effects will be absent. However, phosphorylation may be increased multiple discrete times (with delays between them). In accordance with some embodiments of the invention, some mRNA effects are directly determined by proteins, so that protein levels may be controlled in order to achieve selective mRNA effects.

c) Counter effects. In an exemplary embodiment of the invention, the control is selected so that mRNA effects and phosphorylation effects are not synchronized. For example, long plateaus of increased phosphorylation may be used to increase mRNA effect, but total phosphorylation modification may be selected to be insignificant over a time period. One reason for this may be lack of sufficient blood flow to the heart, so that acute changes are less desirable than gradual changes. In another example, pharmaceuticals which counteract an effect may be provided to effectively select certain effect(s). It is noted however, that phosphorylation changes associated with increased contractility did not show increased oxygen demand, in some experiments at least and in at least one experiment, even reduction in oxygen demands.

d) Stability. Optionally, the long term effect of treatment is a new balanced set point between the various proteins. However, in the short term, such a balancing need not be achieved. Optionally, the heart is controlled so that the various proteins are not at a balance with regard to their respective activities.

In general, short term effects and long term effects may be at odds.

Exemplary Pulse Properties

While CCM pulses as described herein may be used, optionally, the pulses used are modified, for example, to save power and/or reduce the need for synchronization.

In an exemplary embodiment of the invention, the applied pulses and/or sequences require considerably less power than CCM signals (e.g., 7.73 volts for 33 ms each 45 seconds), for example, only 20%, only 10%, only 5%, only 1%, or intermediate or smaller power usage.

In an exemplary embodiment of the invention, the amplitude and/or duration used is insufficient for contractility, for example, being under the amount (if any) which causes a 20%, 10%, 3%, 2%, 1% or intermediate or smaller increase in contractility over a period of 5 minutes from initial application. For example, the application rate, power and/or duration are smaller.

In an exemplary embodiment of the invention, the voltage used is lower than for CCM, for example, being 0.1, 0.5-1 volts, or less, or values such as 2V or 3V or other values smaller than 8 Volts. It should be noted that in the results shown below, the CCM signal was clearly more than required to achieve a meaningful phosphorylation, and thus a signal less powerful may be suitable. Larger voltages such as 10, 20 or 30 volts may be used in some embodiments.

In an exemplary embodiment of the invention, the duration of the pulses is as short as 1 ms (with an optional associated increase in power), or longer, such as 10 ms, 20 ms or more. Alternatively, the signal may be lengthened, for example, being 50, 100, 150, 200, 300, 400 ms or more. Optionally, medication which increases a refractory period is used in conjunction with long pulses. Optionally, fast and short term acting medication is used during pulse application.

In an exemplary embodiment of the invention, a total charge carried by a phosphorylation pulse is at least 5, 10, 30, 50 or 100 times the charge carried by a pacing pulse, such as a 3V 0.75 ms pulse.

High power pulses are optionally applied as sub-threshold (for excitation) pulses.

In an exemplary embodiment of the invention, the current for the pulse is between 0.2 ma and 20 mA, or intermediate or higher values. Other exemplary values for current (maximum current) are 0.4, 0.8, 1, 3, 7 or 10 mA (or intermediate values).

In an exemplary embodiment of the invention, the applied signal comprises a series of pulses, for example, each pulse being bi-phasic, with each phase being 5.5 msec (~100 Hz), applied in synchronization with a local pacing activity (e.g., at a delay thereto). Optionally, the series is of 2-3 pulses, or a larger number, for example, 5, 10, 20 or more or intermediate numbers.

Other waveforms can be used, for example, sinus waves or triangular waves. Optionally, a delay is provided between pulses of a series. Optionally, a pulse includes both excitatory and non-excitatory components.

In an exemplary embodiment of the invention, signals applied outside the absolute refractory period are applied at lower amplitudes. The relevant thresholds are optionally determined by experimentation or using standard values (noting that diseased tissue may have a lower threshold and/or abnormal refractory periods. Optionally, medication is provided to extend the refractory period and allow a greater charge and/or longer pulse sequence to be delivered during a single beat.

In an exemplary embodiment of the invention, a tune-up of the pulse parameter is carried out, for example, to enable power to be reduced to a minimum which has an effect and/or as the patient response changes.

In an exemplary embodiment of the invention, the application schedule includes reducing the number of applied sequences and/or increasing the delay between them. For example, as shown below, a 1 min application has an effect even after 15 minutes. Thus, it is expected that a short application, for example, 20-60 seconds can be used to maintain more normalized phosphorylation levels for many minutes, for example, 15, 20, 40, 60 minutes or more. Optionally, a small number of spurts can thus be used to maintain relatively "normalized" levels for many hours, such as 1, 2, 4, 6, 10, 12, 24 or more per hour (e.g., one spurt for each beat or small number of beats such as 2, 5, 10, 20 or intermediate numbers).

Genes and Related Proteins

Following is a partial list of genes (and corresponding proteins) whose expression is correlated with some types of heart failure (termed "heart failure" in short below). In an exemplary embodiment of the invention, treatment is configured so that a particular gene/protein will be affected in a desirable manner. It is noted that in accordance with some embodiments of the invention, different heart failure states are identified based on the protein expression, mRNA expression and/or protein activity profiles; or based on changes in such profiles in response to treatment, for example, immediate response or longer term response (e.g., hours, weeks or months). The treatment may target particular proteins, pathways or groups of proteins, for example, SR proteins. Optionally, the treatment aims to undo the negative effects described below, for example, by modifying the protein level and/or activity. Optionally, analysis and/or treatment relates simultaneously to several genes, for example a set of two, a set of three, a set of five or sets of other numbers of genes, for example genes selected form the list below. Optionally, the set includes genes from at least two or from at least three different gene type classifications. A profile used for assessment can include, for example, 1, 2, 3, 4, 5 or more markers from each of the types of mRNA, protein and protein activity.

Various Genes a) ANP=atrial natriuretic peptide or A-type natriuretic peptide, is increased in heart failure. The increase in ANP is related to increased atrial enlargement and stretch which is bad. Increased ANP correlates with increased mortality and morbidity in heart failure.

b) BNP=Brain natriuretic peptide or B-type natriuretic peptide is increased in heart failure. BNP is elaborated from ventricular tissue. The increase in BNP is due largely to increased LV size and stretch which is bad in heart failure. Increased BNP in heart failure correlates with increased mortality and/or morbidity. BNP is also a member of the so-called "fetal gene program" which also negatively impacts heart failure.

c) GAPDH. This is a gene whose expression does not change in heart failure and is used as "a housekeeping gene" to ensure good quality RNA extraction. If the expression of this gene changes during RT-PCR this may indicate poor RNA quality and the results of all other gene expression measurements may become questionable.

SR Genes d) RYR2=ryanodine receptors also referred to as sarcoplasmic reticulum calcium release channels. These channels control the release of calcium from the sarcoplasmic reticulum. This is the calcium signal that is needed to activate the contractile apparatus (actin myosin cross bridging). These channels are hyperphosphorylated in heart failure and turn very active and, therefore, are "leaky," leading to possible calcium overload which is bad for the heart muscle cell. Reducing or normalizing phosphorylation may be desirable for these proteins.

e) NCX=sodium calcium exchanger. Under normal conditions, the NCX takes calcium out of the cell in return for Na. This maintains calcium homeostasis and prevents calcium overload which is bad for muscle cell function and survival. In heart failure the NCX is increased and is hyperphosphorylated and may begin to work in what is called "reverse mode", to compensate for reduced SERCA-2A activity, and may cause calcium overload (=diastolic dysfunction). Too much activity in forward mode depletes SR calcium (=systolic dysfunction).

f) PLB=Phospholamban. This is an essential sarcoplasmic reticulum protein. Under normal conditions PLB is phosphorylated. When that happens it activates SERCA-2a (calcium ATPase) which then pumps calcium from the cytosol into the SR and thus prevents calcium overload. PLB is decreased in heart failure and is dephosphorylated. Because of that, SERCA-2a activity is reduced and it is less able to pump calcium back into the sarcoplasmic reticulum. This leads to calcium overload. When the SR has reduced calcium, there is less calcium release through the calcium release channels and contractility decreases.

g) SERCA-2a=calcium ATPase. This sarcoplasmic reticulum (SR) pump, under normal conditions, pumps calcium from the cytosol into the SR. In heart failure SERCA-2a decreases dramatically and its activity also decreases leading to calcium overload and poor intracellular calcium cycling. This decreases contraction strength.

h) Calsequestrin (CSQ). Clasequestrin is an SR protein involved in calcium sequestration and does not change in heart failure. Because it does not change in heart failure, it is frequently used as a housekeeping gene. It may also be used to normalize when samples are inconsistent in the loading process.

Matrix Metalloproteinases (MMPs)

i) MMP1. This gene is involved in the degradation of connective tissue at all levels and, for this reason, its elevation in heart failure is not desirable and counteracted in some embodiments of the invention.

j) MMP2 and MMP9. These are referred to as to as "gelatinases". Inhibiting gelatinases in the setting of heart failure appears to be helpful particularly with respect to reducing "interstitial fibrosis" or the accumulation of connective tissue or collagen in the cardiac interstitium. Reducing interstitial fibrosis leads to improved LV diastolic compliance and, hence, improved diastolic filling and function.

Stretch Response Genes

Stretch response genes are up-regulated in the presence of progressive LV dilation and myocytes stretch as occurs in heart failure. The importance of these genes is they trigger maladaptive cardiomyocytes hypertrophy which then leads to abnormal calcium cycling.

k) p38=p38 alpha-beta mitogen activated protein kinase. This is a stretch response gene. Its expression increases in heart failure and that can lead to many abnormalities including the development of hypertrophy and activation of multiple transcription factors that lead to activation of the fetal gene program. An increase in P38 correlates with maladaptive hypertrophy and ventricular enlargement. This indicates a bad prognosis for heart failure.

l) p21 ras=This is also a stretch response gene. Its expression increases in heart failure due to ventricular enlargement and stretch. When stretch and wall stress increases in heart failure, these mechanical factors increase a family of cell surface proteins known as integrins. Integrins, when activated, lead to increase in p21 ras and p38 and both lead to maladaptive hypertrophy.

m) Integrin-a5. This is a cell surface receptor gene whose protein acts as a mechanical transducer. It is activated in response to mechanical stretch or stress mediated by LV dilation. When activated, it promotes regulation of stretch response protein. Down regulation of this gene in heart failure is a desirable feature of some embodiments of the invention.

Fetal Program Genes n) Alpha-MHC=alpha myosin heavy chain is reduced in heart failure. Because the alpha isoform of MHC is the isoform responsible for increased velocity of shortening of cardiac muscle cells, a reduction in alpha MHC impacts negatively on function/contraction of the failing ventricle. Alpha MHC restoration is associated (and optionally provided by some embodiments of the invention) with LV contraction improvements.

o) Beta1-Adrenergic Receptor. This gene is down-regulated in heart failure. Drugs such as metoprolol which are selective beta-1 receptor blockers which up-regulate the beta-1 receptor improve mortality and morbidity in heart failure and appear to also improve, albeit in a limited way, exercise tolerance. Up-regulation of this gene is viewed as a positive development in some embodiments of the invention which enhances the sensitivity of the contractile element of catecholamines.

SERCA-2a, mentioned above, is also a member of the so-called fetal program gene.

Experimental Results—Long Term ("Chronic") and Short Term (Several Hours)

Before describing experiments in which an immediate effect was discovered on phosphorylation, experiments on relatively long term effects will be described, including effects that occur (at least to a significant degree) after a few hours of continuous CCM application and after 3 months. These experiments generally show that LV function in dogs with HF improves without an associated increase in $MVO_2$.

Where mentioned, CCM is a pulse at 80 applications per minute (synchronized to a heart beat, if any), at 7.73 Volts, with between 4 and 6 phases, each phase being 5.56 ms long and being continuous and of opposite polarity of a previous phase. The number of phases was not changed within an experiment. The signal was generally applied to a septum, from a right chamber, with a distance of 1-2 cm between an electrode pair used to apply the signal.

The marking "NL" indicates normal tissue levels.

In a first set of experiments, 6 dogs that had micro-embolization induced HF were used. The CCM signal was a 7.73 volt, epicardial LV anterior wall signal. The definitions for the various variables follow Circulation Research 91:278, 2002, the disclosure of which is incorporated herein by reference.

Figure 2A:
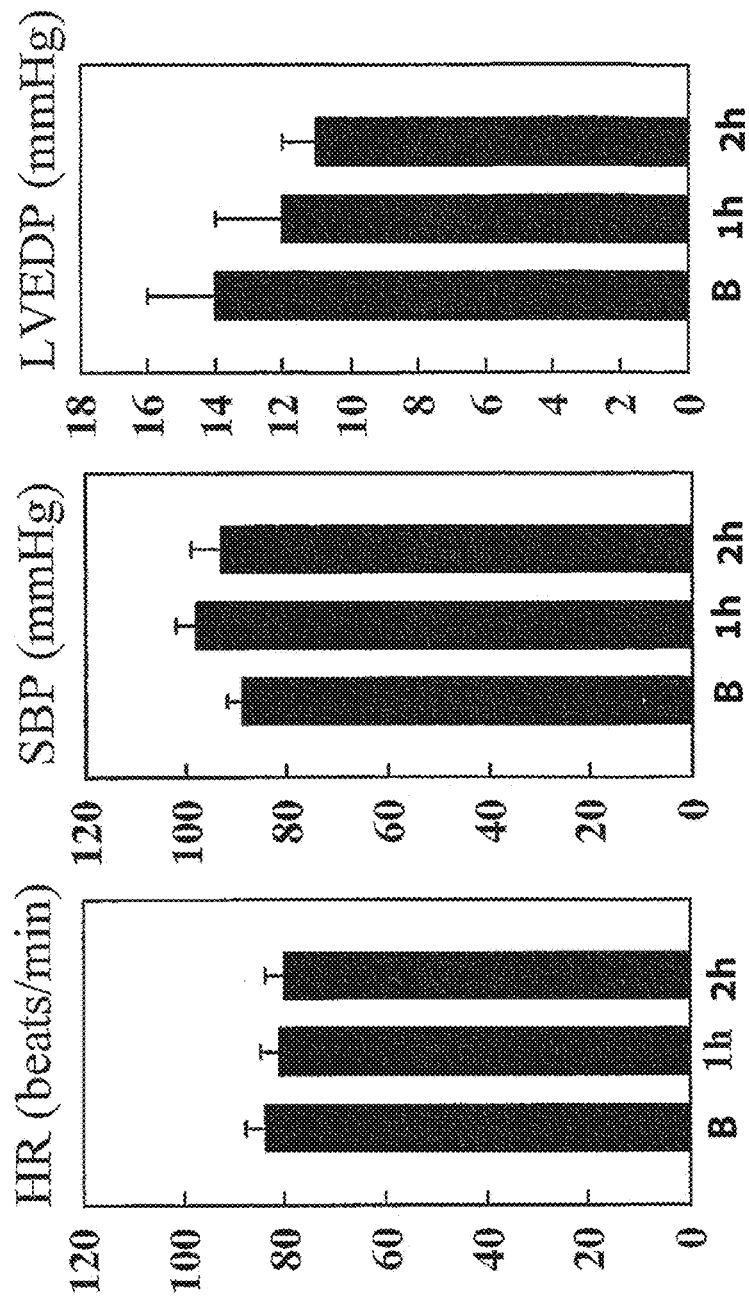
FIGS. 2A-2O show the effect of a short term or chronic (multi-month application period) CCM signal on proteins and mRNA in the heart, in accordance with an exemplary embodiment of the invention.
Figure 2B:
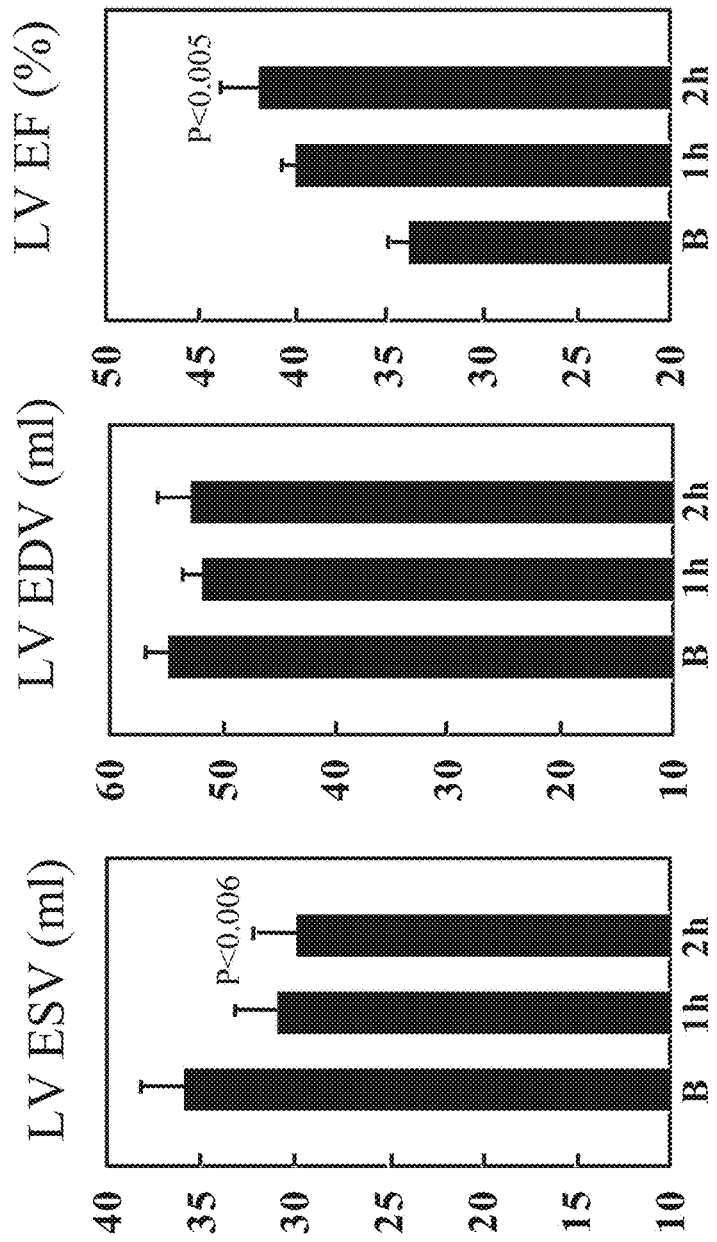
Figure 2C:
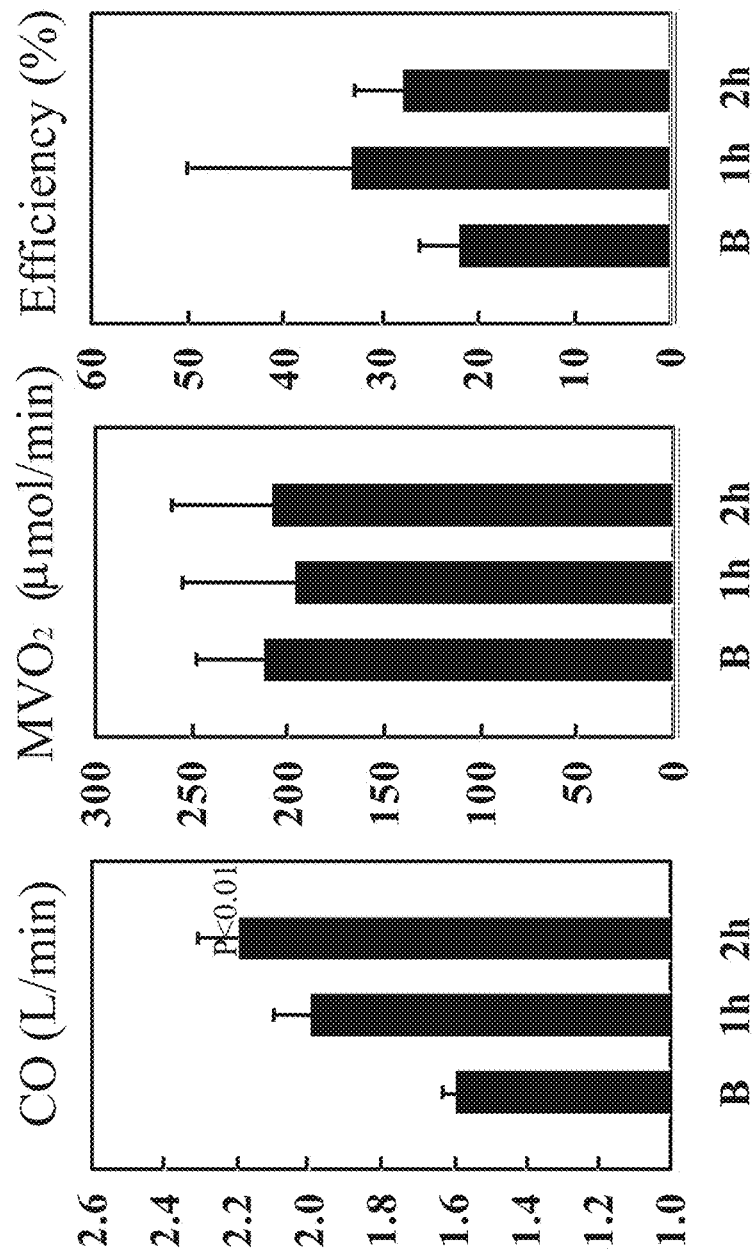
Figure 2D:
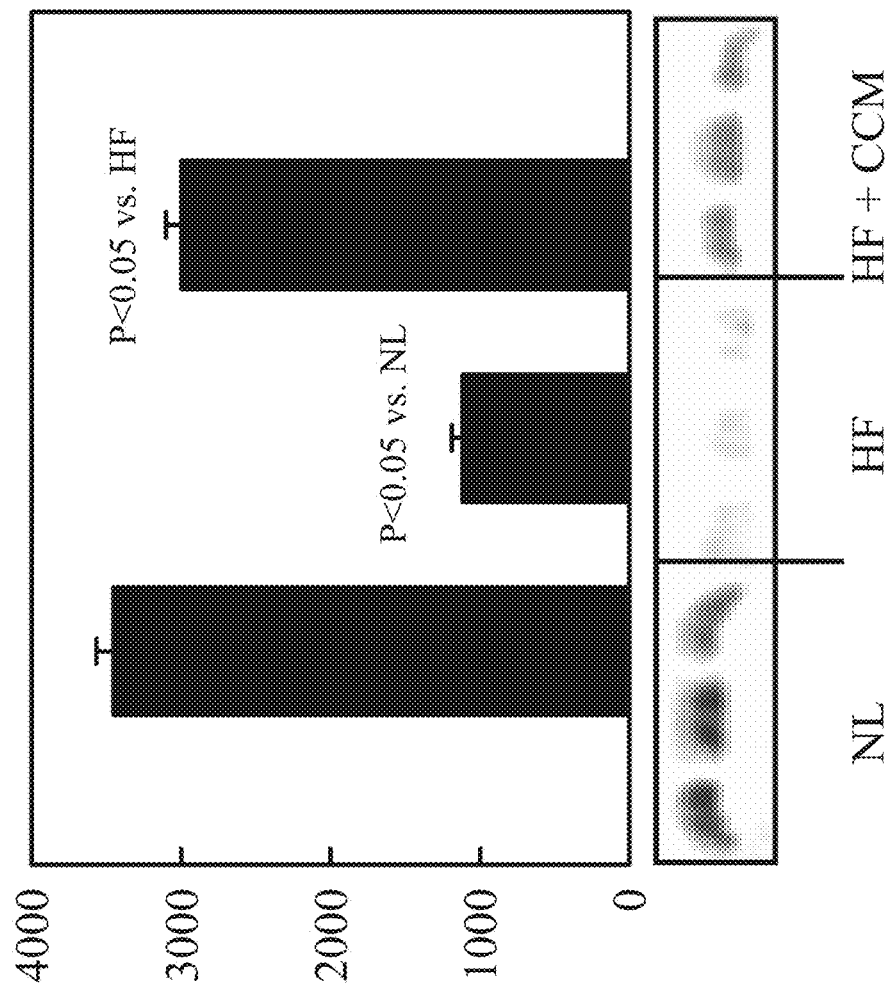
Figure 2E:
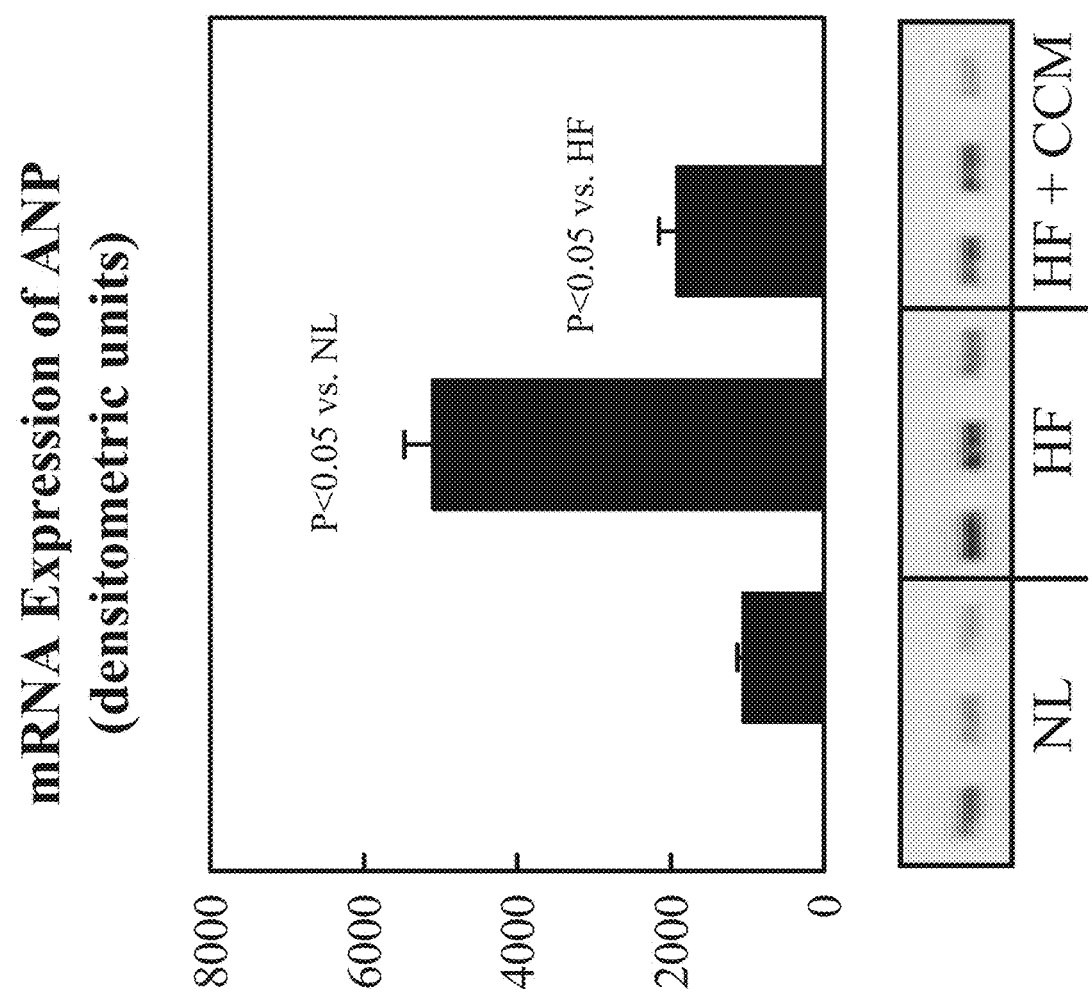
Figure 2F:
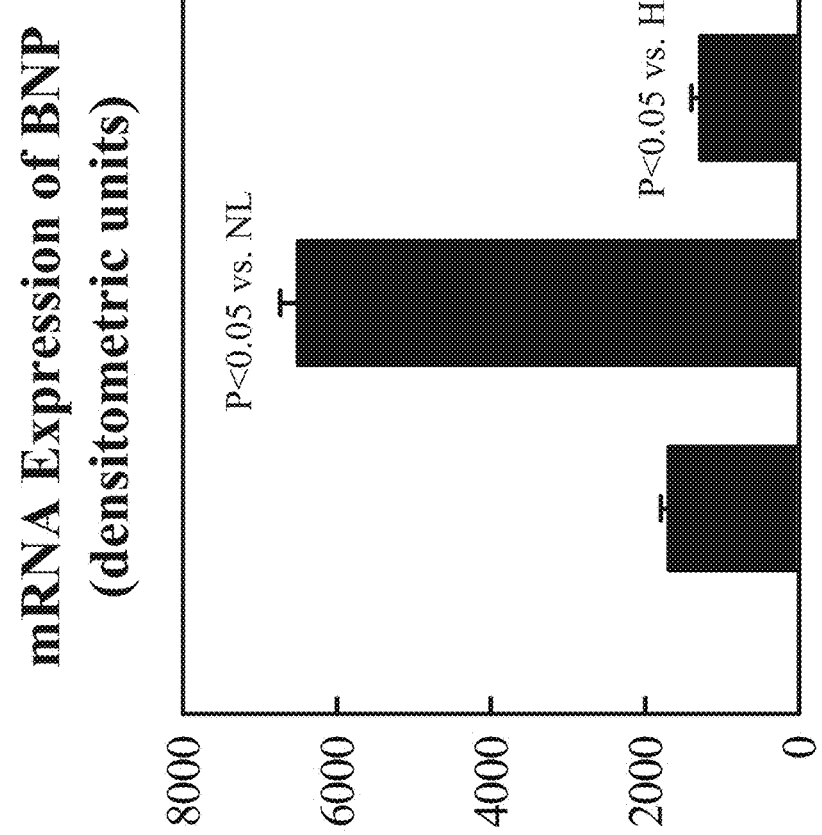

FIGS. 2A-2C show the improvement of LV function without $MVO_2$ increase, in CCM treated dogs as a function of time and compared to baseline values.

FIGS. 2D-2G show changes in mRNA expression of alpha-MHC, ANP, BNP and SERCA-2a in normal, HF and HF dogs with CCM treatment respectively, after several hours of treatment.

As will be shown below, effects on protein phosphorylation (at least) can be shown after a short time.

Figure 2H:
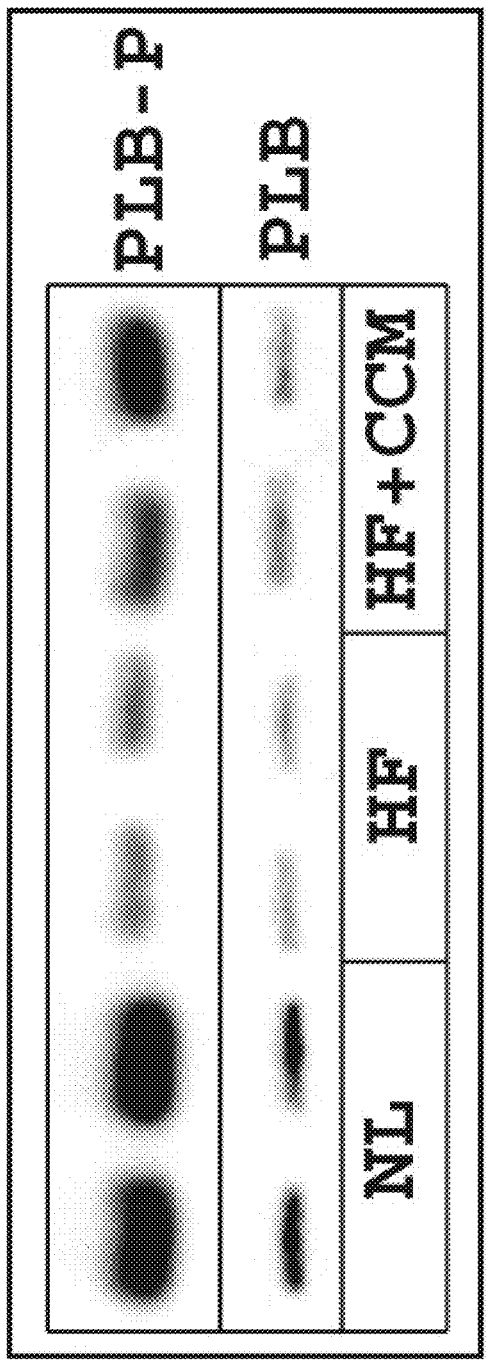
Figure 2I:
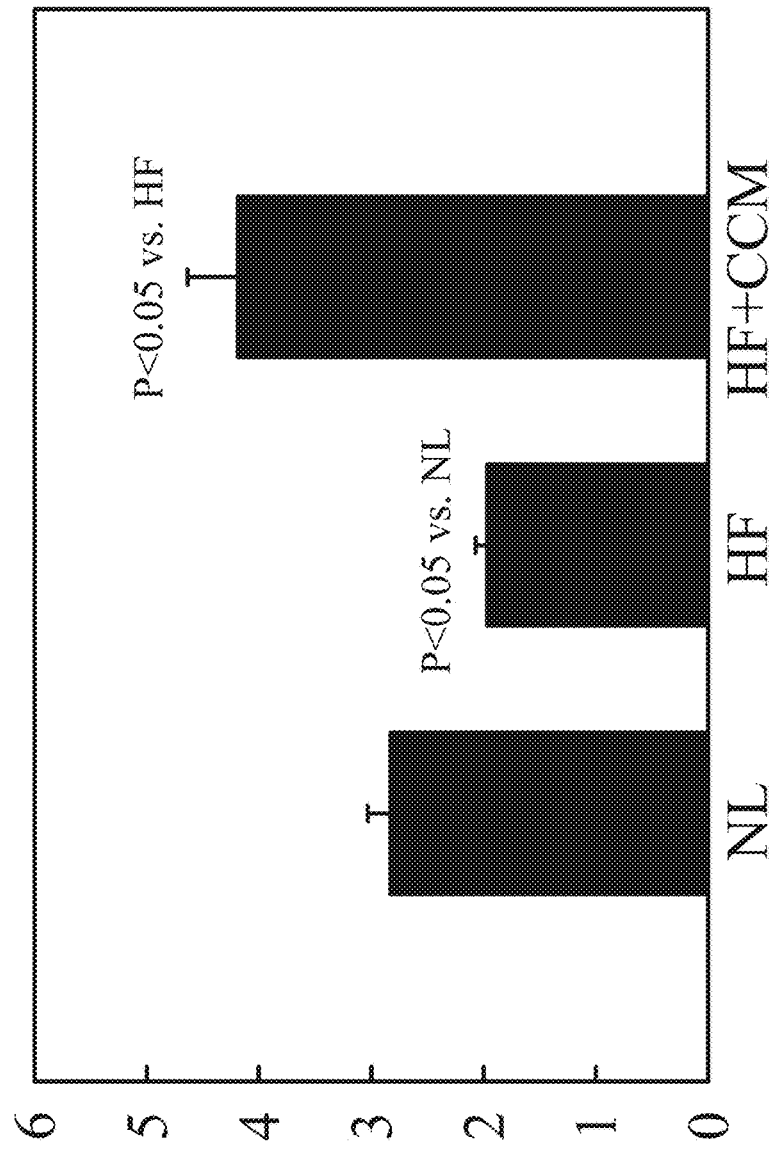

FIG. 2H shows phosphorylated phospholamban normalized to total phospholamban following therapy of several hours (indicated herein as "short-term"). FIG. 2I shows corresponding blots using a Western Blotting method. It should be noted that both phospholamban levels and phosphorylation levels thereof improve with therapy.

Figure 2J:
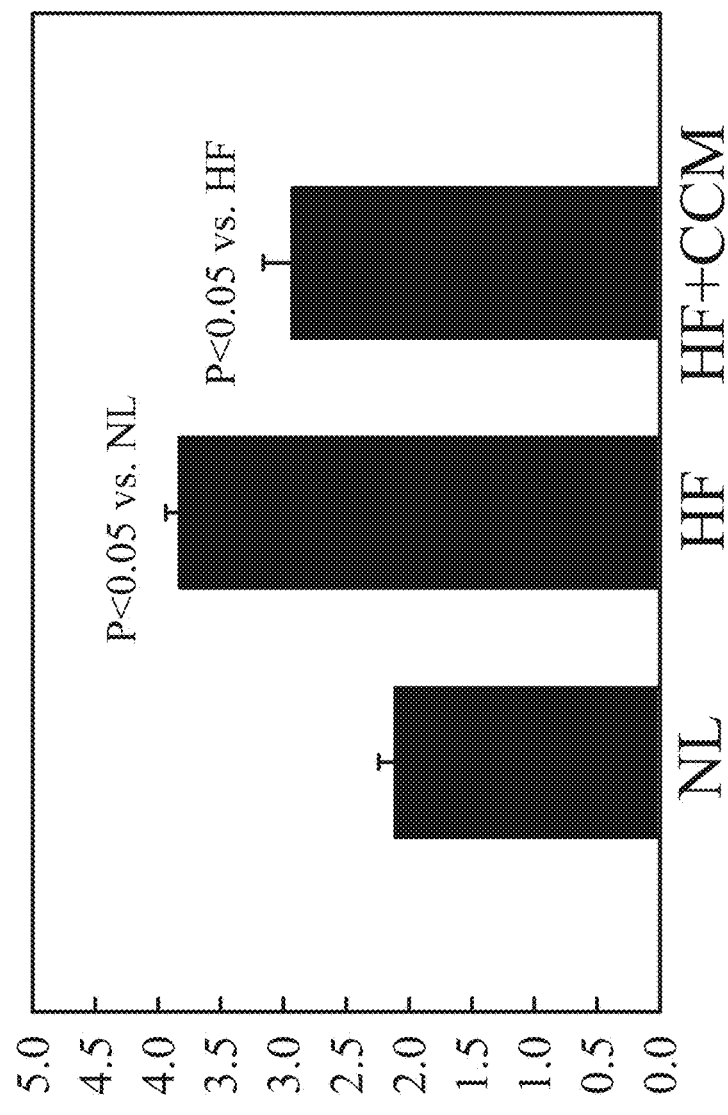
Figure 2K:
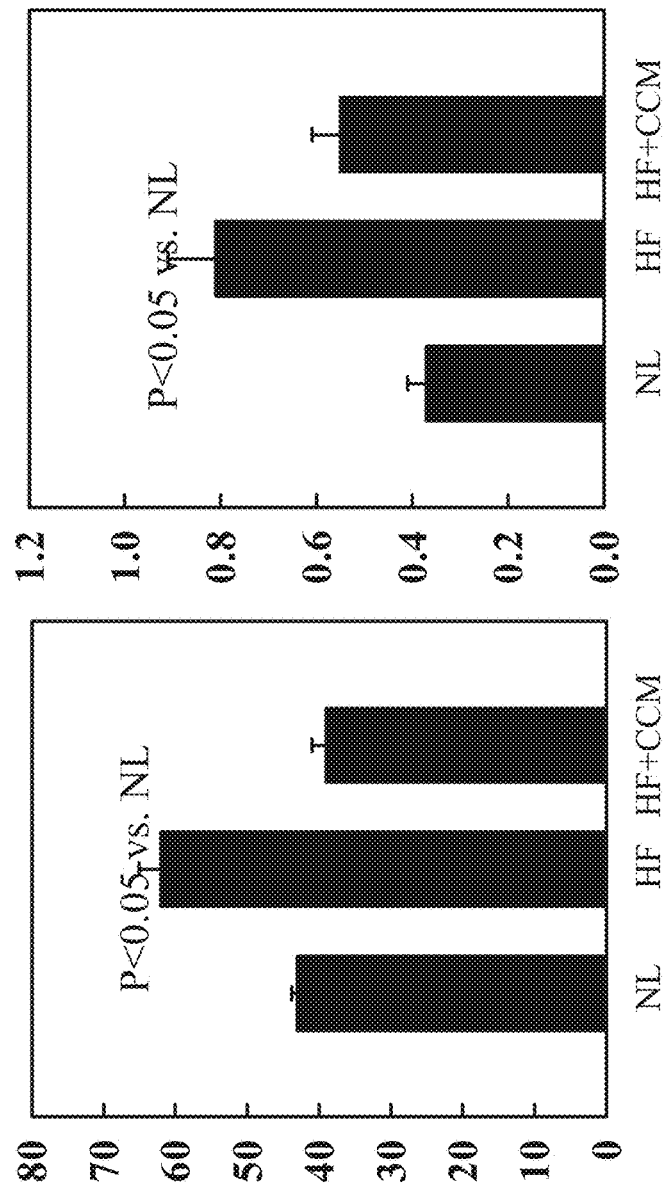

FIG. 2J shows reduction in mRNA expression of NCX following CCM treatment. FIG. 2K shows a general (or slight reduction) normalization of NCX protein values while still maintaining increased relative phosphorylation. This may allow some compensation for disturbed cardiac function.

Figure 2L:
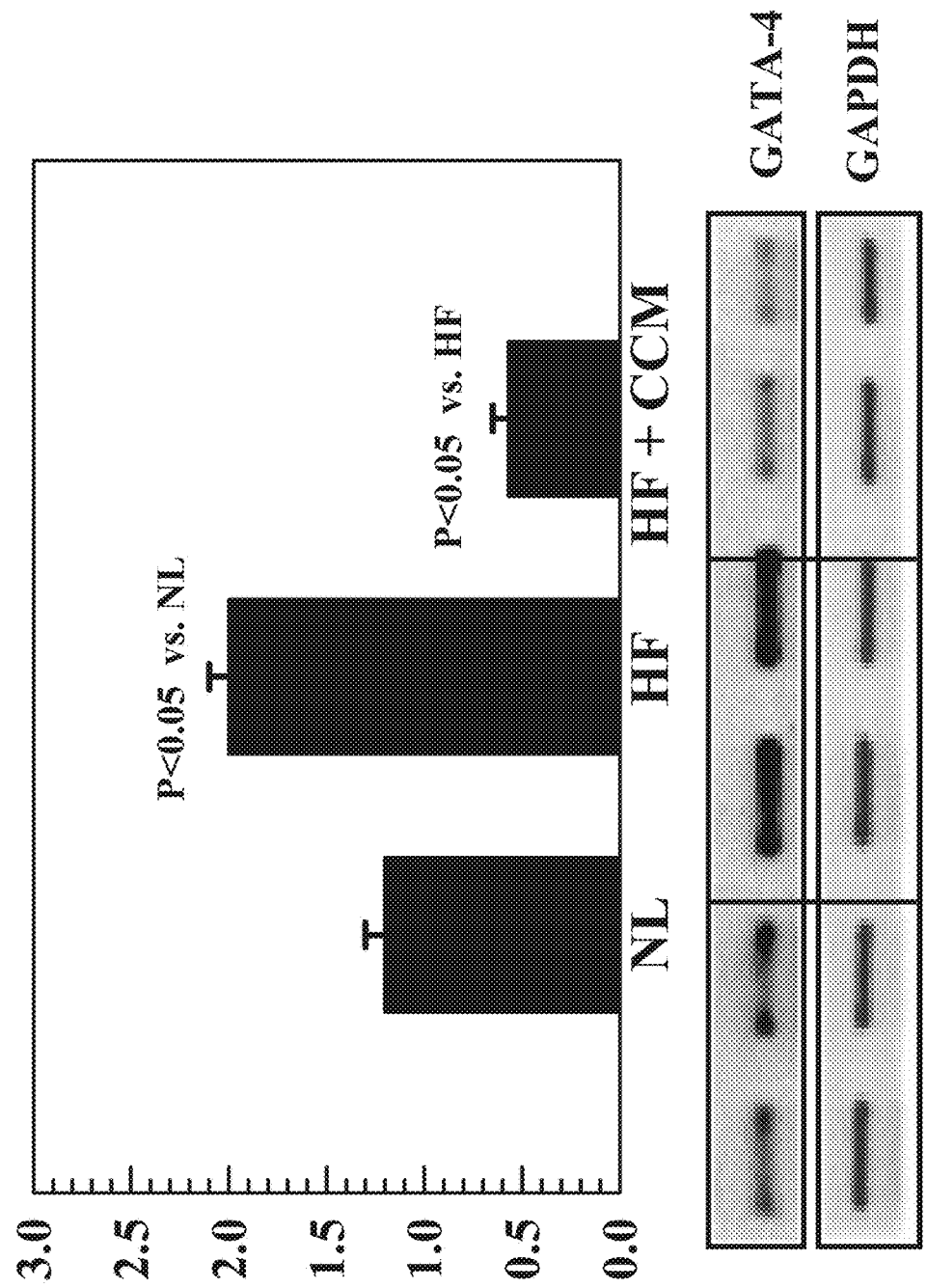
Figure 2M:
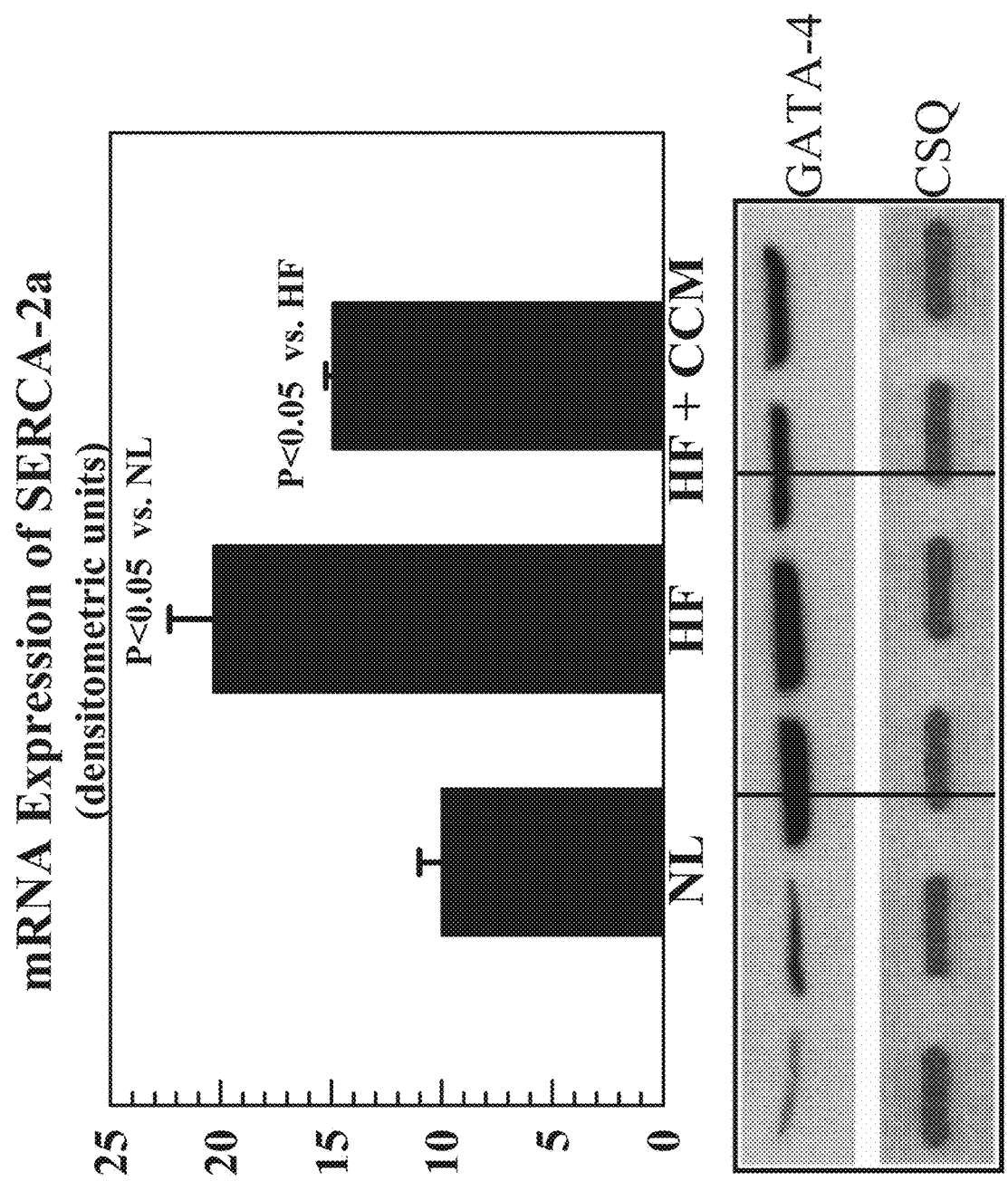
Figure 20:
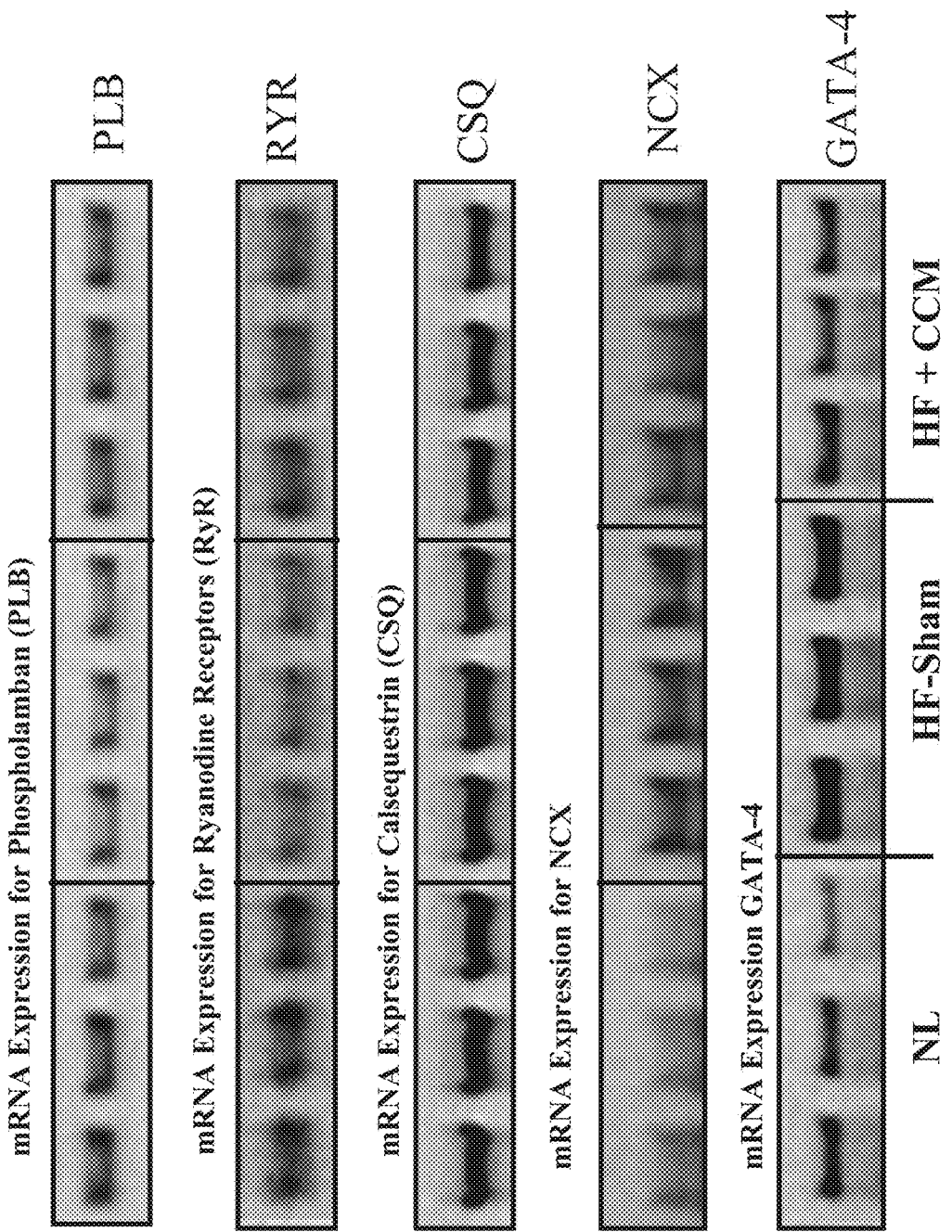

FIG. 2L shows decreased mRNA expression of GATA-4, to even below normal levels. FIG. 2M shows that protein expression of GATA-4, is however, still increased relative to normal. This may be useful for control of NCX and/or other proteins. This result also indicates that merely controlling mRNA may not sufficiently determine the cellular behavior, as protein levels and/or phosphorylation levels may compensate or over compensate. In general, however, the levels are normalized as compared to HF.

FIGS. 2N and 2O show the effect of chronic (e.g., 3 month) treatment with CCM on mRNA expression profiles. Normalization of these important proteins can be seen.

It should be noted that the electric field can operate differently on different proteins, for example, directly affecting some proteins and these proteins indirectly affecting the behavior and/or levels of other proteins. It should also be noted that there are multiple pathways in the cells and the electrical treatment may affect multiple (e.g., 1, 2, 3, 4 or more) pathways in parallel. The resulting effects on proteins may be increasing or decreasing their expression and/or activity levels. Different such effects may be desirable for different proteins and/or different disease conditions. Different proteins may be predisposed (e.g., based on their structure, surrounding materials and/or existing pathways) to differently increase and/or decrease.

The following tables summarize the results on mRNA expression for normal dogs (NL), dogs with HF and dogs with HF and chronic CCM treatment.

TABLE 1

| HF-Control | HF + CCM |
|---|---|
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

Dog Numbers (Units: du)

TABLE 2 mRNA Expression for GAPDH (Units: du)

| | NL | HF-Control | HF + CCM |
|---|---|---|---|
| | 223 | 195 | 246 |
| | 227 | 195 | 223 |
| | 238 | 223 | 232 |
| | 215 | 241 | 250 |
| | 217 | 227 | 229 |
| | 192 | 237 | 237 |
| | | 240 | 232 |
| Mean | 219 | 223 | 236 |
| STD | 15 | 20 | 10 |
| SEM | 6 | 8 | 4 |

ANOVA = 0.16

TABLE 3 mRNA Expression for TNF-alpha (Units: du)

| | NL | HF-Control | HF + CCM |
|---|---|---|---|
| | 48 | 235 | 85 |
| | 53 | 223 | 117 |
| | 36 | 182 | 107 |
| | 28 | 194 | 98 |
| | 39 | 232 | 144 |
| | 31 | 234 | 81 |
| | | 240 | 92 |
| Mean | 39 | 220 | 103 |
| STD | 10 | 23 | 22 |
| SEM | 4 | 9 | 8 |

ANOVA = 0.0001
p vs. NL <0.05 <0.05
p vs. HF-Control <0.05

TABLE 4 mRNA Expression for Activin-A (Units: du)

| | NL | HF-Control | HF + CCM |
|---|---|---|---|
| | 101 | 302 | 174 |
| | 104 | 295 | 142 |
| | 109 | 282 | 150 |
| | 136 | 269 | 148 |
| | 153 | 263 | 100 |
| | 199 | 232 | 92 |
| | | 245 | 88 |
| Mean | 134 | 270 | 128 |
| STD | 38 | 26 | 34 |
| SEM | 15 | 10 | 13 |

ANOVA = 0.0001
p vs. NL <0.05 NS
p vs. HF-Control <0.05

TABLE 5 mRNA Expression for Tubulin-alpha (Units: du)

| | NL | HF-Control | HF + CCM |
|---|---|---|---|
| | 140 | 164 | 82 |
| | 120 | 160 | 124 |
| | 125 | 162 | 144 |
| | 117 | 185 | 146 |
| | 124 | 165 | 160 |
| | 125 | 176 | 141 |
| | | 163 | 168 |
| Mean | 125 | 168 | 138 |
| STD | 8 | 9 | 28 |
| SEM | 3 | 3 | 11 |

ANOVA = 0.002
p vs. NL <0.05 NS
p vs. HF-Control <0.05

TABLE 6 mRNA Expression for ANP (Units: du)

| | NL | HF-Control | HF + CCM |
|---|---|---|---|
| | 21 | 35 | 26 |
| | 19 | 29 | 27 |
| | 17 | 27 | 29 |
| | 12 | 28 | 27 |
| | 18 | 38 | 28 |
| | 23 | 35 | 26 |
| | | 43 | 24 |
| Mean | 18 | 34 | 27 |
| STD | 4 | 6 | 2 |
| SEM | 2 | 2 | 1 |

ANOVA = 0.0001
p vs. NL <0.05 <0.05
p vs. HF-Control <0.05

TABLE 7 mRNA Expression for TIMP-1 (Units: du)

| | NL | HF-Control | HF + CCM |
|---|---|---|---|
| | 160 | 164 | 131 |
| | 185 | 188 | 146 |
| | 184 | 243 | 136 |
| | 203 | 235 | 191 |
| | 248 | 185 | 151 |
| | 270 | 130 | 170 |
| | | 173 | 174 |
| Mean | 208 | 188 | 157 |
| STD | 42 | 40 | 22 |
| SEM | 17 | 15 | 8 |

ANOVA = 0.052

TABLE 8 mRNA Expression for IL-6 (Units: du)

| | NL | HF-Control | HF + CCM |
|---|---|---|---|
| | 277 | 556 | 430 |
| | 302 | 533 | 409 |
| | 349 | 524 | 433 |
| | 337 | 547 | 409 |
| | 350 | 558 | 421 |
| | 348 | 552 | 381 |
| | | 567 | 365 |

TABLE 8-continued mRNA Expression for IL-6 (Units: du)

|  | NL | HF-Control | HF + CCM |
|---|---|---|---|
| Mean | 327 | 548 | 407 |
| STD | 31 | 15 | 25 |
| SEM | 12 | 6 | 10 |

ANOVA = 0.0001
p vs. NL <0.05 <0.05
p vs. HF-Control <0.05

TABLE 9 mRNA Expression for Titin (Units: du)

|  | NL | HF-Control | HF + CCM |
|---|---|---|---|
|  | 183 | 137 | 281 |
|  | 172 | 222 | 278 |
|  | 241 | 182 | 242 |
|  | 285 | 197 | 224 |
|  | 313 | 124 | 257 |
|  | 294 | 135 | 205 |
|  |  | 196 | 231 |
| Mean | 248 | 170 | 245 |
| STD | 60 | 38 | 28 |
| SEM | 24 | 14 | 11 |

ANOVA = 0.005
p vs. NL <0.05 NS
p vs. HF-Control <0.05

TABLE 10 mRNA Expression for Tubulin-beta (Units: du)

|  | NL | HF-Control | HF + CCM |
|---|---|---|---|
|  | 88 | 123 | 75 |
|  | 77 | 127 | 79 |
|  | 68 | 115 | 94 |
|  | 65 | 146 | 91 |
|  | 60 | 133 | 108 |
|  | 62 | 116 | 98 |
|  |  | 133 | 105 |
| Mean | 70 | 128 | 93 |
| STD | 11 | 11 | 12 |
| SEM | 4 | 4 | 5 |

ANOVA = 0.0001
p vs. NL <0.05 <0.05
p vs. HF-Control <0.05

TABLE 11 mRNA Expression for BNP (Units: du)

|  | NL | HF-Control | HF + CCM |
|---|---|---|---|
|  | 32 | 173 | 30 |
|  | 13 | 182 | 47 |
|  | 21 | 166 | 59 |
|  | 31 | 173 | 56 |
|  | 22 | 194 | 35 |
|  | 17 | 186 | 25 |
|  |  | 163 | 58 |
| Mean | 23 | 177 | 44 |
| STD | 8 | 11 | 14 |
| SEM | 3 | 4 | 5 |

ANOVA = 0.0001
p vs. NL <0.05 <0.05
p vs. HF-Control <0.05

TABLE 12 mRNA Expression for TIMP-2 (Units: du)

|  | NL | HF-Control | HF + CCM |
|---|---|---|---|
|  | 233 | 252 | 222 |
|  | 200 | 247 | 239 |
|  | 223 | 238 | 235 |
|  | 230 | 239 | 229 |
|  | 210 | 229 | 225 |
|  | 246 | 240 | 219 |
|  |  | 224 | 198 |
| Mean | 224 | 238 | 224 |
| STD | 17 | 10 | 13 |
| SEM | 7 | 4 | 5 |

ANOVA = 0.12

TABLE 13 mRNA Expression for MMP-1 (Units: du)

|  | NL | HF-Control | HF + CCM |
|---|---|---|---|
|  | 24 | 40 | 29 |
|  | 20 | 38 | 26 |
|  | 18 | 32 | 30 |
|  | 24 | 31 | 24 |
|  | 23 | 41 | 25 |
|  | 33 | 54 | 34 |
|  |  | 32 | 37 |
| Mean | 24 | 38 | 29 |
| STD | 5 | 8 | 5 |
| SEM | 2 | 3 | 2 |

ANOVA = 0.003
p vs. NL <0.05 NS
p vs. HF-Control <0.05

TABLE 14 mRNA Expression for MMP-9 (Units: du)

|  | NL | HF-Control | HF + CCM |
|---|---|---|---|
|  | 35 | 60 | 45 |
|  | 25 | 69 | 49 |
|  | 29 | 43 | 49 |
|  | 26 | 71 | 29 |
|  | 31 | 44 | 42 |
|  | 27 | 41 | 64 |
|  |  | 39 | 42 |
| Mean | 29 | 52 | 46 |
| STD | 4 | 14 | 11 |
| SEM | 2 | 5 | 4 |

ANOVA = 0.003
p vs. NL <0.05 <0.05
p vs. HF-Control NS

TABLE 15 mRNA Expression for p38 MAPK (Units: du)

|  | NL | HF-Control | HF + CCM |
|---|---|---|---|
|  | 48 | 41 | 40 |
|  | 52 | 60 | 44 |
|  | 25 | 46 | 28 |
|  | 41 | 57 | 29 |
|  | 27 | 59 | 33 |
|  | 25 | 67 | 20 |
|  |  | 56 | 20 |

TABLE 15-continued mRNA Expression for p38 MAPK (Units: du)

|  | NL | HF-Control | HF + CCM |
|---|---|---|---|
| Mean | 36 | 55 | 31 |
| STD | 12 | 9 | 9 |
| SEM | 5 | 3 | 3 |

ANOVA = 0.0001
p vs. NL <0.05 NS
p vs. HF-Control <0.05

TABLE 16 mRNA Expression for NCX (Units: du)

|  | NL | HF-Control | HF + CCM |
|---|---|---|---|
|  | 25 | 85 | 31 |
|  | 30 | 115 | 41 |
|  | 36 | 63 | 55 |
|  | 32 | 139 | 50 |
|  | 28 | 39 | 46 |
|  | 29 | 121 | 53 |
|  |  | 126 | 62 |
| Mean | 30 | 98 | 48 |
| STD | 4 | 37 | 10 |
| SEM | 2 | 14 | 4 |

ANOVA = 0.0001
p vs. NL <0.05 NS
p vs. HF-Control <0.05

TABLE 17 mRNA Expression for Beta1-receptor (Units: du)

|  | NL | HF-Control | HF + CCM |
|---|---|---|---|
|  | 22 | 11 | 18 |
|  | 21 | 10 | 17 |
|  | 20 | 6 | 17 |
|  | 19 | 8 | 18 |
|  | 24 | 12 | 19 |
|  | 25 | 11 | 22 |
|  |  | 13 | 17 |
| Mean | 22 | 10 | 18 |
| STD | 2 | 2 | 2 |
| SEM | 1 | 1 | 1 |

ANOVA = 0.0001
p vs. NL <0.05 <0.05
p vs. HF-Control <0.05

TABLE 18 mRNA Expression for MMP-2 (Units: du)

|  | NL | HF-Control | HF + CCM |
|---|---|---|---|
|  | 25 | 56 | 42 |
|  | 22 | 42 | 29 |
|  | 24 | 40 | 30 |
|  | 22 | 39 | 28 |
|  | 23 | 41 | 30 |
|  | 24 | 48 | 27 |
|  |  | 41 | 33 |
| Mean | 23 | 44 | 31 |
| STD | 1 | 6 | 5 |
| SEM | 0 | 2 | 2 |

ANOVA = 0.0001
p vs. NL <0.05 <0.05
p vs. HF-Control <0.05

TABLE 19 mRNA Expression for p21RAS (Units: du)

|  | NL | HF-Control | HF + CCM |
|---|---|---|---|
|  | 85 | 284 | 297 |
|  | 88 | 295 | 270 |
|  | 162 | 305 | 259 |
|  | 167 | 277 | 248 |
|  | 202 | 299 | 228 |
|  | 213 | 295 | 202 |
|  |  | 284 | 201 |
| Mean | 153 | 291 | 244 |
| STD | 55 | 10 | 36 |
| SEM | 22 | 4 | 13 |

ANOVA = 0.0001
p vs. NL <0.05 <0.05
p vs. HF-Control <0.05

TABLE 20 mRNA Expression for Integrin-a5 (Units: du)

|  | NL | HF-Control | HF + CCM |
|---|---|---|---|
|  | 7 | 17 | 7 |
|  | 10 | 14 | 9 |
|  | 4 | 14 | 10 |
|  | 11 | 15 | 7 |
|  | 8 | 25 | 6 |
|  | 7 | 20 | 10 |
|  |  | 12 | 16 |
| Mean | 8 | 17 | 9 |
| STD | 2 | 4 | 3 |
| SEM | 1 | 2 | 1 |

ANOVA = 0.0001
p vs. NL <0.05 NS
p vs. HF-Control <0.05

TABLE 21 mRNA Expression for GATA-4 (Units: du)

|  | NL | HF-Control | HF + CCM |
|---|---|---|---|
|  | 83 | 153 | 84 |
|  | 142 | 247 | 103 |
|  | 136 | 138 | 242 |
|  | 105 | 240 | 191 |
|  | 78 | 164 | 113 |
|  | 71 | 254 | 254 |
|  |  | 233 | 135 |
| Mean | 103 | 204 | 160 |
| STD | 31 | 50 | 69 |
| SEM | 12 | 19 | 26 |

ANOVA = 0.012
p vs. NL <0.05 <0.05
p vs. HF-Control <0.05

TABLE 22 mRNA Expression for SERCA-2a (Units: du)

|  | NL | HF-Control | HF + CCM |
|---|---|---|---|
|  | 218 | 167 | 172 |
|  | 235 | 189 | 200 |
|  | 242 | 159 | 194 |
|  | 238 | 178 | 192 |
|  | 250 | 178 | 195 |
|  | 232 | 179 | 198 |
|  |  | 171 | 193 |

TABLE 22-continued mRNA Expression for SERCA-2a (Units: du)

|      | NL  | HF-Control | HF + CCM |
|------|-----|------------|----------|
| Mean | 236 | 174        | 192      |
| STD  | 11  | 10         | 9        |
| SEM  | 4   | 4          | 3        |

ANOVA = 0.0001
p vs. NL <0.05 <0.05
p vs. HF-Control <0.05

TABLE 23 mRNA Expression for PLB (Units: du)

|      | NL  | HF-Control | HF + CCM |
|------|-----|------------|----------|
|      | 221 | 170        | 217      |
|      | 229 | 149        | 224      |
|      | 255 | 155        | 237      |
|      | 241 | 146        | 222      |
|      | 248 | 167        | 210      |
|      | 200 | 149        | 190      |
|      |     | 109        | 182      |
| Mean | 232 | 149        | 212      |
| STD  | 20  | 20         | 19       |
| SEM  | 8   | 8          | 7        |

ANOVA = 0.0001
p vs. NL <0.05 NS
p vs. HF-Control <0.05

TABLE 24 mRNA Expression for CSQ (Units: du)

|      | NL  | HF-Control | HF + CCM |
|------|-----|------------|----------|
|      | 261 | 274        | 192      |
|      | 258 | 271        | 225      |
|      | 247 | 281        | 262      |
|      | 280 | 291        | 299      |
|      | 268 | 250        | 276      |
|      | 269 | 276        | 281      |
|      |     | 279        | 281      |
| Mean | 264 | 275        | 259      |
| STD  | 11  | 13         | 38       |
| SEM  | 5   | 5          | 14       |

ANOVA = 0.47
p vs. NL NS NS
p vs. HF-Control NS

TABLE 25 mRNA Expression for RYR (Units: du)

|      | NL | HF-Control | HF + CCM |
|------|----|------------|----------|
|      | 40 | 25         | 39       |
|      | 36 | 23         | 30       |
|      | 31 | 29         | 15       |
|      | 42 | 18         | 33       |
|      | 34 | 21         | 34       |
|      | 42 | 22         | 58       |
|      |    | 17         | 43       |
| Mean | 38 | 22         | 36       |
| STD  | 5  | 4          | 13       |
| SEM  | 2  | 2          | 5        |

ANOVA = 0.008
p vs. NL <0.05 NS
p vs. HF-Control <0.05

TABLE 26 mRNA Expression for α-MHC (Units: du)

|      | NL  | HF-Control | HF + CCM |
|------|-----|------------|----------|
|      | 176 | 133        | 192      |
|      | 212 | 136        | 165      |
|      | 219 | 115        | 158      |
|      | 218 | 140        | 181      |
|      | 221 | 179        | 176      |
|      | 224 | 192        | 194      |
|      |     | 144        | 192      |
| Mean | 212 | 148        | 180      |
| STD  | 18  | 27         | 14       |
| SEM  | 7   | 10         | 5        |

ANOVA = 0.0001
p vs. NL <0.05 <0.05
p vs. HF-Control <0.05

Short Discussion of Some Results

Phospholamban is down regulated in heart failure and is nearly normalized with CCM therapy. This may explain the improvement in LV function by CCM treatment. CCM appears to normalize the RYR message which is consistent with proper therapy. The up-regulation of alpha-MHC with CCM may be contributing to the sustained long-term improvement in LV ejection fraction. Decrease in MMP1 following CCM therapy is in and of itself desirable. Inhibiting gelatinases, as shown, is beneficial, possibly reducing interstitial fibrosis and leading to improved LV diastolic compliance and, hence, improved diastolic filling and function. p21RAS and p38 mitogen activated protein kinase (MAPK) are emissions of stretch response genes which are down-regulated following CCM therapy and correlate with reduced cardiomyocytes hypertrophy. Integrin-a5 is clearly normalized following long-term CCM therapy. Up-regulation of Beta1-Adrenergic Receptor is viewed as a positive development which enhances the sensitivity of the contractile element of catecholamines.

Possibly, some therapies according to the present invention will focus on general improvement of health, while other therapies will focus on increasing tissue responsiveness, for example, to certain drugs, and thus focus on improving fewer than all mRNA and/or protein and/or phosphorylation indicators.

Experimental Results—Immediate

The inventors of the present application have discovered that, surprisingly, phosphorylation effects for at least some proteins can be generated in immediate time frames, such as less than 1 minute and even less than 10 or 5 seconds in some cases. Further, an immediacy of effect is also characterized by a reduced number of intermediate stages, indicated by the fact that protein phosphorylation effects can be imposed even in tissue homogenate. Further, specificity of the phosphorylation effects to certain proteins that are relevant for HF is also shown. Further, a lack of effect of an exemplary pacing signal is also shown.

Tissue Homogenate

Figure 3A:
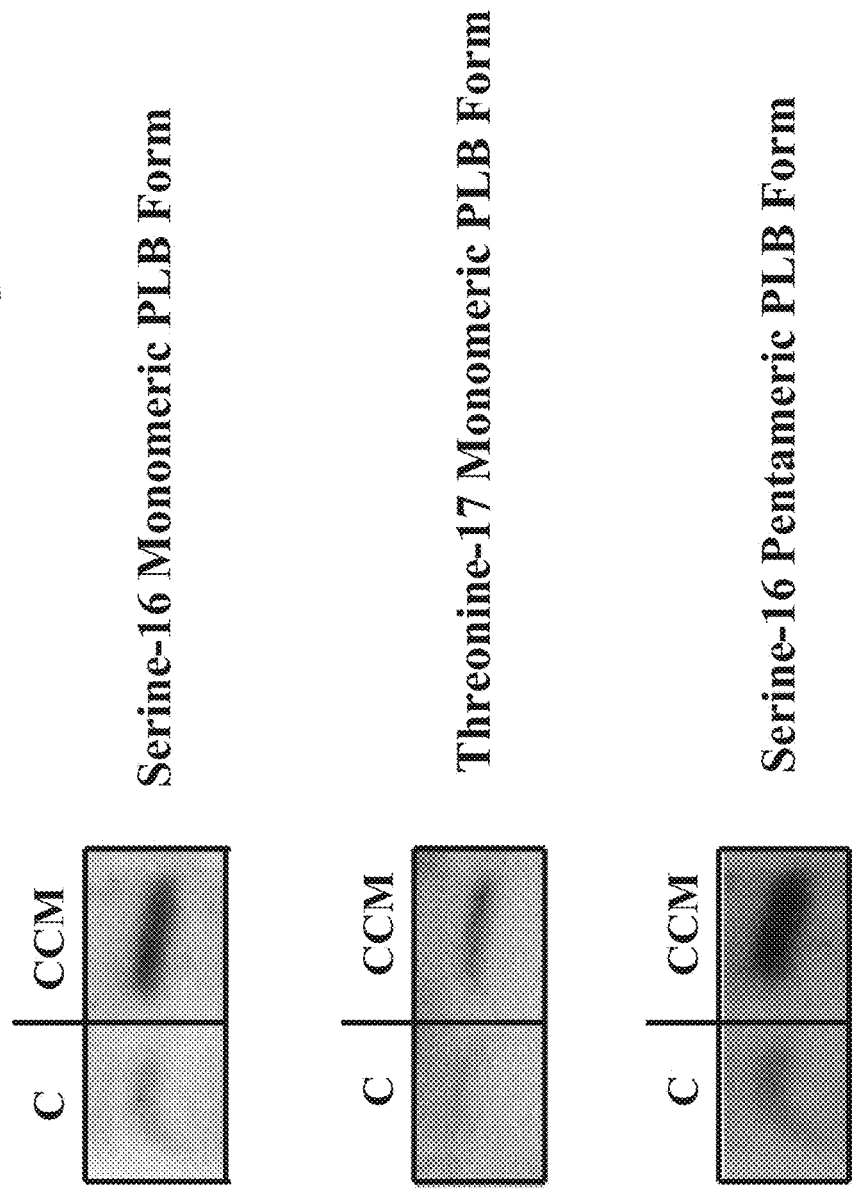
Figure 3B:
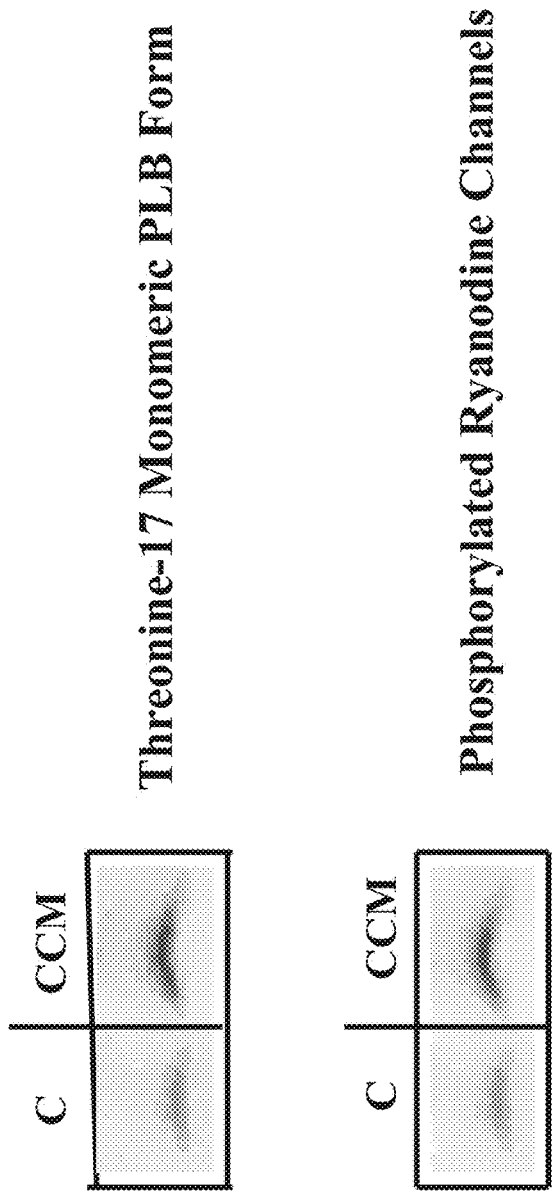

FIGS. 3A and 3B show the effect of a CMM signal applied to tissue homogenate from LV failed heart tissue. As can be seen, even a 10 second signal was sufficient to generate noticeable and significant changes in phosphorylation. Changes in phosphorylation are shown in Serine-16 Monometric PLB (Phospholamban) form, Threonin-17 mometric PLB form, Serine 16 Pentametric PLB form and Ryanodine channels.

The tissue homogenate was prepared in the following manner. Approximately 14 g frozen LV tissue from a dog with chronic HF in 42 ml 50 mM Tris-HCl, pH 7.5 was homogenized three times for 20 seconds each time using a 10-mm generator (Omni International, Waterbury, Conn.) at setting 10. The homogenate was then filtered through 4 layers of cheese cloth. The resulting homogenate was stored in ice and its protein concentration was determined by the Lowry method.

The CCM signals were delivered to the homogenate as follows. The homogenate was diluted 2 fold in homogenate buffer and subsequently aliquotted 3 ml each in assay tubes. Assay tubes were divided into 2 sets (Set A and Set B), each subset consisting of 7 assay tubes. CCM signals were delivered for 10", 30", 1', 5', 30', and 60' in one of the sets, while the other set served as time control. The reaction was stopped by adding concentrated SDS. Protein assay on all the samples were performed by Lowry method.

Phosphorylation of PLB at serine-16 (Ser-16) and threonine-17 (Thr-17) was determined by Western blotting using specific antibody as described in Mishra S, Sabbah HN, Jain J C, Gupta R C: "Reduced Ca2+-calmodulin-dependent protein kinase activity and expression in LV myocardium of dogs with heart failure", Am J Physiol Heart Circ Physiol 284:H876-H883, 2003, the disclosure of which is incorporated herein by reference. Briefly, approximately 100 microgram protein for Se-16 and 40 microgram for Thr-17 were elecrophoresed on 18% SDS-gel, protein was transferred from the gel to nitrocellulose membrane, the blot was probed with primary and secondary antibodies and finally bands were visualized by an ECL method.

It should be noted that tissue homogenate was generally activated at room temperature, below the normal operating temperature of a heart. This and other features of the results suggest a direct chemical or electrical effect on the proteins which is possibly divorced or semi divorced from cell function and/or complex biochemical mechanisms (e.g., more than two or three steps or with feedback). Such divorcing may help in the application of the effect under various conditions including various polarization conditions and tissue health states.

Failed Cardiomyocytes, pacing and CCM

Figure 3C:
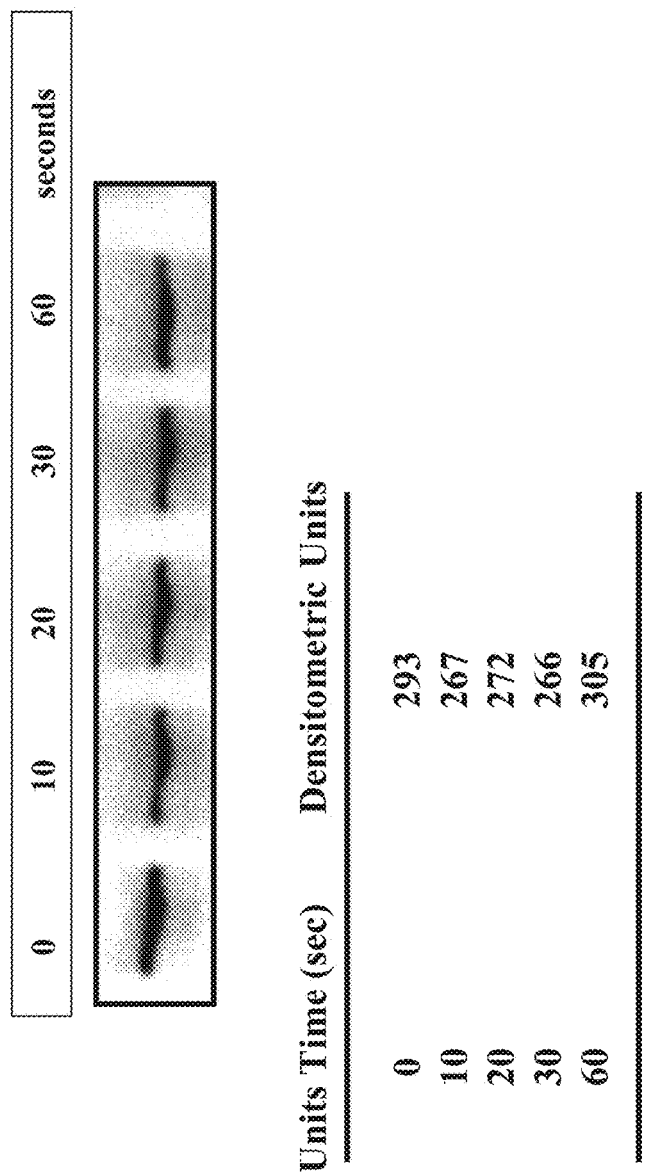

FIG. 3C shows phosphorylation of a Ryanodine receptor in isolated (in-vitro) failed cardiomyocytes, after application of CCM for 10, 20, 30 and 60 seconds. Lack of significant immediate effect is consistent with the lack of long-term effect shown above and serves to show that the effect of the CCM signal can be made specific to certain proteins.

Figure 3D:
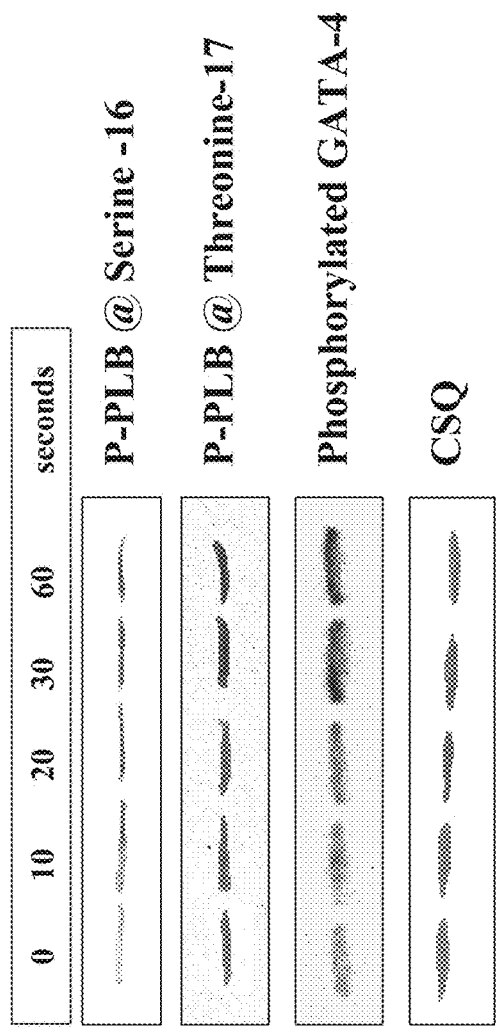

FIG. 3D shows phosphorylation of PLB and GATA, as compared to that of CSQ, in failed isolated myocytes. As can be seen a phosphorylation effect is shown for some of the proteins, which matches the general results for tissue homogenate. Also noteworthy is that the effect increases over time at different rates for different proteins. Relaxation times of phosphorylation levels for different proteins are also generally different. The change in GATA-4 is important because when GATA-4 is phosphorylated, this process decreases the activity of the sodium calcium exchanger and helps contractility improve quickly.

FIG. 3E shows that a pacing signal applied at 3V for pulses of 0.75 msec did not have any significant immediate effect on any of the proteins. Possibly, this is caused by the reduced current density of the pacing pulse and/or due to the substantially lower charge transport rate. Possibly, any minimal effect of the pacing signal is relaxed in the times between signals. Optionally, the pacing signal is not strong enough to pass a certain minimal threshold of effect.

In Vivo Heart

The following tables summarize the results from 2 heart failure dogs in which phosphorylation of phospholamban (PLB-P) after application of CCM signals was studied, while taking biopsies at 1, 5, 10, and 15 minutes. Normalization to CSQ was used to correct for any effect of blood in the biopsies. The increase in PLB-P matches a measured increase in dP/dt measured in these experiments. It is noted that PLB-P levels remained elevated for 15 minutes after application of CCM, suggesting a temporally sparse field application treatment. Optionally, such a prolonged elevation has a long term effect on mRNA expression. Various locations on the LV were tried, all with similar results, as shown below.

TABLE 27

Heart failure dogs (Units: du)

| | CCM Time (min) | CSQ (du) | PLB-P @ Ser-16 (du) | PLB-P @ Thr-17 (du) | PLB-P Normalized to CSQ | |
|---|---|---|---|---|---|---|
| | | | | | Ser-16 | Thr-17 |
| First dog First set | 0 | 146.09 | 34.80 | 28.98 | 0.24 | 0.20 |
| | 1 | 145.94 | 60.61 | 34.72 | 0.42 | 0.24 |
| | 5 | 125.88 | 60.67 | 50.51 | 0.48 | 0.40 |
| | 10 | 103.76 | 92.46 | 33.09 | 0.89 | 0.32 |
| First dog Second set | 0 | 108.38 | 21.94 | 25.55 | 0.20 | 0.24 |
| | 1 | 107.27 | 71.44 | 82.46 | 0.67 | 0.77 |
| | 5 | 112.83 | 63.31 | 61.28 | 0.56 | 0.54 |
| | 10 | 72.57 | 32.85 | 61.98 | 0.45 | 0.85 |
| First dog Third set | 0 | 103.06 | 26.76 | 20.16 | 0.26 | 0.20 |
| | 1 | 116.54 | 65.60 | 96.83 | 0.56 | 0.83 |
| | 5 | 139.30 | 79.67 | 144.88 | 0.57 | 1.04 |
| | 10 | 112.53 | 61.41 | 62.99 | 0.55 | 0.56 |
| | 15 | 121.23 | 55.86 | 68.86 | 0.46 | 0.57 |
| Second Dog First set | 0 | 117.25 | 20.93 | 16.76 | 0.18 | 0.14 |
| | 1 | 119.63 | 36.03 | 33.77 | 0.30 | 0.28 |
| | 5 | 132.55 | 39.08 | 38.74 | 0.29 | 0.29 |
| | 10 | 80.44 | 22.24 | 16.80 | 0.28 | 0.21 |
| Second Dog Second set | 0 | 111.84 | 33.72 | 40.98 | 0.30 | 0.37 |
| | 1 | 118.21 | 62.71 | 71.28 | 0.53 | 0.60 |
| | 5 | 68.39 | 31.31 | 32.52 | 0.46 | 0.48 |
| | 10 | 38.79 | 26.91 | 29.31 | 0.69 | 0.76 |
| Second Dog Third set | 0 | 114.50 | 24.17 | 28.37 | 0.21 | 0.25 |
| | 1 | 121.82 | 44.52 | 62.01 | 0.37 | 0.51 |
| | 5 | 122.01 | 46.91 | 68.04 | 0.38 | 0.56 |
| | 10 | 134.98 | 69.64 | 94.13 | 0.52 | 0.70 |
| | 15 | 86.65 | 35.72 | 31.55 | 0.41 | 0.36 |

TABLE 28

Average of all 6 sets obtained from 2 dogs (Units: du)

| CCM Time (min) | PLB-P Normalized to CSQ | |
|---|---|---|
| | Ser-16 | Thr-17 |
| 0 | 0.23 | 0.23 |
| 1 | 0.47 | 0.54 |
| 5 | 0.46 | 0.55 |
| 10 | 0.56 | 0.57 |
| 15 | 0.44 | 0.47 |

Two sets only (3rd set from each dog)

Without being limited to any particular hypothesis, it is hypothesized by the inventors that the applied electric field either has a direct effect on the proteins or has an effect on a cofactor or protein that enhance phosphorylation of proteins. The above "Voltage-dependent potentiation . . . " paper suggests that an electric field can directly modify the natural phosphorylation rate of a protein.

Human Results mRNA expression we measured for some genes in human subjects. Therapy with non-excitatory cardiac contractility modulation (CCM) electrical signals was delivered to LV muscle during the absolute refractory period improves LV function in patients with HF. The effects of 3 months CCM therapy on mRNA expression of cardiac fetal and SR genes in 5 patients with advanced HF were examined. In the experiment, right sided endomyocardial biopsies were obtained at baseline, prior to activating CCM therapy, and at 3 and 6 months thereafter. CCM therapy was delivered in random order of ON for 3 months and OFF for 3 months. mRNA expression was performed in a blinded fashion as to the ON/OFF order of therapy. Expression of the fetal genes A-type (ANP) and B-type (BNP) natriuretic peptides and α-myosin heavy chain (MHC), and the SR genes SERCA-2a, phospholamban (PLB) and ryanodine receptors (RYR) was measured using RT-PCR and bands quantified in densitometric units (du). The percent change in du between baseline and the ON and OFF 3 months phases was calculated.

The 3 months therapy OFF phase was associated with increased expression of ANP and BNP and decreased expression of α-MHC, SERCA-2a, PLB and RYR (Table). In contrast, the 3 months ON therapy phase resulted in decreased expression of ANP and BNP and increased expression of α-MHC, SERCA-2a, PLB and RYR (Table). This suggests that in patients with HF, CCM therapy reverses the cardiac maladaptive fetal gene program and normalizes expression of key SR Ca2+ cycling genes. These observations are consistent with the observed improvement in LV function in patients with HF following long-term CCM therapy.

TABLE 29 mRNA Expression (% Change from Baseline) (Units: du)

|  | OFF Phase | ON Phase | P-Value |
|---|---|---|---|
| ANP | 82 ± 26 | −57 ± 9 | 0.009 |
| BNP | 81 ± 28 | −55 ± 9 | 0.007 |
| α-MHC | −29 ± 9 | 80 ± 16 | 0.004 |
| SERCA-2a | −21 ± 10 | 45 ± 14 | 0.039 |
| PLB | 4 ± 18 | 93 ± 45 | 0.084 |
| RYR | −20 ± 6 | 34 ± 6 | 0.002 |

Protein Results

Figure 5A:
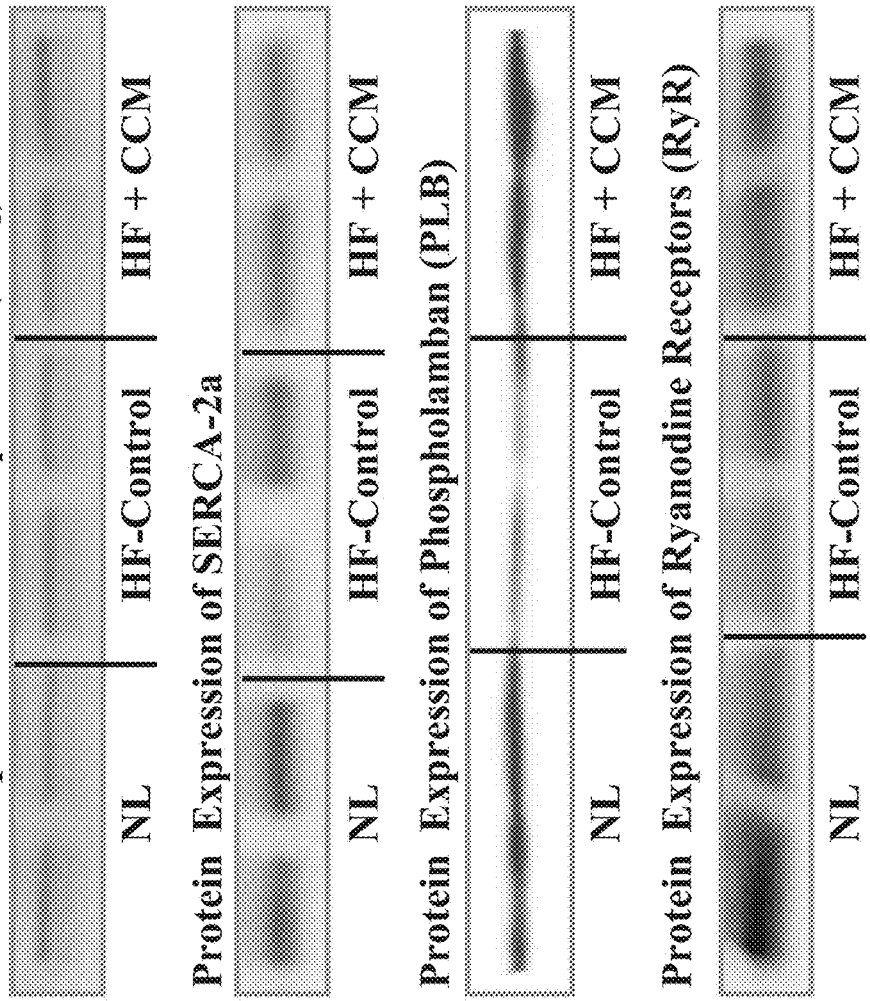
FIGS. 5A-5R are blots showing relative protein levels (in dogs) for control, heart failure and heart failure with chronic CCM application, in accordance with an exemplary embodiment of the invention.

FIGS. 5A-5R shows protein expression results for the following proteins in chronic dogs, in control, heart failure and treated heart failure conditions: CSQ, SERCA-2a, PLB, RyR, NCX, IL-6, GATA-4, GAPDH, MMP-9, Tubulin-Beta, GATA-1, MMP-1, Tubulin-Alpha, Titin, TIMP-1, Integrin-α5, TNF α, p21ras, p38 MAPK, TIMP-2, $\beta_1$-AR, MMP-2, ANP and BNP.

It should be noted that some blots are shown twice, in order to facilitate comparison between them.

Following is a tabular analysis of these results with a short discussion.

FIGS. 5A-5D show results for the following SR proteins: Calsequestrin, phospholamban, SERCA-2a (Calcium ATPase) and ryanodine receptors; the following Pump Proteins: Sodium-Calcium Exchanger; the following Transcription Factors: GATA-4; and the following Cytokines: Interleukin-6.

In general, these seven proteins moved directionally the same as their mRNA expression. Phospholamban showed complete normalization as did SERCA-2a.

These results are consistent with the concept that the CCM acute and chronic effect is mediated by favorable modification of calcium cycling within the sarcoplasmic reticulum.

Also notable is that under chronic condition, the CCM signals appear to normalize the over-expression of the sodium-calcium exchanger.

Re FIG. 5A:

TABLE 30

Dog Numbers - same for all FIGS. 5A-5R (Units: du)

| HF-Control | HF + CCM |
|---|---|
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

TABLE 31

Protein Expression of CSQ (Units: du)

|  | NL | HF-Control | HF + CCM |
|---|---|---|---|
|  | 49 | 41 | 33 |
|  | 41 | 44 | 40 |
|  | 38 | 33 | 48 |
|  | 45 | 42 | 38 |
|  | 50 | 41 | 40 |
|  | 34 | 37 | 47 |
|  |  | 44 | 61 |
| Mean | 43 | 40 | 44 |
| STD | 6 | 4 | 9 |
| SEM | 3 | 1 | 3 |

ANOVA = 0.49
p vs. NL
p vs. HF-Control

TABLE 32

Protein Expression of Phospholamban (Units: du)

|  | NL | HF-Control | HF + CCM |
|---|---|---|---|
|  | 64 | 30 | 75 |
|  | 63 | 23 | 60 |
|  | 74 | 27 | 97 |
|  | 63 | 29 | 65 |
|  | 75 | 18 | 80 |
|  | 52 | 30 | 76 |
|  |  | 29 | 69 |
| Mean | 65 | 27 | 75 |
| STD | 8 | 5 | 12 |
| SEM | 3 | 2 | 5 |

ANOVA = 0.0001
p vs. NL <0.05 NS
p vs. HF-Control <0.05

TABLE 33

Protein Expression of SERCA-2a (Units: du)

| NL | HF-Control | HF + CCM |
|---|---|---|
| 77 | 37 | 94 |
| 77 | 69 | 67 |
| 89 | 54 | 68 |
| 117 | 58 | 57 |
| 95 | 39 | 59 |
| 74 | 57 | 111 |
|  | 63 | 53 |

TABLE 33-continued

Protein Expression of SERCA-2a (Units: du)

| NL | HF-Control | HF + CCM |
|----|------------|----------|
| 88 | 54 | 73 |
| 16 | 12 | 21 |
| 7 | 4 | 8 |

ANOVA = 0.007  
p vs. NL <0.05 NS  
p vs. HF-Control <0.05

TABLE 34

Protein Expression of RyR (Units: du)

| NL | HF-Control | HF + CCM |
|----|------------|----------|
| 129 | 75 | 115 |
| 123 | 98 | 107 |
| 153 | 102 | 119 |
| 104 | 86 | 86 |
| 140 | 100 | 78 |
| 104 | 86 | 91 |
|  | 72 | 147 |
| 126 | 88 | 106 |
| 20 | 12 | 23 |
| 8 | 5 | 9 |

ANOVA = 0.009  
p vs. NL <0.05 NS  
p vs. HF-Control NS

Figure 5B:
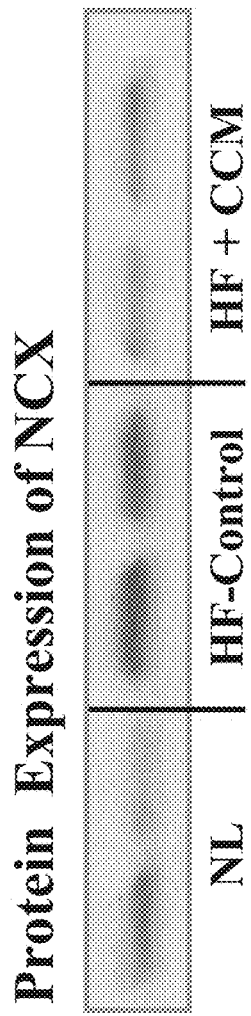

Re FIG. 5B:

TABLE 35

Protein Expression of NCX (Units: du)

| NL | HF-Control | HF + CCM |
|----|------------|----------|
| 26 | 62 | 30 |
| 43 | 50 | 39 |
| 29 | 38 | 35 |
| 36 | 45 | 29 |
| 41 | 49 | 50 |
| 44 | 76 | 25 |
|  | 58 | 51 |
| 37 | 54 | 37 |
| 8 | 12 | 10 |
| 3 | 5 | 4 |

ANOVA = 0.013  
p vs. NL <0.05 NS  
p vs. HF-Control <0.05

Figure 5C:
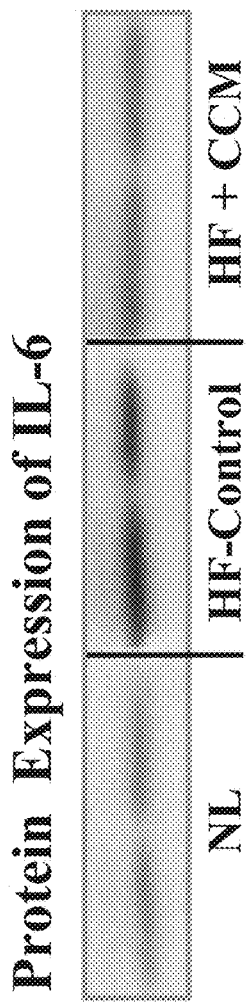

Re FIG. 5C:

TABLE 36

Protein Expression of IL-6 (Units: du)

| NL | HF-Control | HF + CCM |
|----|------------|----------|
| 56 | 74 | 31 |
| 56 | 51 | 70 |
| 43 | 87 | 51 |
| 50 | 84 | 106 |
| 47 | 107 | 65 |
| 86 | 118 | 66 |
|  | 90 | 51 |
| 56 | 87 | 63 |
| 15 | 22 | 23 |
| 6 | 8 | 9 |

ANOVA = 0.033  
p vs. NL <0.05 NS  
p vs. HF-Control <0.05

Figure 5D:
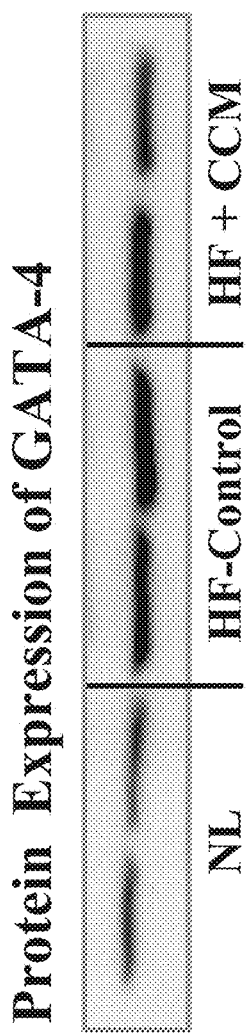

Re FIG. 5D:

TABLE 37

Protein Expression of GATA-4 (Units: du)

| NL | HF-Control | HF + CCM |
|----|------------|----------|
| 90 | 158 | 63 |
| 97 | 179 | 93 |
| 75 | 100 | 129 |
| 105 | 133 | 126 |
| 103 | 157 | 113 |
| 106 | 127 | 103 |
|  | 110 | 141 |
| 96 | 138 | 110 |
| 12 | 28 | 26 |
| 5 | 11 | 10 |

ANOVA = 0.018  
p vs. NL <0.05 NS  
p vs. HF-Control <0.05

FIGS. 5E-5H show results for GAPDH (Housekeeping), transcription factor GATA-1 which did not change, matrix metalloproteinase-9 which changes consistent with mRNA expression and cytoskeletal protein Tubulin-beta which also changes consistent with what is shown for mRNA expression. GATA-1 is shown in comparison with GATA-4.

Figure 5E:
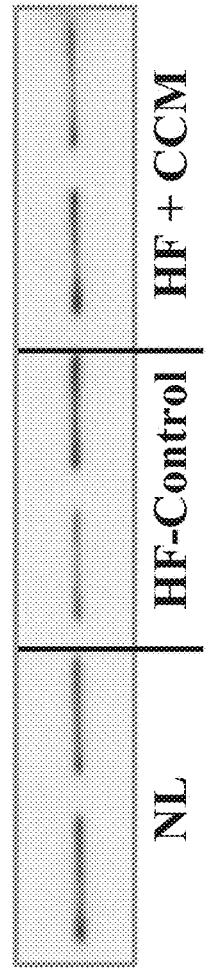

Re FIG. 5E

TABLE 38

Protein Expression of GAPDH (Units: du)

| NL | HF-Control | HF + CCM |
|----|------------|----------|
| 32 | 34 | 34 |
| 36 | 33 | 36 |
| 35 | 37 | 32 |
| 35 | 32 | 28 |
| 34 | 31 | 35 |
| 31 | 27 | 46 |
|  | 27 | 30 |
| 34 | 32 | 34 |
| 2 | 4 | 6 |
| 1 | 1 | 2 |

ANOVA = 0.54  
p vs. NL NS NS  
p vs. HF-Control NS

Figure 5F:
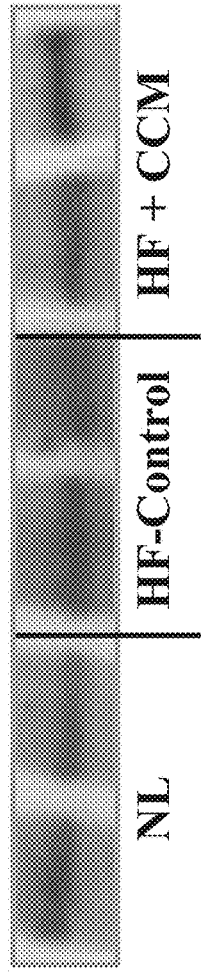

Re FIG. 5F:

TABLE 39

Protein Expression of MMP-9 (Units: du)

| NL | HF-Control | HF + CCM |
|----|------------|----------|
| 394 | 637 | 668 |
| 448 | 779 | 569 |
| 452 | 821 | 611 |
| 455 | 733 | 551 |
| 488 | 687 | 504 |
| 426 | 643 | 572 |
|  | 742 | 486 |
| 444 | 720 | 566 |
| 32 | 69 | 62 |
| 13 | 26 | 23 |

ANOVA = 0.0001  
p vs. NL <0.05 <0.05  
p vs. HF-Control <0.05

Figure 5G:
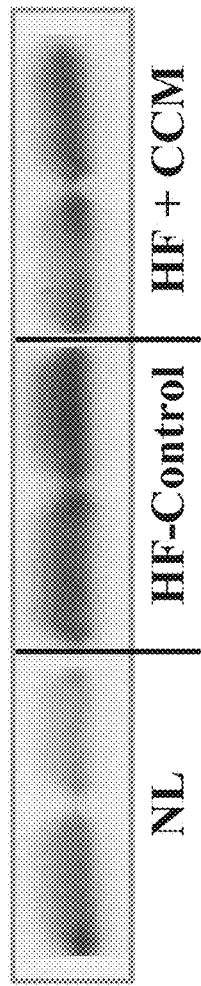

Re FIG. 5G:

TABLE 40

| Tubulin-beta (Units: du) | | |
|---|---|---|
| NL | HF-Control | HF + CCM |
| 512 | 1008 | 656 |
| 644 | 810 | 693 |
| 584 | 973 | 647 |
| 450 | 725 | 543 |
| 390 | 693 | 654 |
| 301 | 778 | 675 |
|  | 1078 | 689 |
| 480 | 866 | 651 |
| 126 | 151 | 51 |
| 52 | 57 | 19 |

ANOVA = 0.0001
p vs. NL <0.05 <0.05
p vs. HF-Control <0.05

Re FIG. 5H

TABLE 41

| Protein Expression of GATA-1 (Units: du) | | |
|---|---|---|
| NL | HF-Control | HF + CCM |
| 83 | 108 | 118 |
| 97 | 110 | 121 |
| 99 | 60 | 130 |
| 115 | 109 | 122 |
| 106 | 106 | 121 |
| 93 | 94 | 75 |
|  | 103 | 101 |
| 99 | 99 | 113 |
| 11 | 18 | 19 |
| 4 | 7 | 7 |

ANOVA = 0.22
p vs. NL NS NS
p vs. HF-Control NS

FIGS. 5I-5L show results from the proteins matrix-metalloproteinase-1 (MMP-1), cytoskeletal proteins tubulin alpha and titin, tissue inhibitor of matrix-metalloproteinase-1 (TIMP-1) and cell surface protein integrin-alpha-5.

There were no apparent changes in TIMP-1. CCM therapy also had no significant effect on integrin-alpha-5. It should be noted that integrin-alpha-5 can be affected by other means, such as mechanically constraining the heart (e.g., thus directly affecting its transduction function).

CCM therapy, however, significantly down-regulated MMP-1, tubulin-alpha and titin which is consistent with the observation with respect to the effects of CCM on mRNA expression of these genes.

Re FIG. 5I

TABLE 42

| Protein Expression of MMP-1 (Units: du) | | |
|---|---|---|
| NL | HF-Control | HF + CCM |
| 521 | 936 | 482 |
| 449 | 894 | 574 |
| 425 | 883 | 511 |
| 484 | 1066 | 538 |
| 437 | 985 | 527 |
| 525 | 997 | 539 |
|  | 971 | 476 |

TABLE 42-continued

| Protein Expression of MMP-1 (Units: du) | | |
|---|---|---|
| NL | HF-Control | HF + CCM |
| 474 | 962 | 521 |
| 43 | 63 | 34 |
| 18 | 24 | 13 |

ANOVA = 0.0001
p vs. NL <0.05 NS
p vs. HF-Control <0.05

Re FIG. 5J

TABLE 43

| Tubulin-alpha (Units: du) | | |
|---|---|---|
| NL | HF-Control | HF + CCM |
| 196 | 298 | 217 |
| 161 | 322 | 233 |
| 129 | 359 | 187 |
| 136 | 283 | 214 |
| 142 | 307 | 239 |
| 158 | 260 | 257 |
|  | 274 | 250 |
| 154 | 300 | 228 |
| 24 | 33 | 24 |
| 10 | 13 | 9 |

ANOVA = 0.0001
p vs. NL <0.05 <0.05
p vs. HF-Control <0.05

TABLE 44

| Protein Expression of Titin (Units: du) | | |
|---|---|---|
| NL | HF-Control | HF + CCM |
| 609 | 232 | 368 |
| 575 | 211 | 285 |
| 528 | 218 | 306 |
| 412 | 302 | 213 |
| 400 | 231 | 248 |
| 467 | 223 | 329 |
|  | 191 | 243 |
| 499 | 230 | 285 |
| 86 | 35 | 54 |
| 35 | 13 | 20 |

ANOVA = 0.0001
p vs. NL <0.05 <0.05
p vs. HF-Control NS

Figure 5K:
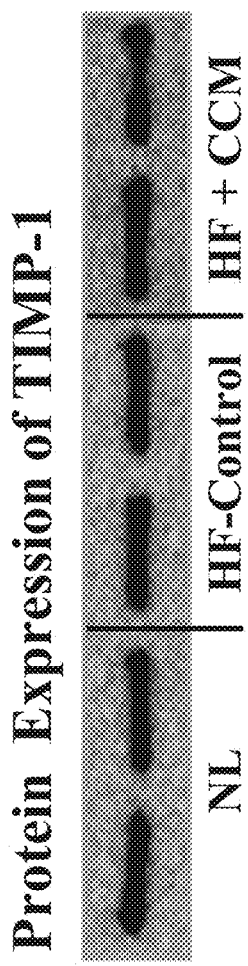

Re FIG. 5K:

TABLE 45

| Protein Expression of TIMP-1 (Units: du) | | |
|---|---|---|
| NL | HF-Control | HF + CCM |
| 609 | 914 | 786 |
| 718 | 835 | 849 |
| 915 | 863 | 811 |
| 694 | 679 | 888 |
| 724 | 773 | 781 |
| 834 | 676 | 762 |
|  | 787 | 709 |
| 749 | 790 | 798 |
| 109 | 90 | 58 |
| 44 | 34 | 22 |

ANOVA = 0.57
p vs. NL NS NS
p vs. HF-Control NS

Figure 5L:
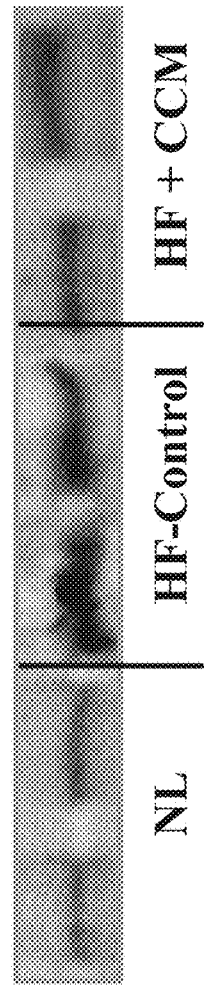

Re FIG. 5L:

TABLE 46

| Integrin-alpha -5 (Units: du) | | |
|---|---|---|
| NL | HF-Control | HF + CCM |
| 228 | 340 | 254 |
| 153 | 455 | 239 |
| 160 | 437 | 212 |
| 223 | 358 | 193 |
| 185 | 332 | 168 |
| 201 | 356 | 253 |
|  | 324 | 249 |
| 192 | 372 | 224 |
| 31 | 52 | 34 |
| 13 | 20 | 13 |

ANOVA = 0.0001
p vs. NL <0.05 NS
p vs. HF-Control <0.05

FIGS. 5M-5P show results from the proteins TNF-α (showed in comparison to IL-6), p21ras, p38 MAPK, TIMP-2 (showed in comparison to TIMP-1 and β1-AR.

The lack of change in TIMP-2 is consistent with previous observations. Long-term CCM therapy significantly reduced protein expression of the cytokine TNF-α and significantly reduced the expression of the stretch proteins p21ras as well as p38 MAPK. This is consistent with the observation that CCM therapy attenuates cardiomyocyte hypertrophy. Also to be noted is up-regulation of the beta-1 adrenergic receptor, which is favorable.

Re FIG. 5M

TABLE 47

| Protein Expression of IL-6 (Units: du) | | |
|---|---|---|
| NL | HF-Control | HF + CCM |
| 56 | 74 | 31 |
| 56 | 51 | 70 |
| 43 | 87 | 51 |
| 50 | 84 | 106 |
| 47 | 107 | 65 |
| 86 | 118 | 66 |
|  | 90 | 51 |
| 56 | 87 | 63 |
| 15 | 22 | 23 |
| 6 | 8 | 9 |

ANOVA = 0.033
p vs. NL <0.05 NS
p vs. HF-Control <0.05

TABLE 48

| Protein Expression of TNFα (Units: du) | | |
|---|---|---|
| NL | HF-Control | HF + CCM |
| 44 | 155 | 63 |
| 44 | 161 | 89 |
| 31 | 149 | 53 |
| 47 | 125 | 87 |
| 51 | 168 | 75 |
| 39 | 180 | 96 |
|  | 176 | 80 |
| 43 | 159 | 78 |
| 7 | 19 | 15 |
| 3 | 7 | 6 |

ANOVA = 0.0001
p vs. NL <0.05 <0.05
p vs. HF-Control <0.05

Figure 5N:
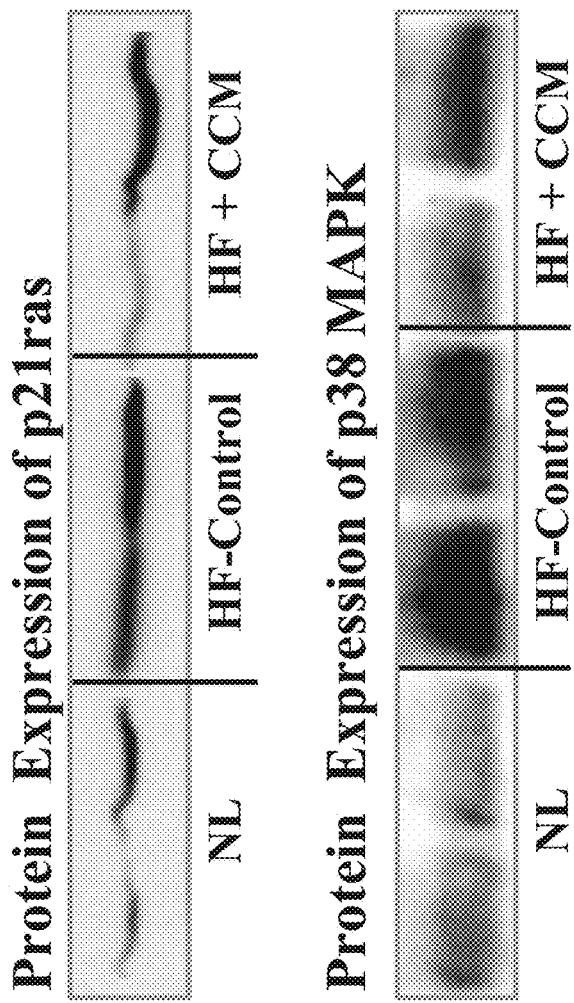
Figure 50:
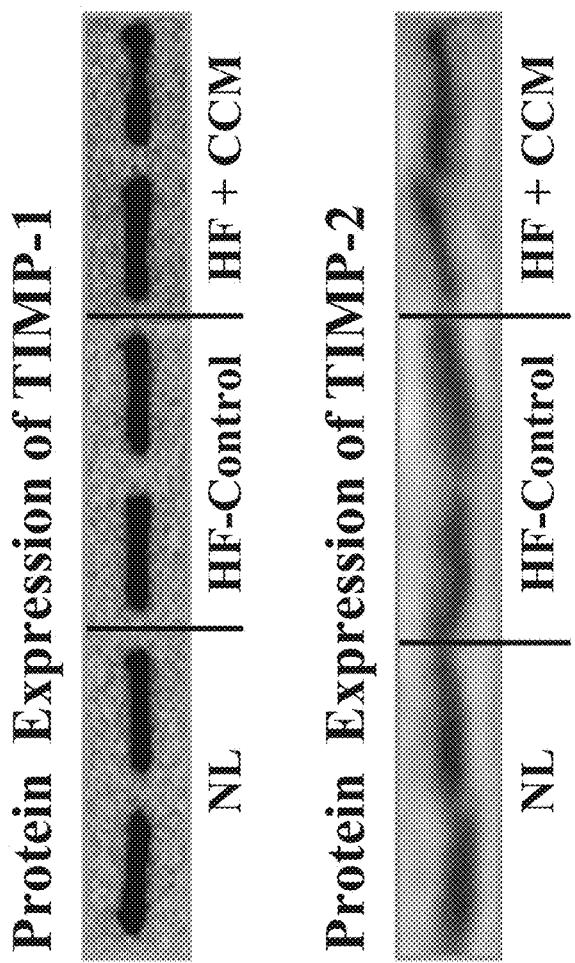

Re FIG. 5N:

TABLE 49

| Protein Expression of p21ras (Units: du) | | |
|---|---|---|
| NU | HF-Control | HF + CCM |
| 44 | 112 | 92 |
| 57 | 142 | 89 |
| 38 | 138 | 83 |
| 30 | 123 | 110 |
| 34 | 66 | 61 |
| 36 | 73 | 53 |
|  | 90 | 72 |
| 40 | 106 | 80 |
| 10 | 31 | 20 |
| 4 | 12 | 7 |

ANOVA = 0.0001
p vs. NL <0.05 <0.05
p vs. HF-Control <0.05

TABLE 50

| Protein Expression of p38 MAPK (Units: du) | | |
|---|---|---|
| NL | HF-Control | HF + CCM |
| 21 | 46 | 32 |
| 15 | 52 | 21 |
| 13 | 41 | 35 |
| 17 | 67 | 36 |
| 14 | 43 | 24 |
| 19 | 38 | 19 |
|  | 33 | 15 |
| 17 | 46 | 26 |
| 3 | 11 | 8 |
| 1 | 4 | 3 |

ANOVA = 0.0001
p vs. NL <0.05 NS
p vs. HF-Control <0.05

Re FIG. 5O:

TABLE 51

| Protein Expression of TIMP-2 (Units: du) | | |
|---|---|---|
| NL | HF-Control | HF + CCM |
| 84 | 62 | 85 |
| 73 | 55 | 80 |
| 61 | 43 | 68 |
| 93 | 89 | 72 |
| 87 | 88 | 56 |
| 88 | 84 | 79 |
|  | 81 | 86 |
| 81 | 72 | 75 |
| 12 | 18 | 11 |
| 5 | 7 | 4 |

ANOVA = 0.53
p vs. NL NS NS
p vs. HF-Control NS

Figure 5P:
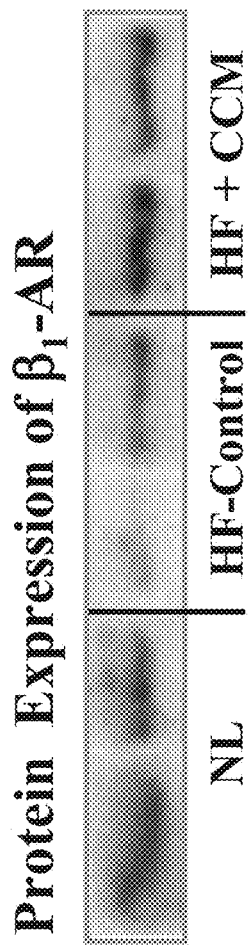

Re FIG. 5P:

TABLE 52

| Protein Expression of β1-AR (Units: du) | | |
|---|---|---|
| NL | HF-Control | HF + CCM |
| 135 | 66 | 86 |
| 75 | 30 | 97 |
| 88 | 41 | 53 |
| 111 | 64 | 95 |

TABLE 52-continued

Protein Expression of β1-AR (Units: du)

| NL | HF-Control | HF + CCM |
|---|---|---|
| 111 | 113 | 86 |
| 93 | 56 | 96 |
|  | 64 | 113 |
| 102 | 62 | 89 |
| 21 | 26 | 18 |
| 9 | 10 | 7 |

ANOVA = 0.015
p vs. NL <0.05 NS
p vs. HF-Control <0.05

Figure 5Q:
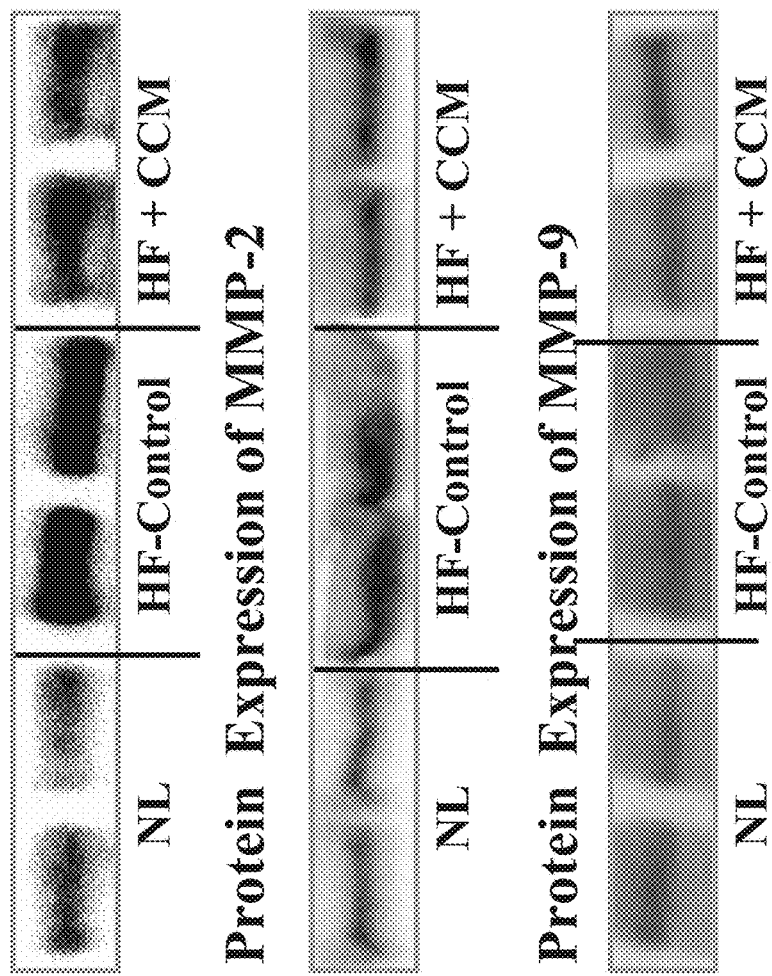

FIGS. 5Q and 5R show results for MMP-2 (in comparison to MMP-1 and MMP-9) and ANP and BNP.

Re FIG. 5Q:

TABLE 53

Protein Expression of MMP-2 (Units: du)

| NL | HF-Control | HF + CCM |
|---|---|---|
| 47 | 74 | 41 |
| 29 | 77 | 30 |
| 31 | 57 | 25 |
| 42 | 78 | 56 |
| 38 | 81 | 63 |
| 42 | 51 | 65 |
|  | 41 | 61 |
| 38 | 66 | 49 |
| 7 | 16 | 16 |
| 3 | 6 | 6 |

ANOVA = 0.0001
p vs. NL <0.05 NS
p vs. HF-Control <0.05

Re FIG. 5R:

TABLE 54

Protein Expression of ANP (Units: du)

| NL | HF-Control | HF + CCM |
|---|---|---|
| 64 | 104 | 62 |
| 77 | 179 | 60 |
| 108 | 271 | 39 |
| 82 | 128 | 89 |
| 92 | 135 | 62 |
| 103 | 113 | 76 |
|  | 97 | 54 |
| 88 | 147 | 63 |
| 17 | 61 | 16 |
| 7 | 23 | 6 |

ANOVA = 0.002
p vs. NL <0.05 NS
p vs. HF-Control <0.05

TABLE 55

Protein Expression of BNP (Units: du)

| NL | HF-Control | HF + CCM |
|---|---|---|
| 31 | 84 | 78 |
| 62 | 94 | 62 |
| 107 | 111 | 69 |
| 65 | 87 | 69 |
| 57 | 94 | 84 |
| 66 | 77 | 77 |
|  | 89 | 73 |
| 65 | 91 | 73 |
| 25 | 11 | 7 |
| 10 | 4 | 3 |

ANOVA = 0.002
p vs. NL <0.05 NS
p vs. HF-Control <0.05

Local and Remote Effects

Figure 6:
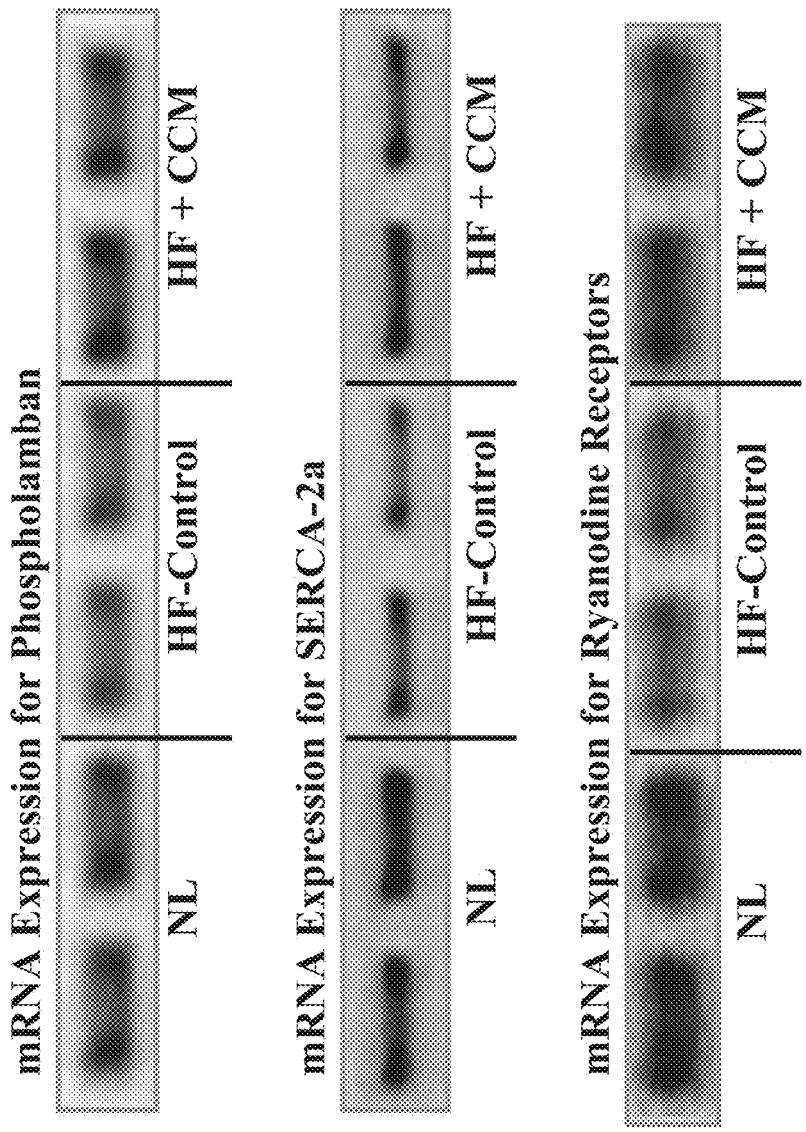
FIG. 6 shows mRNA expression levels in a cardiac septum (where signals are applied), in a chronic study, in accordance with an exemplary embodiment of the invention.

The above results showed analysis of tissue samples at the treated site. FIG. 6 shows mRNA expression levels for Phospholamban, SERCA-2a and Ryanodine receptors, showing chronic improvement in septal tissue to which a field was applied chronically.

Figure 7A:
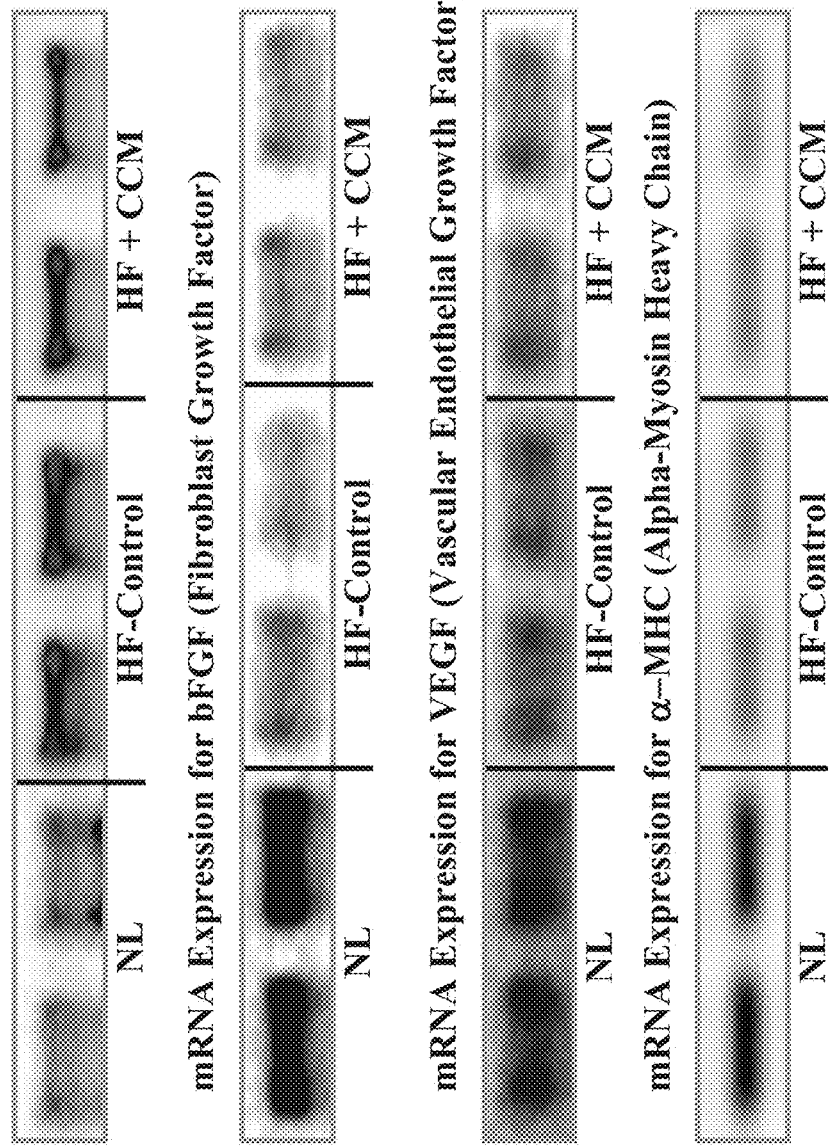
FIGS. 7A and 7B show a general lack of acute effect of CCM on tissue remote from a CCM delivery site, in accordance with an exemplary embodiment of the invention.
Figure 7B:
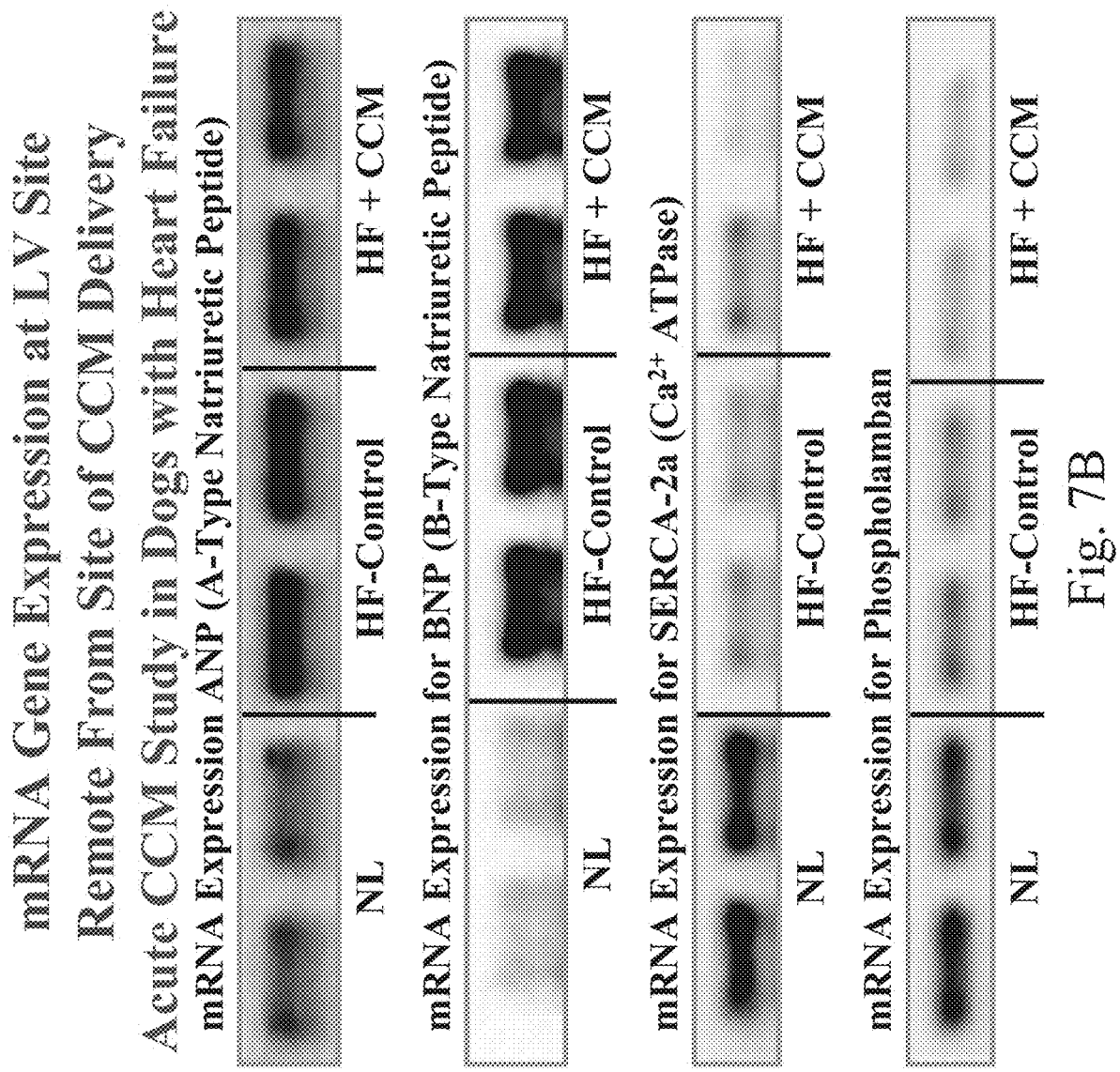

FIGS. 7A and 7B shows mRNA expression at sites remote from the application of the signal, but still within the left ventricle, at a relatively short time of four hours apparently no significant effect (mRNA, protein and/or phosphorylation) is shown. This may indicate that the effect of the CCM signal is first local, for example on a molecular level and then propagates to remote location, for example by biochemical signaling or by a mechanical signaling indicated by the change in contraction behavior of the treated tissue and/or of the chamber as a whole. The following non-limiting mechanism is suggested: the electric field causes phosphorylation of phospholamban. This in turn increases the activity/affinity of SERCA-2a for calcium and immediately improves SR calcium cycling. GATA-4 and the sodium calcium exchanger may play an additive role in the improved function. As LV function begins to improve and the LV gets smaller, many of the molecular/biochemical maladaptations begin to correct, which adds to the long-term benefits.

In an exemplary embodiment of the invention, the location to which electrification will be applied is selected based on a model of what areas will cause a biochemical or mechanical cascade in the heart and improve its function. Optionally, the size of areas is optimized to reduce power needs, while retain an expected time frame of treatment.

In an exemplary embodiment of the invention, an area to be treated is selected based on immediate response of tissue therein to electrical stimulation.

One example of a mechanical cascade is a desired change in stretching of tissue which will, as that tissue improve, propagate. Another example of mechanical cascade is selecting sufficient and correct tissue in the ventricle such that immediate hemodynamic effects (e.g., improvement) are seen and sensed by the rest of the chamber.

A possible mechanism of non-mechanical propagation (which may be utilized) is that healthy cells can help regulate ionic concentrations of neighboring cells via gap junctions between them. Alternatively or additionally, other communication may occur via the gap junctions.

FIG. 8 shows phosphorylation levels in chronically treated dogs, at the application location in the septum.

A short tabular summary of the results of FIGS. 6-8 follows:

Re FIG. 6

TABLE 56

Dos Numbers (Units: du)

| HF-Control | HF + CCM |
|---|---|
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

TABLE 57 mRNA Expression for SERCA-2a in Septum (Units: du)

| | NL | HF-Control | HF + CCM |
|---|---|---|---|
| | 238 | 172 | 207 |
| | 224 | 123 | 214 |
| | 203 | 167 | 178 |
| | 199 | 168 | 191 |
| | 226 | 151 | 179 |
| | 162 | 123 | 150 |
| | | 149 | 162 |
| Mean | 209 | 150 | 183 |
| STD | 27 | 21 | 23 |
| SEM | 11 | 8 | 9 |

ANOVA = 0.001
p vs. NL <0.05 NS
p vs. HF-Control <0.05

TABLE 58 mRNA Expression for PLB in Septum (Units: du)

| | NL | HF-Control | HF + CCM |
|---|---|---|---|
| | 241 | 255 | 394 |
| | 330 | 277 | 374 |
| | 324 | 281 | 327 |
| | 344 | 276 | 364 |
| | 368 | 290 | 352 |
| | 352 | 275 | 292 |
| | | 278 | 243 |
| Mean | 327 | 276 | 335 |
| STD | 45 | 11 | 52 |
| SEM | 18 | 4 | 20 |

ANOVA = 0.029
p vs. NL <0.05 NS
p vs. HF-Control <0.05

TABLE 59 mRNA Expression for RYR m Septum (Units: du)

| NL | HF-Control | HF + CCM |
|---|---|---|
| 272 | 287 | 267 |
| 371 | 225 | 277 |
| 289 | 229 | 300 |
| 294 | 262 | 319 |
| 321 | 232 | 323 |
| 294 | 234 | 252 |
| | 238 | 248 |

TABLE 59-continued mRNA Expression for RYR m Septum (Units: du)

| NL | HF-Control | HF + CCM |
|---|---|---|
| 307 | 244 | 284 |
| 35 | 23 | 31 |
| 14 | 9 | 12 |

ANOVA = 0.005
p vs. NL <0.05 NS
p vs. HF-Control <0.05

Re FIGS. 7A and 7B:

TABLE 60 mRNA Expression for ANP (Units: du)

| | NL | HF-Control | HF + CCM |
|---|---|---|---|
| | 155 | 301 | 342 |
| | 164 | 336 | 316 |
| | 175 | 356 | 307 |
| | 170 | 325 | 303 |
| | 229 | 318 | 291 |
| | 212 | 350 | 282 |
| Mean | 184 | 331 | 307 |
| STD | 29 | 20 | 21 |
| SEM | 12 | 8 | 9 |

ANOVA = 0.0001
p vs. NL <0.05 <0.05
p vs. HF-Control NS

TABLE 61 mRNA Expression for SERCA-2a (Units: du)

| | NL | HF-Control | HF + CCM |
|---|---|---|---|
| | 257 | 68 | 126 |
| | 266 | 50 | 57 |
| | 334 | 56 | 140 |
| | 293 | 84 | 71 |
| | 285 | 53 | 36 |
| | 263 | 47 | 38 |
| Mean | 283 | 60 | 78 |
| STD | 29 | 14 | 45 |
| SEM | 12 | 6 | 18 |

ANOVA = 0.0001
p vs. NL <0.05 <0.05
p vs. HF-Control NS

TABLE 62 mRNA Expression for VEGF (Units: du)

| | NL | HF-Control | HF + CCM |
|---|---|---|---|
| | 14 | 4 | 8 |
| | 16 | 5 | 6 |
| | 13 | 5 | 7 |
| | 19 | 14 | 11 |
| | 24 | 8 | 13 |
| | 22 | 9 | 4 |
| Mean | 18 | 8 | 8 |
| STD | 4 | 4 | 3 |
| SEM | 2 | 2 | 1 |

ANOVA = 0.001
p vs. NL <0.05 <0.05
p vs. HF-Control NS

TABLE 63 mRNA Expression for GATA-4 (Units: du)

|  | NL | HF-Control | HF + CCM |
|---|---|---|---|
|  | 121 | 352 | 341 |
|  | 129 | 367 | 349 |
|  | 145 | 373 | 333 |
|  | 126 | 350 | 325 |
|  | 133 | 377 | 300 |
|  | 136 | 394 | 262 |
| Mean | 132 | 369 | 318 |
| STD | 8 | 16 | 32 |
| SEM | 3 | 7 | 13 |

ANOVA = 0.0001
p vs. NL <0.05 <0.05
p vs. HF-Control <0.05

TABLE 64 mRNA Expression for BNP (Units: du)

| NL | HF-Control | HF + CCM |
|---|---|---|
| 320 | 1721 | 1862 |
| 299 | 1629 | 2012 |
| 331 | 1690 | 1952 |
| 294 | 1725 | 2111 |
| 361 | 1662 | 1991 |
| 349 | 2016 | 1641 |
| 326 | 1741 | 1928 |
| 27 | 140 | 162 |
| 11 | 57 | 66 |

ANOVA = 0.0001
p vs. NL <0.05 <0.05
p vs. HF-Control <0.05

TABLE 65 mRNA Expression for Phospholamban (Units: du)

| NL | HF-Control | HF + CCM |
|---|---|---|
| 18 | 9 | 14 |
| 17 | 9 | 11 |
| 17 | 7 | 11 |
| 19 | 11 | 9 |
| 20 | 7 | 6 |
| 21 | 11 | 4 |
| 19 | 9 | 9 |
| 2 | 2 | 4 |
| 1 | 1 | 1 |

ANOVA = 0.0001
p vs. NL <0.05 <0.05
p vs. HF-Control NS

TABLE 66 mRNA Expression for bFGF (Units: du)

| NL | HF-Control | HF + CCM |
|---|---|---|
| 186 | 90 | 110 |
| 195 | 76 | 100 |
| 194 | 108 | 87 |
| 215 | 77 | 88 |
| 189 | 104 | 83 |
| 200 | 100 | 70 |
| 197 | 93 | 90 |

TABLE 66-continued mRNA Expression for bFGF (Units: du)

| NL | HF-Control | HF + CCM |
|---|---|---|
| 10 | 14 | 14 |
| 4 | 6 | 6 |

ANOVA = 0.0001
p vs. NL <0.05 <0.05
p vs. HF-Control NS

TABLE 67 mRNA Expression for α-MHC (Units: du)

| NL | HF-Control | HF + CCM |
|---|---|---|
| 457 | 242 | 222 |
| 609 | 228 | 218 |
| 448 | 176 | 208 |
| 545 | 188 | 221 |
| 642 | 313 | 181 |
| 557 | 220 | 156 |
| 543 | 228 | 201 |
| 78 | 49 | 27 |
| 32 | 20 | 11 |

ANOVA = 0.0001
p vs. NL <0.05 <0.05
p vs. HF-Control NS

Re FIG. 8:

TABLE 68

Dog Numbers (Units: du)

| HF-Control | HF + CCM |
|---|---|
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

TABLE 69

Phosphorylated PLB at Serine-16 (Units: du)

|  | NL | HF-Control | HF + CCM |
|---|---|---|---|
|  | 143 | 86 | 99 |
|  | 109 | 95 | 106 |
|  | 153 | 63 | 68 |
|  | 161 | 25 | 97 |
|  | 102 | 15 | 105 |
|  | 100 | 24 | 31 |
|  |  | 43 | 106 |
| Mean | 128 | 50 | 87 |
| STD | 28 | 32 | 28 |
| SEM | 11 | 12 | 11 |

ANOVA = 0.0001
p vs. NL <0.05 <0.05
p vs. HF-Control <0.05

TABLE 70

| Phosphorylated PLB at Threonine-17 (Units: du) | | |
|---|---|---|
| NL | HF-Control | HF + CCM |
| 135 | 90 | 80 |
| 126 | 41 | 68 |
| 137 | 53 | 62 |
| 148 | 52 | 162 |
| 146 | 32 | 168 |
| 129 | 59 | 78 |
|  | 67 | 147 |
| 137 | 56 | 109 |
| 9 | 19 | 47 |
| 4 | 7 | 18 |

ANOVA = 0.0001
p vs. NL <0.05 NS
p vs. HF-Control <0.05

Effect Wash-Out Times
Effect Wash-Out Times

Figure 9A:
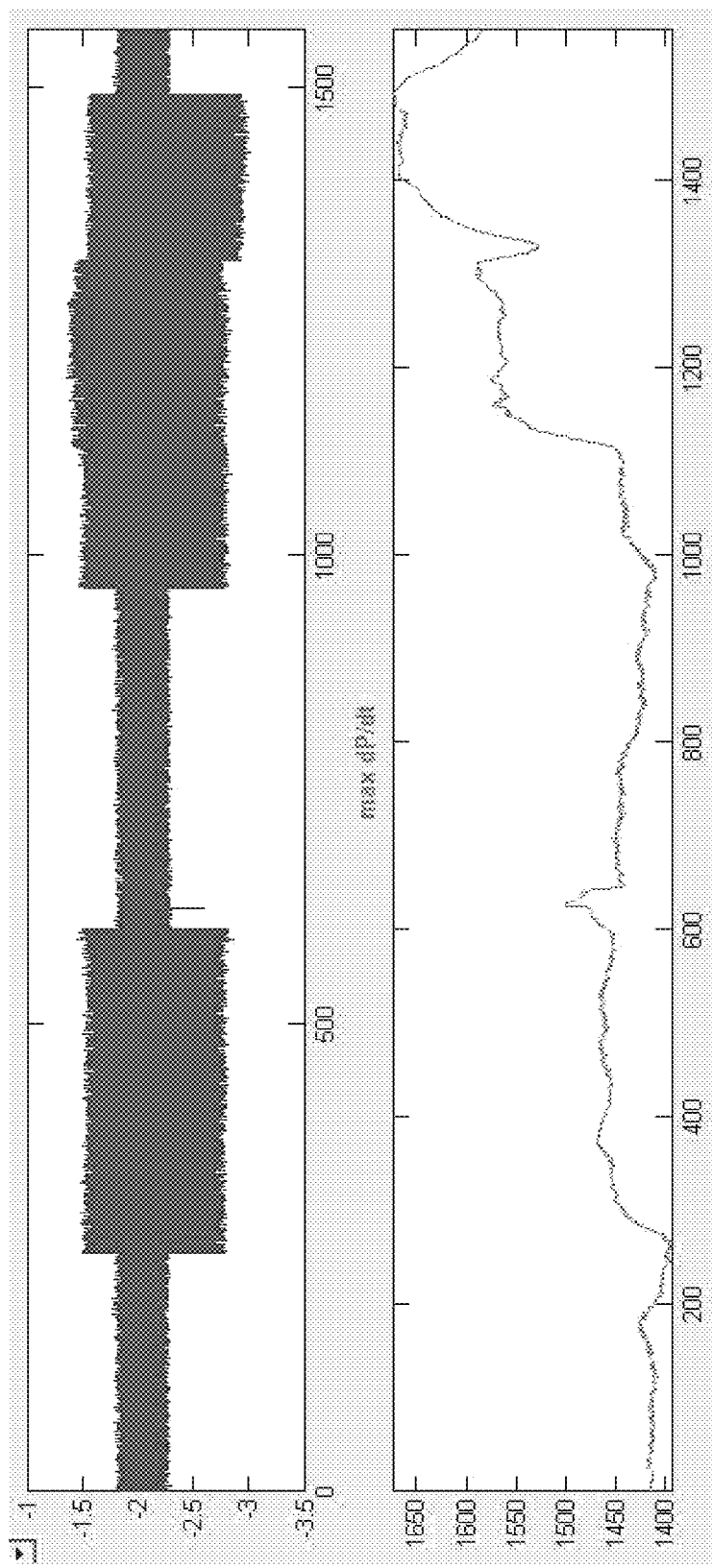
FIG. 9A and FIG. 9B show rise times and decay times for treatment using a CCM signal, in accordance with an exemplary embodiment of the invention.
Figure 9B:
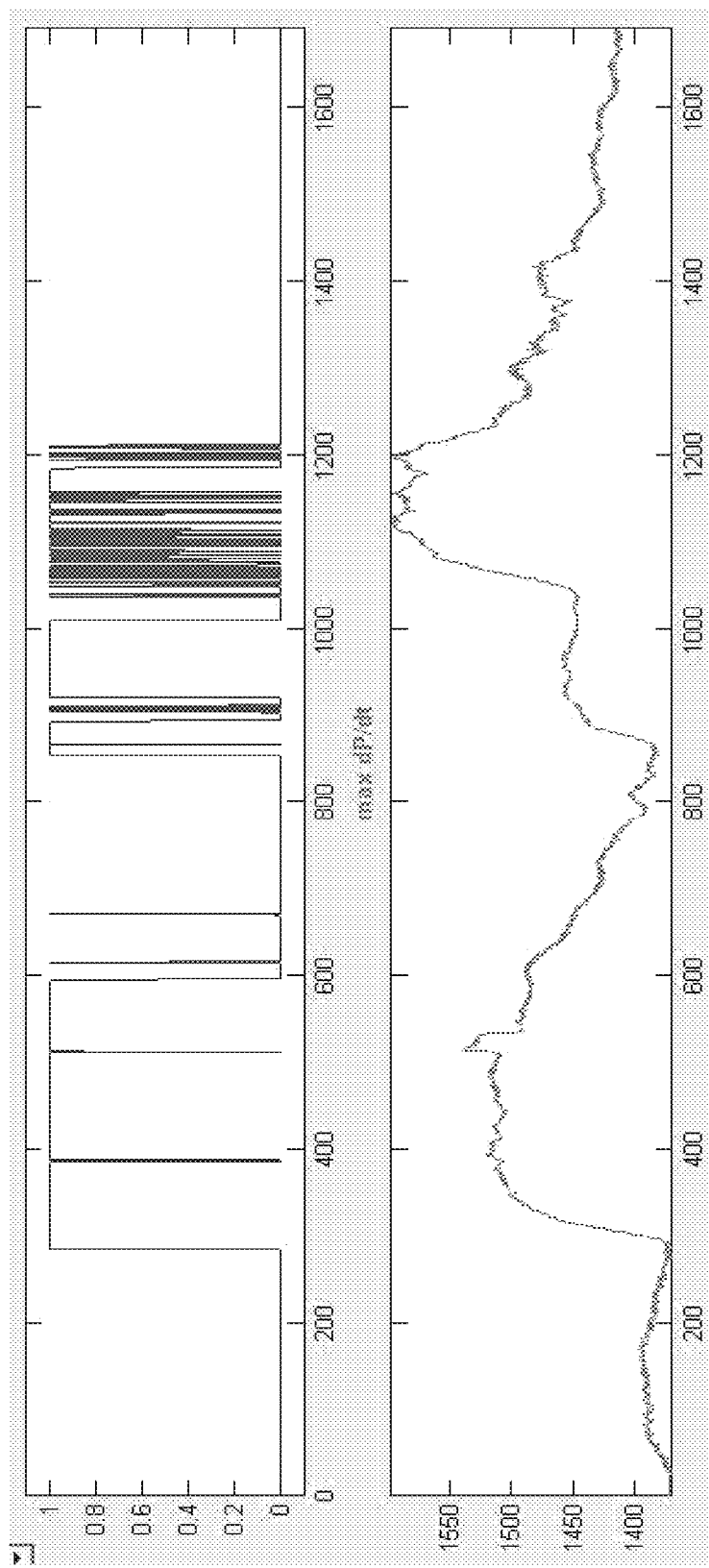

FIGS. 9A and 9B are graphs showing the relationship between rise time and decay time of a contractility increase in dogs. Similar results were observed in humans, albeit with generally slower rise times and slower decay times.

FIG. 9A, in which the scale is in seconds, shows a rise time of several tens of seconds at about time 270. Once the signal is stopped (upper graph shows the signal application times), the contractility increase decays. The blip at 600 is probably caused by an arrhythmia. The decay continues from 600 until 950. A second signal application is at about 950 with a change in signal application location at about time 1350, before the signal effect washed out.

In FIG. 9B the signal is shown as an outline of a square pulse, with the signal stopped each time an arrhythmia is detected, shown as a short pause in the signal.

Again, a rise time of several tens of seconds is found. A decay time of 230 seconds is shown for the first signal. A longer decay time of over 400 seconds is shown for a second signal. The second signal caused an increase in contractility at about 1050 seconds, due to change in the applied signals.

In an exemplary system, a controller learns the particular washout behavior of a patient and adjusts the treatment to be re-applied only after significant washout and/or be applied at a minimal length that has a washout. Optionally, the delay between application and/or length of applications are selected to optimize one or more of power consumption, danger of arrhythmia and/or discomfort to patient.

WO 2005/087310, filed as PCT/IL2005/00316 on Mar. 18, 2005, U.S. provisional application 60/719,517, filed Sep. 22, 2005 and U.S. provisional application 60/654,056, filed February 17th, the disclosures of which are incorporated herein by reference, describe methods and devices for treating metabolic diseases. In particular, 60/719,517 describes how applying a signal to a stomach has an effect on reducing blood glucose levels which lasts after the signal is stopped, for example, for more than one day. At least in combination with the results described above, this suggests that an electrical therapy may be used to change the mode of operation of tissue, on a cellular level, possibly for tissue in general or for excitable tissue at least.

It is a particular feature of some embodiments of the invention that a non-immediate effect of signal application, which lasts after the signal application is stopped, is an affirmative effect, in which the tissue exhibits a positive change in action, rather than a negative effect, for example, of preventing arrhythmia. In an exemplary embodiment of the invention, the effect is on a cellular level, rather than or in addition to an effect on an organ level, for example a cellular level as measured by protein activity and/or expression levels.

Diagnosis

In an exemplary embodiment of the invention, the above experimental results are used as a basis for diagnosis. Optionally, the diagnosis indicates one or both of a disease type and disease severity. In an exemplary embodiment of the invention, the type can be seen from the behavior of the proteins, for example comparing protein levels to calcium overload to diagnose systolic or diastolic dysfunction. In another example, the relative phosphorylation levels are used as a measure of severity.

In an exemplary embodiment of the invention, the use of multiple proteins and mRNA expression values provides a robust indicator of disease. In some embodiments, only one or two of proteins, phosphorylation and mRNA are used. Optionally, cardiac function values, such as stroke volume are used as well. Optionally, the response of tissue to a field is used as well, for example phosphorylation response.

In an exemplary embodiment of the invention, at least 3, at least 5, at least 10, at least 20 or more proteins levels, phosphorylation levels and/or mRNA levels are used to aid in diagnosis. Optionally, a table is maintained which includes ranges of values that match various disease types and/or conditions. Optionally, as therapy progresses, the patient is re-diagnosed. Optionally, the diagnosis is according to groups of mRNA and/or proteins that have associated functions.

In an exemplary embodiment of the invention, a DNA chip and/or protein chip and/or a biochip are used to measure the above levels.

In an exemplary embodiment of the invention, treatments are selected by applying the above pulses to tissue and measuring the effect. Optionally, a tissue sample is removed, for example by biopsy and a range of sequences are tested on the sample. Optionally, the results of the testing indicate which sequence might have a desired therapeutic effect. Such testing can include analysis and/or application of a treatment, such as an electric field. As noted above, at least some of the tests can be meaningfully applied to tissue homogenate and other unstructured tissue configurations.

Kits

In an exemplary embodiment of the invention, a kit is provided for performing such analyses as described herein. In an exemplary embodiment of the invention, the kit comprises a set of reagents, antibodies and/or other biochemical tools as known in the art. Alternatively or additionally, the kit comprises one or more mRNA or protein detecting chips. Alternatively or additionally, the kit comprises software for analyzing gel migration.

In an exemplary embodiment of the invention, the kit comprises a source of treatment, for example electrodes and optionally a power source, for electrifying a sample for testing its responsiveness. Optionally, the kit includes a sampling means for selecting part of the sample at a pre-described time, to check temporal response of the sample. An existing kit may be modified for use, for example, a kit available from Biosite, Inc. to measure blood levels of BNP. Such a kit could include instructions for use with the methods described herein and optionally include sampling means or a timer to ensure correct timing of activities.

The kit includes or is used with a bioreactor that includes a controllable sampling element which cans electively extract a portion of the sample in the bioreactor and test it in a separate chamber. Optionally, this is embodied using lab-on-chip technology and/or fluidic control of material flow. In an exemplary embodiment of the invention, the controllable sampling element comprises a robot and a pipette that takes part of the sample and inserts it into an assaying chamber. Various automated assaying devices are known in the art of drug discovery and may be used and/or modified to be smaller and/or simpler.

In an exemplary embodiment of the invention, the kit includes a database or a link to a database (e.g., on the internet) that links biochemical markers to tissue states, treatment states and/or disease states.

Optionally, the kits are sterile and/or frozen and optionally include instructions for use as described herein. Optionally, one or more kits are packaged with a controller designed for implantation, for use in determining suitable electrode placement therefore.

Measuring Phosphorylation

In an exemplary embodiment of the invention, the kit includes one or more antibody reagents useful for detecting phosphorylated and/or dephosphorylated forms of the proteins desired.

Optionally, tracers which are anti-body based are used in-vivo, for example provided using a catheter or using the delivery electrodes or a separate needle or other injection mechanism. Optionally, the tracer is radioactive or fluorescent.

Optionally, phosphorylation of proteins which affects ECG signals or correlated proteins which affect ECG signals is detected by detecting changes in ECG signals.

A calibration step, for example, per patient, may be carried out. Alternatively or additionally, a comparison before and after field application is used to determine change in phosphorylation.

Exemplary Cardiac Applications

In an exemplary embodiment of the invention, the above sequences are used to treat tissue plugs that are removed from the body, treated and reinserted. The reinsertion may be, for example, at the location of removal, at scarred locations, at locations bordering scars or at otherwise weakened location of the heart.

In an exemplary embodiment of the invention, the above sequences are used as part of a program to re-invigorate scar or fibrotic tissue. Optionally, the effect of the sequence is to cause at least some cells to become functioning, for example in the border of the scar.

In an exemplary embodiment of the invention, the above sequence is used to selectively increase oxygen efficiency in some parts of the heart, for example, parts with a vascular blockage thereto.

In an exemplary embodiment of the invention, the above sequences are applied to tissue transplants, for example, whole heart transplants or plug transplants (from a donor), prior to and/or after transplant.

In an exemplary embodiment of the invention, the above sequences are applied after DNA or stem cell therapy to the heart, for example, to enhance effects and/or to assist in cellular functional differentiation and/or regeneration.

In an exemplary embodiment of the invention, the above sequences are used to have a desired modeling effect on the heart, for example, modifying an elasticity and/or contractility profile of a heart portion and/or directly controlling conduction velocity.

In an exemplary embodiment of the invention, multiple methods of improving contractility are applied at a same time, or methods of improving contractility applied at a same time as methods that reduce contractility such as the initial effect of beta-blockers.

In an exemplary embodiment of the invention, contractility enhancement by effects on membrane proteins is carried out at least partly independently from protein effects on SR proteins. Optionally, the selectivity is using methods as described above.

It should be noted that these proteins are also known in other body organs, such as smooth muscle cells. Thus, an electric field as described herein can be used, for example, to modify PLB phosphorylation in blood vessel cells and/or the GI tract. Optionally, elasticity compliance is restored and vasomotor tone is restored and/or responsiveness are restored to blood vessels and/or GI tract portions using the electric field as described herein. In an exemplary embodiment of the invention, a hardened aorta is made more supple (and thus relieve cardiac problems) by suitable treatment. Vascular resistance in general, may be modified.

It should be noted that in smooth muscle cells the depolarization cycle is much longer and there is no danger of fatal arrhythmia, so more varied pulses may be attempted without significant danger and may provide longer term effects.

Pulse Optimization

In an exemplary embodiment of the invention, a method of optimizing treatments to the tissue is provided, taking into account effects on protein levels. For example, a CCM signal or a pacing signal, exercise or a pharmaceutical treatment may each (or in combination) have an effect on protein expression and/or behavior. In an exemplary embodiment of the invention, such a treatment is optimized so that it has a greater (desired) effect on proteins. In one example, a CCM signal is optimized by applying variations of the signals (e.g., different amplitude, frequencies pulse forms, etc.) to a set of tissue homogenate sets and selecting the signal(s) for which a better effect is achieved. It is noted that while this may be carried out in vivo, the ability to try out signals with various pulse parameters on tissue homogenate without the need for safety testing and worry about danger of damage to a patient/animal, can allow a much faster and/or cheaper search to be made. Searching methods as known in the art may be used. It is noted that such searching can also be carried out for small molecule drugs which have a direct effect on phosphorylation, for example.

It is noted that immediate protein levels may be results that are faster to achieve or have less noise, than measuring actual improvement in a patient. Thus, protein measurement may allow faster within-patient optimization and/or allow optimization based on the response to a small number of beats (e.g., 100, 50, 10, 3 or intermediate or fewer numbers), rather than waiting for a longer term effect which may damage the heart if it is negative.

In an exemplary embodiment of the invention, an existing device is optimized by changing its applied sequence with a sequence selected to have a desired protein effect.

In an exemplary embodiment of the invention, a device is programmed by a used selecting a desired pulse sequence form an existing set or by selecting parameters which are expected to have a desired protein effect.

It should be noted that the applied pulse sequence (optionally including non-treated beats) and/or desired effect may change over the course of a treatment. One type of change is when the patient state stabilizes and/or the focus of maladaptation changes. In one example, a first step of treatment is in stabilizing heart treatment and a second step is in increasing contractility and/or remodeling the heart.

Another type of change is where a different effect is desired at different times during a treatment, for example, a one series of beats being utilized to treat one protein and another series of beats to have another effect. It should be noted that not all treatments need to be synchronized the cardiac heart beat.

Both types of change may be controlled using feedback. Optionally, the change includes one or both of changing the sequence and changing the tissue to which the sequence is applied, for example by switching and/or by moving electrode(s).

In an exemplary embodiment of the invention, the applied sequence takes into account a provided pharmaceutical and/or a half-life in the body thereof. In an exemplary embodiment of the invention, a transmitter is provided to a patient to indicate to the controller that a medication was taken.

Optionally, the medication (or another treatment) is provided to specifically interact with the sequence. For example, a signal or medicine is provided which has a long effect and while that effect is going on, a signal or other treatment is provided which has an opposite effect that momentarily counteracts long-term effects. In one example, a medication which extends a refractory period is provided together with an electrical treatment that applies a phosphorylation-modifying signal. In another example, medication is provided to enforce resting of the cells, using a mechanism which does not prevent the CCM or CCM-like signal from working, possibly, a medication that blocks trans-membrane channels.

General

The following papers, the disclosures of which are incorporated herein by reference present various results of the effect of a CCM (Cardiac Contractility Modulation) signal, on gene expression and protein phosphorylation:

a) an abstract, Control/Tracking Number: 05-A-314176-ACC "Chronic Therapy With Non-Excitatory Cardiac Contractility Modulation Electric Signals Improves Left Ventricular Function, Reduces Myocardial Oxygen Consumption and Increases Myocardial Mechanical Efficiency", by Hani N. Sabbah, Makoto Imai, Sharad Rastogi, Naveen Sharma, Margaret P. Chandler, Walid Haddad, Yuval Mika, William C. Stanley, Henry Ford Health System, Detroit, Mich., Case Western Reserve University, Cleveland, Ohio; In American College of cardiology foundation.

b) "Non-Excitatory Cardiac Contractility Modulation Electric Signals Normalize Phosphorylation and Expression of the Sodium Calcium Exchanger in Left Ventricular Myocardium of Dogs with Heart Failure", by Ramesh C. Gupta, Sudhish Mishra, Sharad Rastogi, Makato Imai, Walid Hadad, Yuval MiKa, Hani N. Sabbah, Henry Ford Health System, Detroit, Mich., Impulse Dynamics, Mount Laurel, N.J.; In Journal of the American College of Cardiology 2005; 45:151A.

c) "Short-Term Therapy with Non-Excitatory Cardiac Contractility Modulation Electric Signals Increases Phosphorylation of Phospholamban in Left Ventricular Myocardium of Dogs With Chronic Heart Failure", by Sudhish Mishra, Ramesh C. Gupta, Sharad Rastogi, Henry Ford Health System, Detroit, Mich.; Walid Haddad, Yuval Mika, Impulse Dynamics USA, Mount Laurel, N.J.; Hani N. Sabbah, Henry Ford Health System, Detroit, Mich.; In Circulation vol. 110; page III604, 2004.

While the above described apparatus has focused on hardware and/or methods, it should be understood that the present invention includes programmable hardware, software for programmable devices, software for programming such hardware and computers including software for programming devices. For example, an external programming station may be provided, which optionally communicates with an implantable device using telemetry. Data collection using telemetry may also be practiced. In addition, computer readable media including such programs are also included. Also included are micro-code and other types of programming, as well as hardwired circuitry and ASICs. This is a list of examples and should not be considered as limiting. An exemplary device/software includes a decision making module, a timing module, a power module and/or a signal analysis modules. Section headings are provided for navigation and should not be considered as limiting their contents to that section only.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to." When the term "based on" is used in the claims it is to be interpreted as meaning "at least partially based on".

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims, as issued.

What is claimed is:

1. A method of therapy location placement for therapy of a tissue, comprising:
    selecting a location in the tissue based on a protein activity level at the location; and
    applying a therapy to the location according to said selecting,
    wherein said selecting a location based on a protein activity level comprises one or both of:
    (a) measuring protein activity by applying a test therapy to said or another location in the heart and measuring protein activity or an indication thereof, due to said test therapy; and
    (b) estimating the effect of a change in protein activity level of tissue at said location using a model of propagation of effect cascading in said heart; and
    selecting the location based on said measuring or estimating,
    wherein the method further comprises:
    deciding on suitability of a location for therapy application by applying a test therapy and deciding on suitability based on an effect on the protein activity levels of said test therapy;
    selecting a first electrical field parameter that causes an increase in phosphorylation, wherein said applying includes applying an electric field according to said first parameter to thereby cause said increase in phosphorylation and thereby change said protein activity level;
    choosing a target modification of tissue behavior for at least one of treatment of a disease, short or long term modification of tissue behavior, assessing tissue state and assessing tissue response to stimulation; and
    wherein said therapy is selected to achieve said modification;

measuring an efficacy of achieving said modification with said therapy;

further selecting a second electric stimulation parameter for achieving said modification over a longer time frame; and stimulating said tissue with a second electrical field having said second parameter.

2. The method of claim 1, wherein said applying comprises applying according to said selecting and according to an expected change in activity level of existing protein to be caused by said therapy.

3. The method of claim 1, wherein said test therapy is applied outside the body.

4. The method of claim 1, wherein said deciding on suitability of the location of therapy application based on said effect of protein activity levels of said test therapy is when an improvement in organ function is not detected.

5. The method of claim 1, further comprising:
placing an electrode at said location after said deciding.

6. The method of claim 1, further comprising:
applying another treatment to increase said effect.

7. The method of claim 1, wherein said effect includes phosphorylation.

8. The method of claim 1, wherein said deciding on suitability comprises determining an effect of said test therapy on protein activity level changes which occur within 15 minutes of an application of said test therapy.

9. The method of claim 1, wherein said measuring comprises measuring a phosphorylation level of a protein, which protein is affected in less than 15 minutes by said test therapy.

10. The method of claim 1, further comprising:
changing a location of therapy based on said effect of said test therapy.

11. The method of claim 1, wherein said applying is to a location of treatment in an organ the method further comprising:
selecting said location of treatment, according to a desired propagation of said treatment in an organ including said tissue.

12. The method of claim 11, wherein said applying is in vivo.

13. The method of claim 11, wherein said propagation is at least one of a mechanical propagation and a biochemical propagation.

14. The method of claim 11, wherein said location comprises a plurality of locations.

15. The method of claim 1, wherein said therapy includes electrical therapy for the heart.

16. The method of claim 15, wherein said applying includes applying a non-excitatory electrical signal to said tissue.

17. The method of claim 1, wherein said further selecting of said second parameter is to affect a gene expression.

18. The method of claim 1, wherein said further selecting of said second parameter is to affect at least one of a mechanical and a functional remodeling of a heart.

19. The method of claim 1, further comprising:
measuring an efficacy of achieving said modification with said second electric field; and determining a combination electrical parameter for achieving said modification wherein said combination has at least one of the following advantages: it uses less power than either the first and said second field and it more fully achieves said modification than either said first field or said second field.

20. The method of claim 1, wherein said first and second field applications differ in a least one of power, shape, repetition number, and duration of application.

21. The method of claim 1, wherein said selecting comprises applying a test therapy to said tissue and measuring an effect of said therapy.

22. The method of claim 1, wherein said applying comprises causing a change in activity level of existing protein.

23. The method of claim 1, wherein said selection is applied during electrode implantation, to select an implantation area of electrodes in the heart.

24. The method of claim 1, further wherein said test therapy is applied for less than 100 seconds.

* * * * *